US011859172B2

(12) United States Patent
Wang

(10) Patent No.: US 11,859,172 B2
(45) Date of Patent: Jan. 2, 2024

(54) PROGRAMMABLE AND PORTABLE CRISPR-CAS TRANSCRIPTIONAL ACTIVATION IN BACTERIA

(71) Applicant: The Trustees of Columbia University in the City of New York, New York, NY (US)

(72) Inventor: Harris He Wang, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 202 days.

(21) Appl. No.: 17/139,471

(22) Filed: Dec. 31, 2020

(65) Prior Publication Data

US 2021/0207139 A1    Jul. 8, 2021

Related U.S. Application Data

(60) Provisional application No. 62/956,487, filed on Jan. 2, 2020.

(51) Int. Cl.
*C12N 15/10*  (2006.01)
*C12N 15/113* (2010.01)
*C12N 9/22*   (2006.01)

(52) U.S. Cl.
CPC .............. *C12N 15/113* (2013.01); *C12N 9/22* (2013.01); *C12N 15/1093* (2013.01); *C07K 2319/00* (2013.01); *C12N 2310/3517* (2013.01)

(58) Field of Classification Search
CPC .... C12N 15/113; C12N 9/22; C12N 15/1093; C12N 15/1058; C12N 15/70; C12N 15/74; C07K 2319/00
See application file for complete search history.

(56) References Cited

U.S. PATENT DOCUMENTS

| | | | |
|---|---|---|---|
| 5,034,506 A | 7/1991 | Summerton et al. | |
| 7,514,257 B2 | 4/2009 | Lee et al. | |
| 10,184,126 B2 | 1/2019 | Yang et al. | |
| 10,266,850 B2 | 4/2019 | Doudna et al. | |
| 2016/0200779 A1 | 7/2016 | Liu et al. | |
| 2017/0204407 A1 | 7/2017 | Gilbert et al. | |
| 2018/0094257 A1 | 4/2018 | Wang et al. | |
| 2019/0153476 A1 | 5/2019 | Zhang | |
| 2019/0309087 A1 | 10/2019 | Kedmi et al. | |
| 2019/0390204 A1 | 12/2019 | Zhang et al. | |

FOREIGN PATENT DOCUMENTS

WO    WO 2010/075424    7/2010

OTHER PUBLICATIONS

Bikard et al (Programmable repression and activation of bacterial gene expression using an engineered CRISPR-Cas system. Nucleic Acid Research, vol. 41, Jun. 2013, cited in IDS dated Dec. 16, 2022). (Year: 2013).*
Chen et al (Fusion Protein Linkers: Property, Design and Functionality. Adv Drug Deliv Rev, vol. 65, Oct. 2013) (Year: 2013).*
Gregory et al (An Artificial Activator that Contacts a Normally Occluded Surface of the RNA Polymerase Holoenzyme. J Mol Biol, vol. 353, Sep. 2005) (Year: 2005).*
WT AsiA aligned with SEQ ID No. 80 (Year: 2023).*
Dove et al (Bacterial Two-Hybrid Analysis of Interactions between Region 4 of the σ70 Subunit of RNA Polymerase and the Transcriptional Regulators Rsd from *Escherichia coli* and AlgQ from *Pseudomonas aeruginosa*. JBacteriology, vol. 183, Nov. 2001) (Year: 2001).*
Dove et al (Conversion of the ω subunit of *Escherichia coli* RNA polymerase into a transcriptional activator or an activation target. Genes & Dev., vol. 12, 1998, hereinafter Dove 1998) (Year: 1998).*
McCullum et al (Random Mutagenesis by Error-Prone PCR. Chapter 7 in Book: In Vitro Mutagenesis Protocols, Third Edition, Editor Jeff Braman, Mar. 2010) (Year: 2010).*
Altschul et al., "Basic local alignment search tool" J Mol Biol. Oct. 5, 1990;215(3):403-10.
Altschul et al., "Gapped BLAST and PSI-BLAST: a new generation of protein database search programs." Nucleic Acids Res. Sep. 1, 1997;25(17):3389-402.
Biegert et al., "Sequence context-specific profiles for homology searching" Proc. Natl. Acad. Sci. USA 2009, 106(10): 3770-3775.
Bikard et al., "Programmable repression and activation of bacterial gene expression using an engineered CRISPR-Cas system." Nucleic Acids Res. Aug. 2013; 41(15): 7429-37.
Braasch and Corey, "Novel antisense and peptide nucleic acid strategies for controlling gene expression" Biochemistry. Apr. 9, 2002; 41(14):4503-10.
Chappell et al., "Computational design of small transcription activating RNAs for versatile and dynamic gene regulation" Nature Communications Oct. 2017, 8: 1051 pp. 1-12.
Dong et al., "Synthetic CRISPR-Cas gene activators for transcriptional reprogramming in bacteria" Nat Commun. Jun. 2018; 9(1): pp. 1-11.
Heigwer et al. "E-CRISP: fast CRISPR target site identification" Nat Methods 2014, 11(2): 122-123.
Ibraheem et al. "Gene therapy and DNA delivery systems" Int J Pharm. Jan. 1, 2014;459(1-2):70-83.
International Search Report and Written Opinion dated Sep. 14, 2021, Intl. Appl. No. PCT/US2020/067666, 12 pages.
Jayaraman et al., "Blue light-mediated transcriptional activation and repression of gene expression in bacteria" Nucleic Acids Research Aug. 2006, 44(14): 6994-7005.

(Continued)

*Primary Examiner* — Kara D Johnson
*Assistant Examiner* — Matasha Dhar
(74) *Attorney, Agent, or Firm* — Casimir Jones, S.C.; Kelly A. Barton

(57) ABSTRACT

The present invention relates to components, systems, and methods transcriptional modification (e.g., transcriptional activation) or methods of identifying transcriptional effectors based on Cas9-transcription effector fusion protein and gRNA sequence targeting.

11 Claims, 22 Drawing Sheets

Specification includes a Sequence Listing.

(56) References Cited

OTHER PUBLICATIONS

Johns et al. "Metagenomic mining of regulatory elements enables programmable species-selective gene expression" Nat Methods. May 2018;15(5):323-329.

Lawson et al., "Mechanism for the Regulated Control of Bacterial Transcription Termination by a Universal Adaptor Protein" Molecular Cell 2018, 71(6): 911-922.

Lee et al., "Programmable control of bacterial gene expression with the combined CRISPR and antisense RNA system" Nucleic Acids Research Mar. 2016, 44(5): 2462-2473

Liu et al., "Engineered CRISPRa enables programmable eukaryote-like gene activation in bacteria." Nat Commun. 2019 Aug; 10(1): pp. 1-6.

Nayerossadat et al., "Viral and nonviral delivery systems for gene delivery" Adv Biomed Res. 2012; 1:27.

Prykhozhij et al. "CRISPR MultiTargeter: A Web Tool to Find Common and Unique CRISPR Single Guide RNA Targets in a Set of Similar Sequences" PLoS ONE 2015, 10(3), pp. 1-18.

Qi et al., "Repurposing CRISPR as an RNA-guided platform for sequence-specific control of gene expression" Cell vol. Feb. 2013, 152(5): 1173-1183.

Rock et al., "Programmable transcriptional repression in mycobacteria using an orthogonal CRISPR interference platform" Nat Microbiol. Feb. 6, 2017; 2:16274.

Soding, "Protein homology detection by HMM-HMM comparison" Bioinformatics 2005, 21(7): 951-960.

Srivatsan et al., "Control of bacterial transcription, translation and replication by (p)ppGpp" Current Opinion in Microbiology Apr. 2008, 11(2): 100-105.

Wahlesedt et al., "Potent and nontoxic antisense oligonucleotides containing locked nucleic acids" Proc. Natl. Acad. Sci. USA. 2000, 97: 5633-5638.

Wang et al., "Cyclohexene Nucleic Acids (CeNA): Serum Stable Oligonucleotides that Activate RNase H and Increase Duplex Stability with Complementary RNA" J. Am. Chem. Soc. 2000, 122(36): 8595-8602.

Xiao et al. "CasOT: a genome-wide Cas9/gRNA off-target searching tool" Bioinformatics 2014, 30(8): 1180-1182.

Yim et al., "Multiplex transcriptional characterizations across diverse bacterial species using cell-free systems" (2019) Mol Syst Biol 15: e8875, pp. 1-15.

Zhu et al. "Serum Uric Acid Is Associated with Incident Chronic Kidney Disease in Middle-Aged Populations: A Meta-Analysis of 15 Cohort Studies" PLoS ONE 2014, 9(6): e100801, pp. 1-9.

Zhu et al., "Overview of guide RNA design tools for CRISPR-CasQ genome editing technology" Frontiers in Biology 2015, 10(4):289-296.

Brophy et al., "Engineered integrative and conjugative elements for efficient and inducible DNA transfer to undomesticated bacteria" Nat Microbiol. Sep. 2018;3(9):1043-1053.

Chatterji et al., "The role of the omega subunit of RNA polymerase in expression of the relA gene in *Escherichia coli*" FEMS Microbiol Lett. Feb. 2007;267(1):51-5.

Chavez et al., "Comparison of Cas9 activators in multiple species." Nat Methods. Jul. 2016; 13(7):563-567.

Cho et al., "High-Level dCas9 Expression Induces Abnormal Cell Morphology in *Escherichia coli*" ACS Synth Biol. Apr. 20, 2018;7(4):1085-1094.

Cohen et al., "Commensal bacteria make GPCR ligands that mimic human signalling molecules" Nature. Sep. 7, 2017; 549(7670):48-53.

Cui et al., "A CRISPRi screen in *E. coli* reveals sequence-specific toxicity of dCasQ" Nat Commun. May 15, 2018; 9(1):1912.

Donia et al., "A systematic analysis of biosynthetic gene clusters in the human microbiome reveals a common family of antibiotics" Cell. Sep. 11, 2014; 158(6):1402-1414.

Griffith & Wolf, Jr., "A comprehensive alanine scanning mutagenesis of the *Escherichia coli* transcriptional activator SoxS: identifying amino acids important for DNA binding and transcription activation" J Mol Biol. Sep. 13, 2002;322(2):237-57.

Hu et al., "Transposon mutagenesis identifies genes which control antimicrobial drug tolerance in stationary-phase *Escherichia coli*" FEMS Microbiol Lett. Feb. 1, 2005; 243(1):117-24.

Iqbal et al., "Natural product discovery through improved functional metagenomics in *Streptomyces*." J Am Chem Soc. Aug. 3, 2016;138(30):9341-4.

Konermann et al., "Genome-scale transcriptional activation by an engineered CRISPR-CasQ complex" Nature. Jan. 29, 2015;517(7536):583-8.

Liu et al., "CRISPR Activation Screens Systematically Identify Factors that Drive Neuronal Fate and Reprogramming" Cell Stem Cell. Nov. 1, 2018;23(5):758-771.e8.

Maeder et al., "CRISPR RNA-guided activation of endogenous human genes" Nat Methods. Oct. 2013;10(10):977-9.

Minakhin & Severinov, "Transcription regulation by bacteriophage T4 AsiA" Protein Expr Purif. May 2005;41(1):1-8.

Perez-Pinera et al., "RNA-guided gene activation by CRISPR-Cas9-based transcription factors" Nat Methods. Oct. 2013; 10(10):973-6.

Peters et al., "Enabling genetic analysis of diverse bacteria with Mobile-CRISPRi" Nat Microbiol. Feb. 2019; 4(2):244-250.

Rhonda et al., "Metagenomic engineering of the mammalian gut microbiome in situ" Nat Methods. Feb. 2019; 16(2):167-170.

Slusarczyk & Weiss, "Foundations for the design and implementation of synthetic genetic Circuits" Nat Rev Genet. May 18, 2012;13(6):406-20.

Stead et al. "RNAsnap™: a rapid, quantitative and inexpensive, method for isolating total RNA from bacteria" Nucleic Acids Res. Nov. 1, 2012;40(20):e156.

St-Pierre et al. 2013, "One-step Cloning and Chromosomal integration of DNA" ACS Synth Biol. Sep. 20, 2013;2(9):537-41.

Weiss et al. "The ω subunit governs RNA polymerase stability and transcriptional specificity in *Staphylococcus aureus*" J Bacteriol. Dec. 28, 2016; 199(2):e00459-16.

Yaung et al., "Improving microbial fitness in the mammalian gut by in vivo temporal functional metagenomics" Mol Syst Biol. Mar. 2015;11(3):788.

* cited by examiner

| Phage species | AsiA homologs | |
|---|---|---|
| [T4 bacteriophage] | NQNSFRKIVSEL | SEQ ID NO: 82 |
| [T4 bacterophage m2.1: EVOLVED] | NRNSFRKIISKL | SEQ ID NO: 83 |
| [Salmonella phage SG1] | NQNSFRKIVSEL | SEQ ID NO: 82 |
| [Yersinia phage fPS-65] | NQNSFRKIVSEL | SEQ ID NO: 82 |
| [Shigella phage SSE1] | NQNSFRKITNL | SEQ ID NO: 84 |
| [Citrobacter phage Moon] | NQGSFRKISEL | SEQ ID NO: 85 |
| [Edwardsiella phage PEi20] | NGVSFNKLF-DL | SEQ ID NO: 86 |
| [Erwinia phage Cronus] | NVASFKKMIKEL | SEQ ID NO: 87 |
| [Klebsiella phage vB_Kpn_F48] | NSANFRKMVAEL | SEQ ID NO: 88 |
| [Serratia phage PS2] | TVGNFRQVMTEL | SEQ ID NO: 89 |
| [Stenotrophomonas phage IME13] | TRAGFRQMMKRL | SEQ ID NO: 90 |
| [Aeromonas virus 44RR2] | TRAGFRQMMKRL | SEQ ID NO: 90 |
| [Proteus phage PM2] | NKSNLKSLVKSL | SEQ ID NO: 91 |
| [Morganella phage vB_MmoM_MP1] | SKVNMATLFERM | SEQ ID NO: 92 |
| [Cronobacter phage S13] | SKMSFRKMNERL | SEQ ID NO: 93 |
| [Pseudomonas phage PspYZU05] | NKYRLKRMFFN- | SEQ ID NO: 94 | residue 51    58 60

FIG. 5A

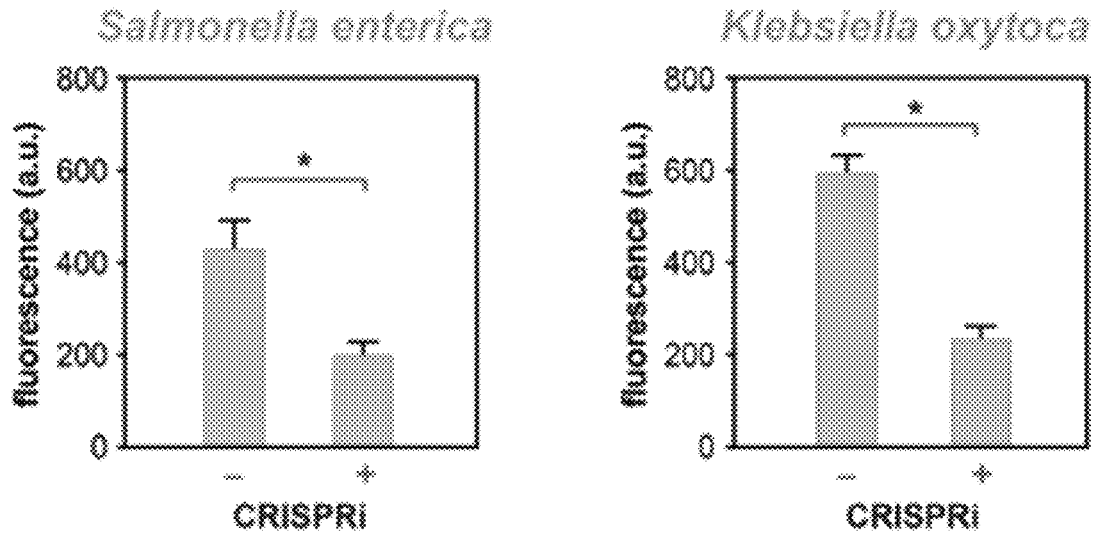

FIG. 5B

SEQUENCE LISTING

<160> NUMBER OF SEQ ID NOS: 96

<210> SEQ ID NO 1
<211> LENGTH: 12

```
<212> TYPE: PRT
<213> ORGANISM: artificial sequence
<220> FEATURE:
<223> OTHER INFORMATION: Synthetic

<400> SEQUENCE: 1

Ser Ala Gly Gly Gly Gly Ser Gly Gly Gly Ser
1               5                   10

<210> SEQ ID NO 2
<211> LENGTH: 12
<212> TYPE: PRT
<213> ORGANISM: artificial sequence
<220> FEATURE:
<223> OTHER INFORMATION: Synthetic

<400> SEQUENCE: 2

Cys Ala Gly Gly Gly Gly Ser Gly Gly Gly Ser
1               5                   10

<210> SEQ ID NO 3
<211> LENGTH: 11
<212> TYPE: PRT
<213> ORGANISM: artificial sequence
<220> FEATURE:
<223> OTHER INFORMATION: Synthetic

<400> SEQUENCE: 3

Ala Ala Asn Asp Glu Asn Tyr Ala Leu Ala Ala
1               5                   10

<210> SEQ ID NO 4
<211> LENGTH: 20
<212> TYPE: DNA
<213> ORGANISM: artificial sequence
<220> FEATURE:
<223> OTHER INFORMATION: Synthetic

<400> SEQUENCE: 4
atgtaacacc gtgcgtgttg                                               20

<210> SEQ ID NO 5
<211> LENGTH: 20
<212> TYPE: DNA
<213> ORGANISM: artificial sequence
<220> FEATURE:
<223> OTHER INFORMATION: Synthetic

<400> SEQUENCE: 5
gaagatccgg cctgcagcca                                               20

<210> SEQ ID NO 6
<211> LENGTH: 20
<212> TYPE: DNA
<213> ORGANISM: artificial sequence
<220> FEATURE:
<223> OTHER INFORMATION: Synthetic

<400> SEQUENCE: 6
ggctcgagtc gacagttcat                                               20

<210> SEQ ID NO 7
<211> LENGTH: 20
<212> TYPE: DNA
<213> ORGANISM: artificial sequence
<220> FEATURE:
<223> OTHER INFORMATION: Synthetic
```

<400> SEQUENCE: 7
ctacggaact cttgtgcgta                                               20

<210> SEQ ID NO 8
<211> LENGTH: 20
<212> TYPE: DNA
<213> ORGANISM: artificial sequence
<220> FEATURE:
<223> OTHER INFORMATION: Synthetic

<400> SEQUENCE: 8
gcaaaagctc atttctgaag                                               20

<210> SEQ ID NO 9
<211> LENGTH: 14
<212> TYPE: DNA
<213> ORGANISM: artificial sequence
<220> FEATURE:
<223> OTHER INFORMATION: Synthetic

<400> SEQUENCE: 9
aactcttgtg cgta                                                     14

<210> SEQ ID NO 10
<211> LENGTH: 20
<212> TYPE: DNA
<213> ORGANISM: artificial sequence
<220> FEATURE:
<223> OTHER INFORMATION: Synthetic

<400> SEQUENCE: 10
ttgacagcta gctcagtcct                                               20

<210> SEQ ID NO 11
<211> LENGTH: 20
<212> TYPE: DNA
<213> ORGANISM: artificial sequence
<220> FEATURE:
<223> OTHER INFORMATION: Synthetic

<400> SEQUENCE: 11
gctagcgaat tcctttaaag                                               20

<210> SEQ ID NO 12
<211> LENGTH: 20
<212> TYPE: DNA
<213> ORGANISM: artificial sequence
<220> FEATURE:
<223> OTHER INFORMATION: Synthetic

<400> SEQUENCE: 12
ccatctaatt caacaagaat                                               20

<210> SEQ ID NO 13
<211> LENGTH: 20
<212> TYPE: DNA
<213> ORGANISM: artificial sequence
<220> FEATURE:
<223> OTHER INFORMATION: Synthetic

<400> SEQUENCE: 13
gaattagatg gtgatgttaa                                               20

<210> SEQ ID NO 14

```
<211> LENGTH: 20
<212> TYPE: DNA
<213> ORGANISM: artificial sequence
<220> FEATURE:
<223> OTHER INFORMATION: Synthetic

<400> SEQUENCE: 14
tctgggtgcc ttcatacgga                                              20

<210> SEQ ID NO 15
<211> LENGTH: 20
<212> TYPE: DNA
<213> ORGANISM: artificial sequence
<220> FEATURE:
<223> OTHER INFORMATION: Synthetic

<400> SEQUENCE: 15
tttatgtaat aaaaattatg                                              20

<210> SEQ ID NO 16
<211> LENGTH: 20
<212> TYPE: DNA
<213> ORGANISM: artificial sequence
<220> FEATURE:
<223> OTHER INFORMATION: Synthetic

<400> SEQUENCE: 16
gctgtcagaa agggatgagc                                              20

<210> SEQ ID NO 17
<211> LENGTH: 20
<212> TYPE: DNA
<213> ORGANISM: artificial sequence
<220> FEATURE:
<223> OTHER INFORMATION: Synthetic

<400> SEQUENCE: 17
tgccaatttg ctaaacatta                                              20

<210> SEQ ID NO 18
<211> LENGTH: 20
<212> TYPE: DNA
<213> ORGANISM: artificial sequence
<220> FEATURE:
<223> OTHER INFORMATION: Synthetic

<400> SEQUENCE: 18
ataatacatg gctgattatg                                              20

<210> SEQ ID NO 19
<211> LENGTH: 20
<212> TYPE: DNA
<213> ORGANISM: artificial sequence
<220> FEATURE:
<223> OTHER INFORMATION: Synthetic

<400> SEQUENCE: 19
tttttatcaa tgtaaagaaa                                              20

<210> SEQ ID NO 20
<211> LENGTH: 20
<212> TYPE: DNA
<213> ORGANISM: artificial sequence
<220> FEATURE:
<223> OTHER INFORMATION: Synthetic

<400> SEQUENCE: 20
```
aataatggtt tcttagacgt                          20

<210> SEQ ID NO 21
<211> LENGTH: 20
<212> TYPE: DNA
<213> ORGANISM: artificial sequence
<220> FEATURE:
<223> OTHER INFORMATION: Synthetic

<400> SEQUENCE: 21
aaaagggaat aagggcgaca                          20

<210> SEQ ID NO 22
<211> LENGTH: 20
<212> TYPE: DNA
<213> ORGANISM: artificial sequence
<220> FEATURE:
<223> OTHER INFORMATION: Synthetic

<400> SEQUENCE: 22
aagctgaaga aaaatgagca                          20

<210> SEQ ID NO 23
<211> LENGTH: 20
<212> TYPE: DNA
<213> ORGANISM: artificial sequence
<220> FEATURE:
<223> OTHER INFORMATION: Synthetic

<400> SEQUENCE: 23
caatttaatg ataaacttca                          20

<210> SEQ ID NO 24
<211> LENGTH: 20
<212> TYPE: DNA
<213> ORGANISM: artificial sequence
<220> FEATURE:
<223> OTHER INFORMATION: Synthetic

<400> SEQUENCE: 24
agtcttgcgc tgattgttcc                          20

<210> SEQ ID NO 25
<211> LENGTH: 20
<212> TYPE: DNA
<213> ORGANISM: artificial sequence
<220> FEATURE:
<223> OTHER INFORMATION: Synthetic

<400> SEQUENCE: 25
ataccgatca gcgcaagcca                          20

<210> SEQ ID NO 26
<211> LENGTH: 20
<212> TYPE: DNA
<213> ORGANISM: artificial sequence
<220> FEATURE:
<223> OTHER INFORMATION: Synthetic

<400> SEQUENCE: 26
tttttactgg cactgtttat                          20

<210> SEQ ID NO 27
<211> LENGTH: 20
<212> TYPE: DNA

```
<213> ORGANISM: artificial sequence
<220> FEATURE:
<223> OTHER INFORMATION: Synthetic

<400> SEQUENCE: 27
ctgataaaga tttaaaagtc                                           20

<210> SEQ ID NO 28
<211> LENGTH: 20
<212> TYPE: DNA
<213> ORGANISM: artificial sequence
<220> FEATURE:
<223> OTHER INFORMATION: Synthetic

<400> SEQUENCE: 28
cggtgttaca ttaggcatac                                           20

<210> SEQ ID NO 29
<211> LENGTH: 20
<212> TYPE: DNA
<213> ORGANISM: artificial sequence
<220> FEATURE:
<223> OTHER INFORMATION: Synthetic

<400> SEQUENCE: 29
aacacgcacg gtgttacatt                                           20

<210> SEQ ID NO 30
<211> LENGTH: 20
<212> TYPE: DNA
<213> ORGANISM: artificial sequence
<220> FEATURE:
<223> OTHER INFORMATION: Synthetic

<400> SEQUENCE: 30
cgtgcgtgtt gtggaagatc                                           20

<210> SEQ ID NO 31
<211> LENGTH: 20
<212> TYPE: DNA
<213> ORGANISM: artificial sequence
<220> FEATURE:
<223> OTHER INFORMATION: Synthetic

<400> SEQUENCE: 31
cggatcttcc acaacacgca                                           20

<210> SEQ ID NO 32
<211> LENGTH: 20
<212> TYPE: DNA
<213> ORGANISM: artificial sequence
<220> FEATURE:
<223> OTHER INFORMATION: Synthetic

<400> SEQUENCE: 32
gccaaggtga taatccatag                                           20

<210> SEQ ID NO 33
<211> LENGTH: 20
<212> TYPE: DNA
<213> ORGANISM: artificial sequence
<220> FEATURE:
<223> OTHER INFORMATION: Synthetic

<400> SEQUENCE: 33 ttatcaccttt ggctgcaggc                                          20
```

<210> SEQ ID NO 34
<211> LENGTH: 20
<212> TYPE: DNA
<213> ORGANISM: artificial sequence
<220> FEATURE:
<223> OTHER INFORMATION: Synthetic

<400> SEQUENCE: 34
tggattatca ccttggctgc                                              20

<210> SEQ ID NO 35
<211> LENGTH: 20
<212> TYPE: DNA
<213> ORGANISM: artificial sequence
<220> FEATURE:
<223> OTHER INFORMATION: Synthetic

<400> SEQUENCE: 35
gcctctatgg attatcacct                                              20

<210> SEQ ID NO 36
<211> LENGTH: 20
<212> TYPE: DNA
<213> ORGANISM: artificial sequence
<220> FEATURE:
<223> OTHER INFORMATION: Synthetic

<400> SEQUENCE: 36
actgtcgact cgagcctcta                                              20

<210> SEQ ID NO 37
<211> LENGTH: 19
<212> TYPE: DNA
<213> ORGANISM: artificial sequence
<220> FEATURE:
<223> OTHER INFORMATION: Synthetic

<400> SEQUENCE: 37
cagttcatag gtgattgct                                               19

<210> SEQ ID NO 38
<211> LENGTH: 20
<212> TYPE: DNA
<213> ORGANISM: artificial sequence
<220> FEATURE:
<223> OTHER INFORMATION: Synthetic

<400> SEQUENCE: 38
ctcaggacat ttctgttaga                                              20

<210> SEQ ID NO 39
<211> LENGTH: 20
<212> TYPE: DNA
<213> ORGANISM: artificial sequence
<220> FEATURE:
<223> OTHER INFORMATION: Synthetic

<400> SEQUENCE: 39
cttgtgcgta aggaaaagta                                              20

<210> SEQ ID NO 40
<211> LENGTH: 20
<212> TYPE: DNA
<213> ORGANISM: artificial sequence
<220> FEATURE:

<223> OTHER INFORMATION: Synthetic

<400> SEQUENCE: 40
aacacaaact tgaacagcta                                               20

<210> SEQ ID NO 41
<211> LENGTH: 20
<212> TYPE: DNA
<213> ORGANISM: artificial sequence
<220> FEATURE:
<223> OTHER INFORMATION: Synthetic

<400> SEQUENCE: 41
tttctgaaga ggacttgttg                                               20

<210> SEQ ID NO 42
<211> LENGTH: 20
<212> TYPE: DNA
<213> ORGANISM: artificial sequence
<220> FEATURE:
<223> OTHER INFORMATION: Synthetic

<400> SEQUENCE: 42
atttctccct cctggcagta                                               20

<210> SEQ ID NO 43
<211> LENGTH: 20
<212> TYPE: DNA
<213> ORGANISM: artificial sequence
<220> FEATURE:
<223> OTHER INFORMATION: Synthetic

<400> SEQUENCE: 43
tggaggacac tcttgactgc                                               20

<210> SEQ ID NO 44
<211> LENGTH: 20
<212> TYPE: DNA
<213> ORGANISM: artificial sequence
<220> FEATURE:
<223> OTHER INFORMATION: Synthetic

<400> SEQUENCE: 44
aacccgagcg acaaacatct                                               20

<210> SEQ ID NO 45
<211> LENGTH: 20
<212> TYPE: DNA
<213> ORGANISM: artificial sequence
<220> FEATURE:
<223> OTHER INFORMATION: Synthetic

<400> SEQUENCE: 45
gagtgtggca gtacgcttct                                               20

<210> SEQ ID NO 46
<211> LENGTH: 20
<212> TYPE: DNA
<213> ORGANISM: artificial sequence
<220> FEATURE:
<223> OTHER INFORMATION: Synthetic

<400> SEQUENCE: 46
ctcagcagga aactctcggg                                               20

```
<210> SEQ ID NO 47
<211> LENGTH: 20
<212> TYPE: DNA
<213> ORGANISM: artificial sequence
<220> FEATURE:
<223> OTHER INFORMATION: Synthetic

<400> SEQUENCE: 47
ctgttcctct tccccagtcg                                               20

<210> SEQ ID NO 48
<211> LENGTH: 20
<212> TYPE: DNA
<213> ORGANISM: artificial sequence
<220> FEATURE:
<223> OTHER INFORMATION: Synthetic

<400> SEQUENCE: 48
cgggtatcgc ctgtattgct                                               20

<210> SEQ ID NO 49
<211> LENGTH: 20
<212> TYPE: DNA
<213> ORGANISM: artificial sequence
<220> FEATURE:
<223> OTHER INFORMATION: Synthetic

<400> SEQUENCE: 49
caaaccaatg ccagccaaca                                               20

<210> SEQ ID NO 50
<211> LENGTH: 20
<212> TYPE: DNA
<213> ORGANISM: artificial sequence
<220> FEATURE:
<223> OTHER INFORMATION: Synthetic

<400> SEQUENCE: 50
gacagcgtgg cagaaaatcc                                               20

<210> SEQ ID NO 51
<211> LENGTH: 20
<212> TYPE: DNA
<213> ORGANISM: artificial sequence
<220> FEATURE:
<223> OTHER INFORMATION: Synthetic

<400> SEQUENCE: 51
ctttggcgac cgcgttaatt                                               20

<210> SEQ ID NO 52
<211> LENGTH: 20
<212> TYPE: DNA
<213> ORGANISM: artificial sequence
<220> FEATURE:
<223> OTHER INFORMATION: Synthetic

<400> SEQUENCE: 52
aaggcccgca gttcctgcat                                               20

<210> SEQ ID NO 53
<211> LENGTH: 21
<212> TYPE: DNA
<213> ORGANISM: artificial sequence
<220> FEATURE:
<223> OTHER INFORMATION: Synthetic
```

```
<400> SEQUENCE: 53
ggcaaaccgc cgctactttt c                                              21

<210> SEQ ID NO 54
<211> LENGTH: 20
<212> TYPE: DNA
<213> ORGANISM: artificial sequence
<220> FEATURE:
<223> OTHER INFORMATION: Synthetic

<400> SEQUENCE: 54
ctgcaaggtg ccggtaaaac                                                20

<210> SEQ ID NO 55
<211> LENGTH: 20
<212> TYPE: DNA
<213> ORGANISM: artificial sequence
<220> FEATURE:
<223> OTHER INFORMATION: Synthetic

<400> SEQUENCE: 55
tcaagctgtt tgattgccgc                                                20

<210> SEQ ID NO 56
<211> LENGTH: 20
<212> TYPE: DNA
<213> ORGANISM: artificial sequence
<220> FEATURE:
<223> OTHER INFORMATION: Synthetic

<400> SEQUENCE: 56
tggcaagtca tgggatgcat                                                20

<210> SEQ ID NO 57
<211> LENGTH: 20
<212> TYPE: DNA
<213> ORGANISM: artificial sequence
<220> FEATURE:
<223> OTHER INFORMATION: Synthetic

<400> SEQUENCE: 57
aatcgtccgg tttgcaggtt                                                20

<210> SEQ ID NO 58
<211> LENGTH: 20
<212> TYPE: DNA
<213> ORGANISM: artificial sequence
<220> FEATURE:
<223> OTHER INFORMATION: Synthetic

<400> SEQUENCE: 58
ttcctgcacg gcattagtgt                                                20

<210> SEQ ID NO 59
<211> LENGTH: 20
<212> TYPE: DNA
<213> ORGANISM: artificial sequence
<220> FEATURE:
<223> OTHER INFORMATION: Synthetic

<400> SEQUENCE: 59
atcaatcgcc ccaaaccgat                                                20

<210> SEQ ID NO 60
<211> LENGTH: 20
```

```
<212> TYPE: DNA
<213> ORGANISM: artificial sequence
<220> FEATURE:
<223> OTHER INFORMATION: Synthetic

<400> SEQUENCE: 60
atctcgcgtt ctccagttgg                                              20

<210> SEQ ID NO 61
<211> LENGTH: 20
<212> TYPE: DNA
<213> ORGANISM: artificial sequence
<220> FEATURE:
<223> OTHER INFORMATION: Synthetic

<400> SEQUENCE: 61
gatcactgcg tcttcgttgc                                              20

<210> SEQ ID NO 62
<211> LENGTH: 22
<212> TYPE: DNA
<213> ORGANISM: artificial sequence
<220> FEATURE:
<223> OTHER INFORMATION: Synthetic

<400> SEQUENCE: 62
ctcttgccat cggatgtgcc ca                                           22

<210> SEQ ID NO 63
<211> LENGTH: 24
<212> TYPE: DNA
<213> ORGANISM: artificial sequence
<220> FEATURE:
<223> OTHER INFORMATION: Synthetic

<400> SEQUENCE: 63
ccagtgtggc tggtcatcct ctca                                         24

<210> SEQ ID NO 64
<211> LENGTH: 26
<212> TYPE: DNA
<213> ORGANISM: artificial sequence
<220> FEATURE:
<223> OTHER INFORMATION: Synthetic

<400> SEQUENCE: 64
gcgcacatga ggatcaccca tgtgct                                       26

<210> SEQ ID NO 65
<211> LENGTH: 237
<212> TYPE: PRT
<213> ORGANISM: artificial sequence
<220> FEATURE:
<223> OTHER INFORMATION: Synthetic

<400> SEQUENCE: 65
```

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

```
Val Pro Lys Val Ala Thr Gln Thr Val Gly Val Glu Leu Pro Val
 65                  70                  75                  80

Ala Ala Trp Arg Ser Tyr Leu Asn Met Glu Leu Thr Ile Pro Ile Phe
                 85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Ser Ala Gly Gly Gly Ser Gly Gly Gly Ser Gly Gly
130                 135                 140

Gly Gly Ser Met Asn Lys Asn Ile Asp Thr Val Arg Glu Ile Ile Thr
145                 150                 155                 160

Val Ala Ser Ile Leu Ile Lys Phe Ser Arg Glu Asp Ile Val Glu Asn
                165                 170                 175

Arg Ala Asn Phe Ile Ala Phe Leu Asn Glu Ile Gly Val Thr His Glu
            180                 185                 190

Gly Arg Lys Leu Asn Gln Asn Ser Phe Arg Lys Ile Val Ser Glu Leu
        195                 200                 205

Thr Gln Glu Asp Lys Lys Thr Leu Ile Asp Glu Phe Asn Glu Gly Phe
210                 215                 220

Glu Gly Val Tyr Arg Tyr Leu Glu Met Tyr Thr Asn Lys
225                 230                 235

<210> SEQ ID NO 66
<211> LENGTH: 11
<212> TYPE: PRT
<213> ORGANISM: artificial sequence
<220> FEATURE:
<223> OTHER INFORMATION: Synthetic

<400> SEQUENCE: 66

Ala Ala Asn Asp Glu Asn Tyr Ala Leu Ala Ala
1               5                   10

<210> SEQ ID NO 67
<211> LENGTH: 11
<212> TYPE: PRT
<213> ORGANISM: artificial sequence
<220> FEATURE:
<223> OTHER INFORMATION: Synthetic

<400> SEQUENCE: 67

Thr Cys Ala Cys Ala Cys Ala Gly Gly Ala Cys
1               5                   10

<210> SEQ ID NO 68
<211> LENGTH: 12
<212> TYPE: PRT
<213> ORGANISM: artificial sequence
<220> FEATURE:
<223> OTHER INFORMATION: Synthetic

<400> SEQUENCE: 68

Ala Ala Ala Gly Ala Gly Gly Ala Gly Ala Ala Ala
1               5                   10

<210> SEQ ID NO 69
<211> LENGTH: 165
<212> TYPE: PRT
<213> ORGANISM: artificial sequence
<220> FEATURE:
<223> OTHER INFORMATION: Synthetic
```

-continued

```
<400> SEQUENCE: 69

Gly Thr Ala Thr Ala Cys Thr Thr Thr Thr Thr Thr Ala Ala Ala
1               5                   10                  15

Gly Ala Ala Ala Ala Gly Ala Thr Thr Thr Ala Cys Ala Ala Gly Cys
            20                  25                  30

Gly Cys Ala Cys Thr Thr Thr Thr Cys Thr Thr Thr Ala Ala Thr Ala
        35                  40                  45

Thr Cys Thr Thr Ala Cys Ala Ala Thr Ala Ala Gly Thr Ala Ala
50                  55                  60

Gly Thr Thr Thr Gly Ala Ala Cys Ala Gly Gly Ala Gly Ala Ala Thr
65                  70                  75                  80

Gly Thr Ala Ala Gly Cys Cys Ala Ala Gly Cys Gly Ala Thr Gly
                85                  90                  95

Gly Cys Thr Ala Cys Gly Cys Ala Thr Thr Cys Thr Cys Thr Thr Thr
            100                 105                 110

Cys Thr Thr Thr Gly Thr Thr Ala Thr Ala Cys Thr Ala Ala Cys Ala
        115                 120                 125

Cys Cys Ala Thr Ala Thr Thr Cys Gly Ala Gly Thr Ala Gly Ala
130                 135                 140

Ala Ala Ala Thr Thr Ala Thr Thr Ala Gly Gly Ala Gly Gly Ala
145                 150                 155                 160

Thr Ala Gly Ala Thr
                165

<210> SEQ ID NO 70
<211> LENGTH: 82
<212> TYPE: PRT
<213> ORGANISM: artificial sequence
<220> FEATURE:
<223> OTHER INFORMATION: Synthetic

<400> SEQUENCE: 70

Gly Ile Asn Lys Asp Ile Glu Glu Cys Asn Ala Ile Ile Glu Gln Phe
1               5                   10                  15

Ile Asp Tyr Leu Arg Thr Gly Gln Glu Met Pro Met Glu Met Ala Asp
            20                  25                  30

Gln Ala Ile Asn Val Val Pro Gly Met Thr Pro Lys Thr Ile Leu His
        35                  40                  45

Ala Gly Pro Pro Ile Gln Pro Asp Trp Leu Lys Ser Asn Gly Phe His
    50                  55                  60

Glu Ile Glu Ala Asp Val Asn Asp Thr Ser Leu Leu Leu Ser Gly Asp
65                  70                  75                  80

Ala Ser

<210> SEQ ID NO 71
<211> LENGTH: 156
<212> TYPE: PRT
<213> ORGANISM: artificial sequence
<220> FEATURE:
<223> OTHER INFORMATION: Synthetic

<400> SEQUENCE: 71

Ala Glu Gly Ala Leu Asp Leu Ala Arg Ala Gln Asp Leu Ala Ser Ala
1               5                   10                  15

Ala Glu Lys Ala Arg Ser Ala Gly Asp Leu Cys His Ala Arg Asp Leu
            20                  25                  30
```

Leu Arg Arg Ala Leu Asp Leu Trp Asp Gly Glu Val Leu Ala Gly Val
            35                  40                  45

Pro Gly Pro Tyr Ala Gln Thr Gln Arg Val Arg Leu Gly Glu Trp Arg
    50                  55                  60

Leu Gln Leu Leu Glu Thr Arg Leu Asp Met Asp Leu Asp Gln Gly Cys
65                  70                  75                  80

His Ala Glu Ala Val Ser Glu Leu Thr Ala Leu Thr Ala Ala His Pro
                85                  90                  95

Leu Arg Glu Arg Leu Arg Glu Leu Leu Met Leu Ala Leu Tyr Arg Ser
            100                 105                 110

Gly Arg Gln Ala Glu Ala Leu Ala Val Tyr Ala Asp Thr Arg Arg Leu
        115                 120                 125

Leu Ala Asp Glu Leu Gly Val Asp Pro Arg Pro Gly Leu Gln Glu Leu
    130                 135                 140

Gln Gln Arg Ile Leu Gln Ala Asp Pro Ala Leu Ala
145                 150                 155

<210> SEQ ID NO 72
<211> LENGTH: 156
<212> TYPE: PRT
<213> ORGANISM: artificial sequence
<220> FEATURE:
<223> OTHER INFORMATION: Synthetic

<400> SEQUENCE: 72

Pro Pro Ser Thr Val Asp Val Asn Arg Phe Glu Arg Asp Ala Asp Asp
1               5                   10                  15

Gly Gln Glu Leu Leu Gln Arg Gly Asp Ala Ala Gly Gly Thr Lys Leu
            20                  25                  30

Gly His Ala Leu Ala Leu Trp Arg Gly Pro Ala Leu Ala Asp Val Val
        35                  40                  45

Ala Ser Gly Arg Leu Phe Ser Tyr Val Thr Arg Leu Glu Glu Leu Arg
    50                  55                  60

Phe Arg Ile Leu Glu Leu Arg Ile Glu Ala Asp Leu Ala Thr Gly Arg
65                  70                  75                  80

His Arg Glu Leu Val Ser Glu Leu Lys Ser Leu Val Leu Ala His Pro
                85                  90                  95

Leu His Glu His Leu His Gly Leu Leu Met Leu Ala Leu His Arg Ser
            100                 105                 110

Gly Arg Pro His Glu Ala Leu Glu Val Tyr Arg Ser Val Arg His Lys
        115                 120                 125

Met Ile Glu Asp Leu Ala Leu Glu Pro Ala Gln Asp Phe Ala Thr Leu
    130                 135                 140

His His Thr Leu Leu Ser Asp Ser Pro Pro Glu Ala
145                 150                 155

<210> SEQ ID NO 73
<211> LENGTH: 157
<212> TYPE: PRT
<213> ORGANISM: artificial sequence
<220> FEATURE:
<223> OTHER INFORMATION: Synthetic

<400> SEQUENCE: 73

Met Gln Ala Ile Pro Met Thr Leu Arg Gly Ala Glu Lys Leu Arg Glu
1               5                   10                  15

Glu Leu Asp Phe Leu Lys Ser Val Arg Arg Pro Glu Ile Ile Ala Ala
            20                  25                  30

Ile Ala Glu Ala Arg Glu His Gly Asp Leu Lys Glu Asn Ala Glu Tyr
                35                  40                  45

His Ala Ala Arg Glu Gln Gln Gly Phe Cys Glu Gly Arg Ile Lys Asp
        50                  55                  60

Ile Glu Ala Lys Leu Ser Asn Ala Gln Val Ile Asp Val Thr Lys Met
65                  70                  75                  80

Pro Asn Asn Gly Arg Val Ile Phe Gly Ala Thr Val Thr Val Leu Asn
                85                  90                  95

Leu Asp Ser Asp Glu Glu Gln Thr Tyr Arg Ile Val Gly Asp Asp Glu
            100                 105                 110

Ala Asp Phe Lys Gln Asn Leu Ile Ser Val Asn Ser Pro Ile Ala Arg
        115                 120                 125

Gly Leu Ile Gly Lys Glu Glu Asp Val Val Ile Lys Thr Pro
130                 135                 140

Gly Gly Glu Val Glu Phe Glu Val Ile Lys Val Glu Tyr
145                 150                 155

<210> SEQ ID NO 74
<211> LENGTH: 151
<212> TYPE: PRT
<213> ORGANISM: artificial sequence
<220> FEATURE:
<223> OTHER INFORMATION: Synthetic

<400> SEQUENCE: 74

Met Gln Glu Gly Gln Asn Arg Lys Thr Ser Ser Leu Ser Ile Leu Ala
1               5                   10                  15

Ile Ala Gly Val Glu Pro Tyr Gln Glu Lys Pro Gly Glu Glu Tyr Met
            20                  25                  30

Asn Glu Ala Gln Leu Ala His Phe Arg Arg Ile Leu Glu Ala Trp Arg
        35                  40                  45

Asn Gln Leu Arg Asp Glu Val Asp Arg Thr Val Thr His Met Gln Asp
    50                  55                  60

Glu Ala Ala Asn Phe Pro Asp Pro Val Asp Arg Ala Ala Gln Glu Glu
65                  70                  75                  80

Glu Phe Ser Leu Glu Leu Arg Asn Arg Asp Arg Glu Arg Lys Leu Ile
                85                  90                  95

Lys Lys Ile Glu Lys Thr Leu Lys Lys Val Glu Asp Glu Asp Phe Gly
            100                 105                 110

Tyr Cys Glu Ser Cys Gly Val Glu Ile Gly Ile Arg Arg Leu Glu Ala
        115                 120                 125

Arg Pro Thr Ala Asp Leu Cys Ile Asp Cys Lys Thr Leu Ala Glu Ile
    130                 135                 140

Arg Glu Lys Gln Met Ala Gly
145                 150

<210> SEQ ID NO 75
<211> LENGTH: 151
<212> TYPE: PRT
<213> ORGANISM: artificial sequence
<220> FEATURE:
<223> OTHER INFORMATION: Synthetic

<400> SEQUENCE: 75

Met Gln Glu Gly Gln Asn Arg Lys Thr Ser Ser Leu Ser Ile Leu Ala
1               5                   10                  15

Ile Ala Gly Val Glu Pro Tyr Gln Glu Lys Pro Gly Glu Glu Tyr Met

```
            20                  25                  30
Asn Glu Ala Gln Leu Ala His Phe Arg Arg Ile Leu Glu Ala Trp Arg
            35                  40                  45

Asn Gln Leu Arg Asp Glu Val Asp Arg Thr Val Thr His Met Gln Asp
        50                  55                  60

Glu Ala Ala Asn Phe Pro Asp Pro Val Asp Arg Ala Ala Gln Glu Glu
65                  70                  75                  80

Glu Phe Ser Leu Glu Leu Arg Asn Arg Asp Arg Glu Arg Lys Leu Ile
                85                  90                  95

Lys Lys Ile Glu Lys Thr Leu Lys Lys Val Glu Asp Glu Asp Phe Gly
            100                 105                 110

Tyr Cys Glu Ser Cys Gly Val Glu Ile Gly Ile Arg Arg Leu Glu Ala
            115                 120                 125

Arg Pro Thr Ala Asp Leu Cys Ile Asp Cys Lys Thr Leu Ala Glu Ile
        130                 135                 140

Arg Glu Lys Gln Met Ala Gly
145                 150

<210> SEQ ID NO 76
<211> LENGTH: 151
<212> TYPE: PRT
<213> ORGANISM: artificial sequence
<220> FEATURE:
<223> OTHER INFORMATION: Synthetic

<400> SEQUENCE: 76

Met Gln Glu Gly Gln Asn Arg Lys Thr Ser Ser Leu Ser Ile Leu Ala
1               5                   10                  15

Ile Ala Gly Val Glu Pro Tyr Gln Glu Lys Pro Gly Glu Glu Tyr Met
            20                  25                  30

Asn Glu Ala Gln Leu Ala His Phe Arg Arg Ile Leu Glu Ala Trp Arg
            35                  40                  45

Asn Gln Leu Arg Asp Glu Val Asp Arg Thr Val Thr His Met Gln Asp
        50                  55                  60

Glu Ala Ala Asn Phe Pro Asp Pro Val Asp Arg Ala Ala Gln Glu Glu
65                  70                  75                  80

Glu Phe Ser Leu Glu Leu Arg Asn Arg Asp Arg Glu Arg Lys Leu Ile
                85                  90                  95

Lys Lys Ile Glu Lys Thr Leu Lys Lys Val Glu Asp Glu Asp Phe Gly
            100                 105                 110

Tyr Cys Glu Ser Cys Gly Val Glu Ile Gly Ile Arg Arg Leu Glu Ala
            115                 120                 125

Arg Pro Thr Ala Asp Leu Cys Ile Asp Cys Lys Thr Leu Ala Glu Ile
        130                 135                 140

Arg Glu Lys Gln Met Ala Gly
145                 150

<210> SEQ ID NO 77
<211> LENGTH: 107
<212> TYPE: PRT
<213> ORGANISM: artificial sequence
<220> FEATURE:
<223> OTHER INFORMATION: Synthetic

<400> SEQUENCE: 77

Met Ser His Gln Lys Ile Ile Gln Asp Leu Ile Ala Trp Ile Asp Glu
1               5                   10                  15
```

His Ile Asp Gln Pro Leu Asn Ile Asp Val Ala Lys Lys Ser Ala
            20                  25                  30

Tyr Ser Lys Trp Tyr Leu Gln Arg Met Phe Arg Thr Val Thr His Gln
        35                  40                  45

Thr Leu Gly Asp Tyr Ile Arg Gln Arg Leu Leu Leu Ala Ala Val
    50                  55                  60

Glu Leu Arg Thr Thr Glu Arg Pro Ile Phe Asp Ile Ala Met Asp Leu
65              70                  75                  80

Gly Tyr Val Ser Gln Gln Thr Phe Ser Arg Val Phe Arg Gln Phe
            85                  90                  95

Asp Arg Thr Pro Ser Asp Tyr Arg His Arg Leu
            100                 105

<210> SEQ ID NO 78
<211> LENGTH: 265
<212> TYPE: PRT
<213> ORGANISM: artificial sequence
<220> FEATURE:
<223> OTHER INFORMATION: Synthetic

<400> SEQUENCE: 78

Met Ser Asn Leu Phe Gly Asn Leu Ala Gly Gln Ala Ala Lys Ala Glu
1               5                   10                  15

Lys Ala Thr Asp Asn Leu Gly Gly Phe Gly Ala Lys Glu Ser Asp
            20                  25                  30

Ile Tyr Leu Ala Thr Leu Lys Val Ala Tyr Ala Gly Lys Ala Ala Ser
        35                  40                  45

Gly Ala Asn Phe Ile Gln Ile Ala Asp Leu Thr Asp Leu Asp Gly
    50                  55                  60

His Ser Ala Gly Glu Tyr Arg Glu Gln Leu Tyr Ile Thr Ser Gly Thr
65              70                  75                  80

Glu Lys Gly Cys Lys Cys Thr Tyr Glu Lys Asn Gly Lys Glu Tyr Phe
            85                  90                  95

Leu Pro Gly Tyr Thr Val Ile Asn Asp Ile Leu Val Met Thr Ser Gly
            100                 105                 110

Glu Thr Ile Pro Glu Ala Val Phe Glu Glu Lys Val Val Asn Val Tyr
            115                 120                 125

Asp Phe Asp Glu Lys Lys Glu Val Ala Lys Ser Val Met Val Pro Val
130             135                 140

Asn Ala Ile Gly Gly Lys Phe Ala Val Ala Ile Leu Lys Ser Glu Glu
145             150                 155                 160

Asp Lys Gln Thr Lys Asp Gly Ser Gly Asn Tyr Val Ser Thr Gly Glu
            165                 170                 175

Thr Arg Phe Thr Asn Thr Ile Glu Lys Val Phe His Pro Asp Leu His
            180                 185                 190

Leu Thr Val Val Glu Ala Glu Glu Leu Thr Glu Arg Gly Lys Glu Leu
        195                 200                 205

Thr Val Glu Glu Ala Val Phe Trp Asp Lys Trp Leu Glu Lys Asn Lys
    210                 215                 220

Gly Val Thr Arg Asp Lys Thr Thr Lys Gly Gly Ala Ser Gly Lys Ala
225             230                 235                 240

Gly Gln Pro Pro Lys Pro Gly Ala Thr Asn Thr Gly Ala Gly Ala Ser
            245                 250                 255

Ala Ala Lys Ser Leu Phe Gly Lys Lys
            260                 265

<210> SEQ ID NO 79
<211> LENGTH: 166
<212> TYPE: PRT
<213> ORGANISM: artificial sequence
<220> FEATURE:
<223> OTHER INFORMATION: Synthetic

<400> SEQUENCE: 79

```
Asp Leu Gly Asn Ala Val Val Asn Ser Asn Ile Gly Val Leu Ile Lys
1               5                   10                  15

Lys Gly Leu Val Glu Lys Ser Gly Asp Gly Leu Ile Ile Thr Gly Glu
            20                  25                  30

Ala Gln Asp Ile Ile Ser Asn Ala Ala Thr Leu Tyr Ala Gln Glu Asn
        35                  40                  45

Ala Pro Glu Leu Leu Lys Lys Arg Ala Thr Arg Lys Ala Arg Glu Ile
    50                  55                  60

Thr Ser Asp Met Glu Glu Asp Lys Asp Leu Met Leu Lys Leu Leu Asp
65                  70                  75                  80

Lys Asn Gly Phe Val Leu Lys Lys Val Glu Ile Tyr Arg Ser Asn Tyr
                85                  90                  95

Leu Ala Ile Leu Glu Lys Arg Thr Asn Gly Ile Arg Asn Phe Glu Ile
            100                 105                 110

Asn Asn Asn Gly Asn Met Arg Ile Phe Gly Tyr Lys Met Met Glu His
        115                 120                 125

His Ile Gln Lys Phe Thr Asp Ile Gly Met Ser Cys Lys Ile Ala Lys
    130                 135                 140

Asn Gly Asn Val Tyr Leu Asp Ile Lys Arg Ser Ala Glu Asn Ile Glu
145                 150                 155                 160

Ala Val Ile Thr Val Ala
                165
```

<210> SEQ ID NO 80
<211> LENGTH: 90
<212> TYPE: PRT
<213> ORGANISM: artificial sequence
<220> FEATURE:
<223> OTHER INFORMATION: Synthetic

<400> SEQUENCE: 80

```
Met Asn Lys Asn Ile Asp Thr Val Arg Glu Ile Thr Val Ala Ser
1               5                   10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Val Ser Glu Leu Thr Gln Glu
    50                  55                  60

Asp Lys Lys Thr Leu Ile Asp Glu Phe Asn Glu Gly Phe Glu Gly Val
65                  70                  75                  80

Tyr Arg Tyr Leu Glu Met Tyr Thr Asn Lys
                85                  90
```

<210> SEQ ID NO 81
<211> LENGTH: 91
<212> TYPE: PRT
<213> ORGANISM: artificial sequence
<220> FEATURE:
<223> OTHER INFORMATION: Synthetic

<400> SEQUENCE: 81

Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Gln Ala Ala Glu Leu
65                  70                  75                  80

Gln Ala Val Thr Ala Ile Ala Glu Gly Arg Arg
                85                  90

<210> SEQ ID NO 82
<211> LENGTH: 12
<212> TYPE: PRT
<213> ORGANISM: artificial sequence
<220> FEATURE:
<223> OTHER INFORMATION: Synthetic

<400> SEQUENCE: 82

Asn Gln Asn Ser Phe Arg Lys Ile Val Ser Glu Leu
1               5                   10

<210> SEQ ID NO 83
<211> LENGTH: 12
<212> TYPE: PRT
<213> ORGANISM: artificial sequence
<220> FEATURE:
<223> OTHER INFORMATION: Synthetic

<400> SEQUENCE: 83

Asn Arg Asn Ser Phe Arg Lys Ile Ile Ser Lys Leu
1               5                   10

<210> SEQ ID NO 84
<211> LENGTH: 12
<212> TYPE: PRT
<213> ORGANISM: artificial sequence
<220> FEATURE:
<223> OTHER INFORMATION: Synthetic

<400> SEQUENCE: 84

Asn Gln Asn Ser Phe Arg Lys Leu Ile Thr Asn Leu
1               5                   10

<210> SEQ ID NO 85
<211> LENGTH: 12
<212> TYPE: PRT
<213> ORGANISM: artificial sequence
<220> FEATURE:
<223> OTHER INFORMATION: Synthetic

<400> SEQUENCE: 85

Asn Gln Gly Ser Phe Arg Lys Leu Ile Ser Glu Leu
1               5                   10

<210> SEQ ID NO 86
<211> LENGTH: 11
<212> TYPE: PRT
<213> ORGANISM: artificial sequence
<220> FEATURE:
<223> OTHER INFORMATION: Synthetic

<400> SEQUENCE: 86

Asn Gly Val Ser Phe Asn Lys Leu Phe Asp Leu
1               5                   10

<210> SEQ ID NO 87
<211> LENGTH: 12
<212> TYPE: PRT
<213> ORGANISM: artificial sequence
<220> FEATURE:
<223> OTHER INFORMATION: Synthetic

<400> SEQUENCE: 87

Asn Val Ala Ser Phe Lys Lys Met Ile Lys Glu Leu
1               5                   10

<210> SEQ ID NO 88
<211> LENGTH: 12
<212> TYPE: PRT
<213> ORGANISM: artificial sequence
<220> FEATURE:
<223> OTHER INFORMATION: Synthetic

<400> SEQUENCE: 88

Asn Ser Ala Asn Phe Arg Lys Met Val Ala Glu Leu
1               5                   10

<210> SEQ ID NO 89
<211> LENGTH: 12
<212> TYPE: PRT
<213> ORGANISM: artificial sequence
<220> FEATURE:
<223> OTHER INFORMATION: Synthetic

<400> SEQUENCE: 89

Thr Val Gly Asn Phe Arg Gln Val Met Thr Glu Leu
1               5                   10

<210> SEQ ID NO 90
<211> LENGTH: 12
<212> TYPE: PRT
<213> ORGANISM: artificial sequence
<220> FEATURE:
<223> OTHER INFORMATION: Synthetic

<400> SEQUENCE: 90

Thr Arg Ala Gly Phe Arg Gln Met Met Lys Arg Leu
1               5                   10

<210> SEQ ID NO 91
<211> LENGTH: 12
<212> TYPE: PRT
<213> ORGANISM: artificial sequence
<220> FEATURE:
<223> OTHER INFORMATION: Synthetic

<400> SEQUENCE: 91

Asn Lys Ser Asn Leu Lys Ser Leu Val Lys Ser Leu
1               5                   10

<210> SEQ ID NO 92
<211> LENGTH: 12
<212> TYPE: PRT
<213> ORGANISM: artificial sequence
<220> FEATURE:
<223> OTHER INFORMATION: Synthetic

```
<400> SEQUENCE: 92

Ser Lys Val Asn Met Ala Thr Leu Phe Glu Arg Met
1               5                   10

<210> SEQ ID NO 93
<211> LENGTH: 12
<212> TYPE: PRT
<213> ORGANISM: artificial sequence
<220> FEATURE:
<223> OTHER INFORMATION: Synthetic

<400> SEQUENCE: 93

Ser Lys Met Ser Phe Arg Lys Met Trp Glu Arg Leu
1               5                   10

<210> SEQ ID NO 94
<211> LENGTH: 11
<212> TYPE: PRT
<213> ORGANISM: artificial sequence
<220> FEATURE:
<223> OTHER INFORMATION: Synthetic

<400> SEQUENCE: 94

Asn Lys Tyr Arg Leu Lys Arg Met Phe Phe Asn
1               5                   10

<210> SEQ ID NO 95
<211> LENGTH: 90
<212> TYPE: PRT
<213> ORGANISM: artificial sequence
<220> FEATURE:
<223> OTHER INFORMATION: Synthetic

<400> SEQUENCE: 95

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Ile Ser Lys Leu Thr Gln Glu
    50                  55                  60

Asp Lys Lys Thr Leu Ile Asp Glu Phe Asn Gly Gly Phe Glu Gly Val
65                  70                  75                  80

Tyr Arg Tyr Leu Glu Met Tyr Thr Asn Lys
                85                  90

<210> SEQ ID NO 96
<211> LENGTH: 90
<212> TYPE: PRT
<213> ORGANISM: artificial sequence
<220> FEATURE:
<223> OTHER INFORMATION: Synthetic

<400> SEQUENCE: 96

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Arg Asn Ser Phe Arg Lys Ile Ile Ser Lys Leu Thr Gln Glu
```

-continued

```
                50                  55                  60
Asp Lys Lys Thr Leu Ile Asp Glu Phe Asn Glu Gly Phe Glu Gly Val
 65                  70                  75                  80

Tyr Arg Tyr Leu Glu Met Tyr Thr Asn Lys
                 85                  90
```

PROGRAMMABLE AND PORTABLE CRISPR-CAS TRANSCRIPTIONAL ACTIVATION IN BACTERIA

CROSS-REFERENCE TO RELATED APPLICATIONS

This application claims the benefit of U.S. Provisional Application No. 62/956,487, filed Jan. 2, 2020, the entire contents of which is incorporated herein by reference.

FIELD

The present invention relates to components, systems, and methods transcriptional modification (e.g., transcriptional activation).

BACKGROUND

Transcriptional regulation governs almost every cellular process fundamental to life. In response to cellular or external signals, transcription factors (TFs) in the cell interact with specific DNA sequences to mediate gene activation or repression. A potential path for cellular engineering therefore is the rewiring of transcriptional factors to alter gene regulatory networks. Programmable transcriptional activation and repression in principle offers on-demand control of specific biological processes without the need to permanently alter the genome of a cell. As such, significant past efforts have been devoted to developing synthetic transcription activators by fusing DNA-binding proteins with transcription effector domains to recruit the RNA polymerase (RNAP) complex. Unfortunately, these past synthetic TFs generally recognize only predefined DNA sequences and are difficult to reprogram to target other sequences, which greatly limits their utility for transcriptional regulation of diverse endogenous and engineered gene regulatory networks.

With the recent discovery of new DNA-binding proteins such as Zinc-finger TFs, transcription activator-like (TAL) effectors and CRISPR-Cas systems, there are now opportunities to develop next-generation synthetic transcription factors with greater activity and programmability. The Cas9 protein, a member of a large class of RNA-guided DNA nucleases, has emerged over the past several years as a promising system for building synthetic TFs. Cas9 utilizes a short guide RNA (gRNA) and a protospacer adjacent motif (PAM) sequence on the target DNA to bind a defined sequence based on RNA-DNA basepairing and for cleavage of the target DNA sequence. Inactivating Cas9 by mutating the catalytic residues in the nuclease domains results in a dead Cas9 (dCas9) that functions solely as a DNA-binding protein. Transcriptional effectors such as activation or repression domains can then be linked to different parts of the dCas9 complex (e.g., dCas9 or gRNA) to enable programmable and targeted transcriptional repression (e.g., CRISPRi) or activation (e.g., CRISPRa). While a variety of CRISPRi systems have been successfully demonstrated in bacteria and eukaryotes and many mammalian CRISPRa approaches exist, far fewer successful examples of bacterial CRISPRa have been shown.

In bacteria, sigma factors play a pivotal role in transcriptional initiation machinery. Sigma factors interact with the core RNAP enzyme ($\alpha 2\beta\beta'\omega$) complex and bind to specific promoter sequences. Different types of sigma factors compete for the common pool of core enzymes in bacterial cells and recruit them to corresponding promoters. Transcription factors further function in trans on the holoenzyme and regulating gene expression. Transcription activators usually bind with specific components of the RNAP complex and direct the complex to the target promoter region. However, most transcriptional activation domains in bacteria are not well-characterized and have not been demonstrated to mediate transcriptional activation when coupled synthetically with DNA binding domains. Only a few efforts have been described for engineering bacterial transcriptional activation using CRISPR-Cas. In one study, dCas9 was fused to the RNAP $\omega$ subunit, which interacts with the RNA polymerase to mediate gene activation. However, this CRISPRa system could only function in the $\omega$ subunit knockout background. Deletion of rpoZ that encodes $\omega$ subunit is known to lead to altered basal transcription profile and fitness defects. Another study used bacterial enhancer binding proteins (bEBPs) as the fused activation domain in a similar approach, but the bEBPs-mediated CRISPRa is only compatible with $\sigma 54$ promoters and the deletion of endogenous bEBPs is required. Both systems require modification of the bacterial genome, which limits the portability to genetically tractable microbes. Another study used a scaffold RNA (scRNA) containing the gRNA and a MS2 domain, which could bind to a MCP-fused transcription factor SoxS to enable dCas9-mediated transcriptional activation. This system exhibited higher activity after further optimization but has a narrow targetable region within the promoters. Furthermore, most of these prior studies have only demonstrated CRISPRa in laboratory E. coli strains and activity in other bacteria is unknown.

SUMMARY

Provided herein are systems, components, kits, and methods that facilitate transcription modification and identification of transcriptional effectors. These systems, kits, compositions, and methods employ a combination of CRISPR-Cas sequence specificity with integrases with transcriptional effectors.

Disclosed herein are systems comprising a fusion protein comprising Cas9 protein linked to a transcriptional effector (e.g., a transcriptional activator or transcriptional repressor) or variant or fragment thereof and/or a first nucleic acid encoding the fusion protein; and at least one guide RNA (gRNA) and/or at least one second nucleic acid encoding the guide RNA sequence, wherein the at least one guide gRNA is complementary to a target DNA sequence. In some embodiments, the system further comprises at least one reporter gene and/or at least one third nucleic acid encoding the reporter gene. In some embodiments, the first nucleic acid, the at least one second nucleic acid, and the at least one third nucleic acid are on a single vector or different vectors. In some embodiments, the system is in a bacterial cell. In some embodiments, the system is a cell free system.

In some embodiments, the transcriptional effector is linked to the C-terminal end of the Cas9 protein. In some embodiments, the fusion protein further comprises a linker between the Cas9 protein and the transcriptional effector. In some embodiments, the linker comprises an amino acid sequence of SEQ ID NO:1 or SEQ ID NO:2. In some embodiments, the Cas9 protein is a catalytically-dead Cas9 (dCas9).

In some embodiments, the transcriptional effector is a transcriptional activator. In some embodiments, the transcriptional effector comprises AsiA (Audrey Stevens' inhibitor A), or a fragment or variant thereof. In some embodiments, the transcriptional effector comprises an amino acid sequence of SEQ ID NO: 80. In some embodiments, the transcriptional effector comprises an amino acid sequence of SEQ ID NO: 80 with a Q51R, V58I, or E60K mutation, or any combination thereof. In some embodiments, the transcriptional effector comprises an amino acid sequence of SEQ ID NO:95 or SEQ ID NO: 96.

In some embodiments, the target DNA sequence is upstream the reporter gene transcription start site. In some embodiments, the target DNA sequence is a DNA sequence in a host cell. In some embodiments, the host cell is a bacterial cell. In some embodiments, the target DNA sequence comprises DNA endogenous or exogenous to the host cell. In some embodiments, the exogenous DNA is on a plasmid or stably integrated into genome of the host cell. In some embodiments, the target DNA sequence is upstream or in proximity to a target gene.

Also disclosed herein is a fusion protein comprising a transcriptional effector (e.g., a transcriptional activator or transcriptional repressor), or variant or fragment thereof, linked to the C-terminal end of a Cas9 protein. In some embodiments, the transcriptional effector is linked to the C-terminal end of the Cas9 protein. In some embodiments, the fusion protein further comprises a linker between the Cas9 protein and the transcriptional effector. In some embodiments, the linker comprises an amino acid sequence of SEQ ID NO:1 or SEQ ID NO:2. In some embodiments, the Cas9 protein is a catalytically-dead Cas9 (dCas9). In some embodiments, the transcriptional effector comprises AsiA, or a fragment or variant thereof. In some embodiments, the transcriptional effector comprises an amino acid sequence of SEQ ID NO: 80. In some embodiments, the transcriptional effector comprises an amino acid sequence of SEQ ID NO: 80 with a Q51R, V58I, or E60K mutation, or any combination thereof. In some embodiments, the transcriptional effector comprises an amino acid sequence of SEQ ID NO:95 or SEQ ID NO: 96. Also disclosed, is a nucleic acid (e.g., a plasmid) encoding the fusion protein. As well, a bacterial cell comprising the system, the fusion protein, or the nucleic acid is disclosed.

Further disclosed are methods of altering transcription of a target gene in bacteria, comprising introducing the system disclosed herein into bacteria comprising a target DNA sequence. In some embodiments, the target DNA sequence comprises DNA endogenous or exogenous to the bacteria. In some embodiments, the exogenous DNA is on a plasmid or stably integrated into genome of the bacteria. In some embodiments, the target DNA sequence is upstream or proximal to the target gene.

Additionally disclosed are methods for screening for or identifying a putative transcriptional effector, comprising: introducing into a bacterial host cell: a plurality of putative transcriptional effectors linked to a Cas9 protein or a first nucleic acid encoding a putative transcriptional effector linked to a Cas9 protein; at least one guide RNA (gRNA) and/or at least one second nucleic acid encoding the at least one guide RNA sequence, wherein the at least one gRNA is complementary to a target DNA sequence; and a third nucleic acid comprising the target DNA sequence adjacent to at least one reporter gene encoding a gene product; measuring the presence or relative quantity of the gene product in the bacterial host cell; isolating bacterial host cells showing a change in quantity of the gene product relative to those host cells lacking the putative transcriptional effector or the gRNA; and identifying the putative transcriptional effector by isolating DNA and/or RNA from the isolated bacterial host cells and sequencing the isolated DNA and/or RNA. In some embodiments, the first nucleic acid, the at least one second nucleic acid, and the at least one third nucleic acid are different vectors.

The methods may further comprise mutating the putative transcriptional effector to create a library of mutant transcriptional effectors and repeating the method with the library of mutant transcriptional effectors.

In some embodiments, the transcriptional effector is linked to the C-terminal end of the Cas9 protein. In some embodiments, the fusion protein further comprises a linker between the Cas9 protein and the transcriptional effector. In some embodiments, the linker comprises an amino acid sequence of SEQ ID NO:1 or SEQ ID NO:2. In some embodiments, the Cas9 protein is a catalytically-dead Cas9 (dCas9).

In some embodiments, the reporter gene encodes a fluorescent protein, a selection marker, or a combination thereof. In some embodiments, the selection marker comprises a degradation tag. In some embodiments, the degradation tag comprises an amino acid sequence of SEQ ID NO: 66.

Kits comprising any or all of the components of the systems described herein are also provided.

Other aspects and embodiments of the disclosure will be apparent in light of the following detailed description.

BRIEF DESCRIPTION OF THE DRAWINGS

FIG. 1A is a schematic of an exemplary strategy for bacterial CRISPRa using a dCas9 fused with a transcriptional activator, a targeting gRNA, and reporter genes. FIG. 1B is a schematic of system components constructed in three compatible plasmids and validation methods. CasTA candidates could be cross validated through GFP and antibiotic resistance gene reporters. FIG. 1C is a graph of the fold activation of CasTA candidates using different gRNAs targeting to different locations of the GFP reporter gene compared to a strain without CasTA. FIG. 1D is a graph of the survival of cells containing upregulated antibiotic resistance reporter induced by dCas9 or dCas9-AisA with gRNA-H3 under kanamycin selection (2.5 µg/ml). FIG. 1E is a graph the fold activation of different gRNAs paired with dCas9-AsiA and dCas9-ω to profile the optimal gRNA binding distance. FIG. 1F is a graph comparing single and multiple gRNA with dCas9-AsiA. Data in all panels are 3-5 biological replicates with +/− standard error of mean (SEM).

FIG. 2A is a schematic of two rounds of directed evolution to improve potency of dCas9-AsiA. Pie charts show frequencies of dCas9-AsiA variants identified from each round. FIG. 2B is a schematic of the mutations found in enriched AsiA variants, and their positions along the Asia secondary structure (left) and the crystal structure of wild-type AsiA (blue) interfaced with region 4 of σ70 (orange) (right). Mutations from the original linker sequence, SAGGGGSGGGGS (SEQ ID NO: 1), to CAGGGGSGGGGS (SEQ ID NO: 2), were also seen in m1.1, m1.3, and m2.1. FIG. 2C are graphs of the distribution of fluorescence signal of the GFP reporter induced by different dCas9-AsiA variants (top) and fold induction by different dCas9-AsiA variants is shown (bottom). FIG. 2D is a graph of CRISPRa induction of promoters with varying basal expression levels. CRISPRa−, basal expression of the promoter; CRISPRa+, expression activated by dCas9-AsiA-m2.1 and associated gRNAs. Data shown are 3 biological replicates with +/−SEM.

FIG. 3A is a graph of fluorescence showing CasTA2.1 upregulated a genomically inserted GFP reporter. FIG. 3B is a graph of chromosomal gene targets activated by CasTA2.1 with bars showing the activation fold change and dots showing basal expression of each gene. FIG. 2C is a graph showing CasTA2.1 mediated CRISPRi with appropriate gRNA designs by positioning different gRNAs relative to the target gene. A non-specific gRNA was used as the negative control. FIG. 3D demonstrates multiplexed CRISPRa and CRISPRi using CasTA2.1 on a reporter containing GFP and mScarlet. Parental cells had low basal GFP and high basal mScarlet expression. Data shown are 3-4 biological replicates with +/−SEM.

FIG. 4A is a schematic of construction and screening platform to characterize a library of CRISPRa-mediated inducible promoters by targeted RNAseq and DNAseq. FIG. 4B are scatter plots of promoters significantly activated by CasTA2.1 using gRNA-H23 (left) or gRNA-H22 (right) plotted with basal expression level on x-axis against fold activation by CRISPRa on y-axis. N is the total number of promoters shown. Red box corresponds to highly activated promoters (fold change >10). FIG. 4C is a graph of highly activated promoters (>10 fold) using gRNA-H23 (left) or gRNA-H22 (right) basal expression levels (purple lines), induced expression level (orange lines on left or red lines on right, activated with gRNA-H23 or gRNA-H22, respectively) and induced fold changes (gray bars) are shown.

FIGS. 5A-5C show evolved CasTA functions in multiple bacterial species. FIG. 5A is a multiple sequence alignment of AsiA homologs from different phage genomes at residue positions 50-61. Highlighted red residues indicate positions that are mutated in AsiAm2.1. FIG. 5B are graphs of CRISPRi in *S. enterica* and *K. oxytoca* using CasTA2.1. FIG. 5C are graphs of CRISPRa in *S. enterica* and *K. oxytoca* using CasTA1.0 (dCas9-AsiA_wt), CasTA2.1 (dCas9-AsiA_m2.1) or ancestral strain with basal promoter expression (none). All data are 3-4 biological replicates with +/−SEM. *Student's t-test, p<0.0001 NS non-significant.

FIG. 7A is growth curves of *E. coli* containing 01E134 on LB media supplemented with different spectinomycin concentrations. Dotted line indicates growth phase when cell density was measured in other panels. FIG. 7B is the election stringency of different antibiotics using corresponding resistance genes as selection reporters (01E134-37). KanR-ssrA: Kan resistance gene (KanR) with degradation tag (AANDENYALAA (SEQ ID NO: 66)). Heat map corresponds to cell density after 14 hrs. Purple dotted outline corresponds to the antibiotic concentration used for sufficiently stringent selection. For SpecR, 1× Spectinomycin=50 µg/ml. For BleoR, 1× Bleocin=5 µg/ml. For KanR, 1× Kanamycin=50 µg/ml. FIG. 7C is the selection stringency of KanR-ssrA (x-axis) and BleoR (y-axis) dual reporter with double antibiotic selection of Kanamycin (Kan) and Bleocin (Bleo). Purple dotted outline corresponds to the antibiotic concentration used for sufficiently stringent selection. FIG. 7D is a graph of the escape rates of using KanR-ssrA alone or KanR-ssrA and BleoR as selection reporters. Data are 3 biological replicates in each experiment. Error bars are S.E.M.

FIG. 10A is a graph of the transcriptional activation of a weak promoter (J23117) of a GFP reporter using different gRNAs with dCas9-AsiA wild-type (wt) or mutant (m2.1). dCas9-AsiA_m2.1 (blue circles) had similar optimal gRNA targeting distance (~−200 bp from TSS) as dCas9-AsiA_wt (brown squares). FIG. 10B is a graph of the transcriptional activation using dCas9-AsiA_m2.1 with different gRNAs against a medium basal strength promoter (J23116; red circles) or strong basal strength promoter (J23110; orange circles). Induction range was found to be higher for the medium promoter than the strong promoter due to saturating absolute induction level for both promoters. FIG. 10C is a graph showing increasing ribosomal binding site (RBS) strength with and without transcriptional induction (+/−aTc) of dCas9-AsiA wild-type (wt) or mutant (m2.1) generally increased fluorescence signal of reporter gene. Weak RBS (BBa_B0033), strong RBS (BBa_B0034). Mean from three biological replicates are plotted with errorbars as +/−S.E.M. FIG. 10D is a graph of different gRNAs targeting all NGG sites across the weak promoter (J23117) paired with dCas9-AsiA_m2.1 to profile the optimal gRNA binding distance. The same gRNAs (H3 to H5) as used in FIG. 1 were labeled.

FIG. 12A is a graph of the transcriptomic profile of cells expressing dCas9-AsiA_wt using an optimal gRNA (gRNA-H4) targeting a GFP reporter gene on pWJ89 (x-axis) versus cells expressing dCas9-AsiA_m2.1 and the same gRNA (y-axis). FIG. 12B is a graph of the transcriptomic profile of parental GFP control (pWJ89) cells (x-axis) versus cells expressing dCas9-AsiA_m2.1 and gRNA-H4 (y-axis). FIG. 12C is a graph of the transcriptomic profile of parental GFP control cells (x-axis) versus with cells overexpressing dCas9-AsiA_m2.1 and gRNA-H4 (y-axis). Genes with more than 30 fold up-regulation under dCas9-AsiA_m2.1 over-expression are highlighted in red and grouped by their annotated sigma factors. Heatmap on the right indicates the ratios of highly activated (fold change >30) promoters within each group of promoters mediated by different sigma factors.

FIG. 13A is an exemplary schematic for using CRISPRa on a metagenomic promoter library (RS7003) to mine CasTA-inducible promoters using targeted DNAseq and targeted RNAseq. FIG. 13B is volcano plots of CasTA-mediated activation using two different gRNAs (gRNA-H22 and gRNA-H23) of the same promoter library, with each point in the plot corresponding to a unique promoter. Significantly activated promoters (p<0.05) are highlighted with the red rectangle, and the numbers of activated promoters are indicated. Data were calculated from 4 biological experiments. FIG. 13C is a graph of the percentage of highly activated promoters (fold change >10) among all promoters of each bacterial genius. Numbers in the bars indicate the actual numbers of highly activated promoters. Dendrogram represents the phylogenic distance between each group.

DETAILED DESCRIPTION

Figure 1A:
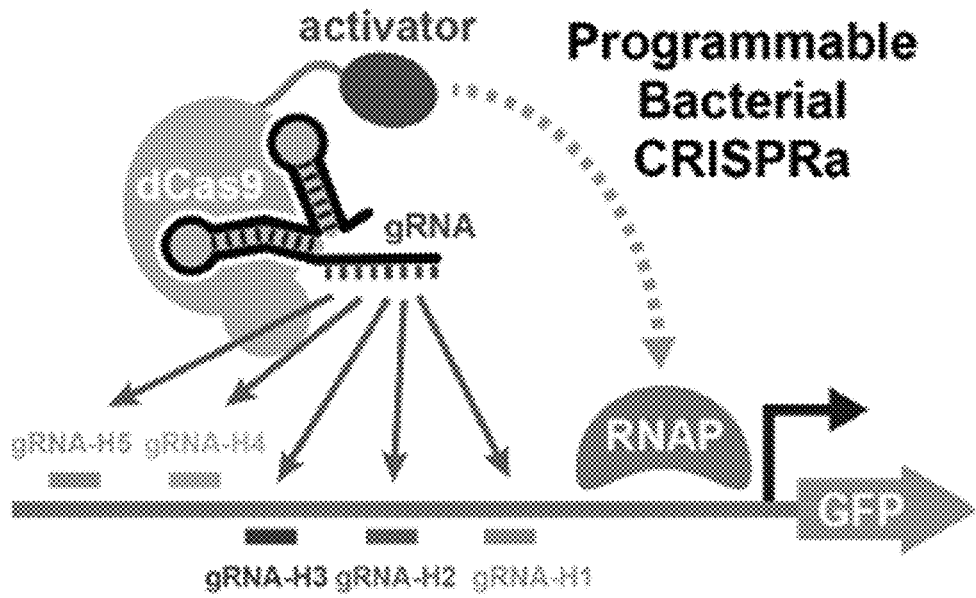
FIGS. 1A-1F show a high-throughput platform to identify and engineer bacterial CRISPR-Cas transcription activators (CasTAs).

The disclosed systems, components, kits, and methods provides methods for transcriptional modification and identification of transcriptional effectors. Disclosed herein is a high-throughput platform to screen and select for bacterial CRISPR-Cas transcriptional modifiers, e.g., bacterial CRISPR-Cas transcriptional activators (CasTAs). A number of natural bacterial and phage regulatory effectors were screened and a phage protein that induced gene activation when fused to dCas9 was identified. The targeting window of this CasTA was characterized and further rounds of directed evolution were performed using the screening platform to yield higher functioning variants, which mediated both CRISPRi and CRISPRa of genomic and plasmid targets. This activator system was applied to a metagenomic promoter library mined from diverse bacteria to build a library of CasTA-inducible promoters of varying basal and induced expression levels that are useful as a resource for the synthetic biology research community. Successful transfer of the CRISPRa system to other bacterial species of clinical and bioindustrial importance was also achieved.

Section headings as used in this section and the entire disclosure herein are merely for organizational purposes and are not intended to be limiting.

Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific, and technical terms used in connection with the present disclosure shall have the meanings that are commonly understood by those of ordinary skill in the art. For example, any nomenclature used in connection with, and techniques of cell culture, molecular biology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein, "nucleic acid" or "nucleic acid sequence" refers to a polymer or oligomer of pyrimidine and/or purine bases, preferably cytosine, thymine, and uracil, and adenine and guanine, respectively (See Albert L. Lehninger, Principles of Biochemistry, at 793-800 (Worth Pub. 1982)). The present technology contemplates any deoxyribonucleotide, ribonucleotide, or peptide nucleic acid component, and any chemical variants thereof, such as methylated, hydroxymethylated, or glycosylated forms of these bases, and the like. The polymers or oligomers may be heterogenous or homogenous in composition and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, Biochemistry, 41(14): 4503-4510 (2002)) and U.S. Pat. No. 5,034,506), locked nucleic acid (LNA; see Wahlestedt et al., Proc. Natl. Acad. Sci. U.S.A., 97: 5633-5638 (2000)), cyclohexenyl nucleic acids (see Wang, J. Am. Chem. Soc., 122: 8595-8602 (2000)), and/or a ribozyme. Hence, the term "nucleic acid" or "nucleic acid sequence" may also encompass a chain comprising non-natural nucleotides, modified nucleotides, and/or non-nucleotide building blocks that can exhibit the same function as natural nucleotides (e.g., "nucleotide analogs"); further, the term "nucleic acid sequence" as used herein refers to an oligonucleotide, nucleotide or polynucleotide, and fragments or portions thereof, and to DNA or RNA of genomic or synthetic origin, which may be single or double-stranded, and represent the sense or antisense strand. The terms "nucleic acid," "polynucleotide," "nucleotide sequence," and "oligonucleotide" are used interchangeably. They refer to a polymeric form of nucleotides of any length, either deoxyribonucleotides or ribonucleotides, or analogs thereof.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (e.g., that are identical) as between the sequence of interest and the reference sequence divided by the length of the longest sequence (e.g., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

A "vector" or "expression vector" is a replicon, such as plasmid, phage, virus, or cosmid, to which another DNA segment, e.g., an "insert," may be attached or incorporated so as to bring about the replication of the attached segment in a cell.

A cell has been "genetically modified," "transformed," or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

As used herein, the terms "providing", "administering," "introducing," are used interchangeably herein and refer to the placement of the systems of the disclosure into a cell, organism, or subject by a method or route which results in at least partial localization of the system to a desired site. The systems can be administered by any appropriate route which results in delivery to a desired location in the cell, organism, or subject.

Systems

Disclosed herein are systems comprising: a conjugate comprising Cas9 protein linked to a transcriptional effector or variant or fragment thereof and/or a first nucleic acid encoding the fusion protein; and at least one guide RNA (gRNA) and/or at least one second nucleic acid encoding the guide RNA sequence, wherein the gRNA is complementary to a target DNA sequence. In some embodiments, the system further comprises at least one reporter gene and/or at least one third nucleic acid encoding the reporter gene.

The Cas9 protein can be obtained from any suitable microorganism, and a number of bacteria express Cas9 protein orthologs or variants (see, e.g., U.S. Pat. No. 10,266, 850 incorporated herein by reference) and may be used in connection with the present disclosure. The amino acid sequences of Cas proteins from a variety of species are also publicly available through the GenBank and UniProt databases.

In some embodiments, the Cas9 protein is a catalytically-dead Cas9. Catalytically-dead Cas9 is essentially a DNA-binding protein due to, typically, two or more mutations within its catalytic nuclease domains which renders the protein with very little or no catalytic nuclease activity. For example, *Streptococcus pyogenes* Cas9 may be rendered catalytically dead by mutations of D10 and at least one of E762, H840, N854, N863, or D986, typically H840 and/or N863A (see, e.g., U.S. Pat. No. 10,266,850, incorporated herein by reference). Mutations in corresponding orthologs are known. Oftentimes, such mutations cause catalytically-dead Cas9 to possess no more than 3% of the normal nuclease activity.

The transcriptional effector may be linked to the Cas9 protein at the N or C terminus. In some embodiments, the transcriptional effector is linked to the C-terminal end of the Cas9 protein.

In some embodiments, a linker (e.g., a peptide linker) is used to link the Cas9 protein and the transcriptional effector. The linkers may comprise any amino acid sequence of any length. The linkers may be flexible such that they do not constrain either of the two components they link together in any particular orientation. The linkers may essentially act as a spacer. In select embodiments, the linker links the C-terminus of the Cas9 protein to the N-terminus of the transcriptional effector. In some embodiments, the linker comprises an amino acid sequence of SAGGGGSGGGGS (SEQ ID NO:1) or CAGGGGSGGGGS (SEQ ID NO:2).

Transcriptional effectors are proteins or protein domains that can be used to control gene expression. Transcriptional effectors may bind to and regulate promoters, promoter elements, or RNA polymerases. The transcriptional effector may be a transcriptional activator. Transcriptional activators may increase or start transcription resulting in an increased expression of a gene or gene product over time. The transcriptional effector may be a transcriptional repressor. Transcriptional repressors may decrease or stall transcription resulting in decreased expression of a gene or gene product over time.

The present system may be used with transcriptional effectors known in the art or to screen putative transcriptional effectors, as described elsewhere herein. The transcriptional effector of the present system may be selected from the group consisting of: B42 transactivation domain (B42), BTAD domain-containing protein 1 (BTAD1), BTAD domain-containing protein 2 (BTAD2), transcription elongation factor GreA (GreA), RNA polymerase-binding transcription factor DksA (DksA), regulatory protein SoxS (SoxS), N4 single stranded binding protein, Motility Protein A (MotA), 10 kDa anti-sigma factor (AsiA), omega subunit of DNA-dependent RNA polymerase (w), or a fragment or variant thereof.

In some embodiments, the transcriptional effector comprises AsiA, or a fragment or variant thereof. In some embodiments, the transcriptional effector comprises an amino acid sequence of wild-type AsiA (SEQ ID NO: 80). In select embodiments, the transcriptional effector comprises a variant of AsiA having mutations in any or all of Q51, V58, and E60 of SEQ ID NO: 80. In some embodiments, the transcriptional effector comprises an amino acid sequence of SEQ ID NO: 80 with a Q51R mutation, V58I mutation, E60K mutation, or any combination thereof. In select embodiments, the transcriptional effector comprises an amino acid sequence of SEQ ID NO:95 or SEQ ID NO: 96.

The system comprises at least one guide RNA (gRNA) and/or at least one second nucleic acid encoding the guide RNA sequence, wherein the gRNA is complementary to a target DNA. The guide RNA sequence specifies the target site with an approximate 20-nucleotide guide sequence followed by a protospacer adjacent motif (PAM) that directs Cas9 via Watson-Crick base pairing to a target sequence. The gRNA may be a non-naturally occurring gRNA.

The terms "target DNA sequence," "target nucleic acid," "target sequence," and "target site" are used interchangeably herein to refer to a polynucleotide (nucleic acid, gene, chromosome, genome, etc.) to which a guide sequence (e.g., a guide RNA) is designed to have complementarity, wherein hybridization between the target sequence and a guide sequence promotes the formation of a Cas9 complex, provided sufficient conditions for binding exist.

A general theme in transcription factor regulation of gene expression is that all that is generally required is simple association with the promoter and sufficient proximity. The distance is not very important as long as it facilitates the correct position and orientation to the promoter or the transcription start site. Thus, the target site recognized by the gRNA may be various distance from the transcription start site, in an upstream or downstream region of a target gene.

In some embodiments, the target DNA sequence is upstream of the transcription start site (TSS) of a reporter gene. The target DNA sequence may be greater than 10 base pairs, greater than 50 base pairs, greater than 100 base pairs, greater than 150 base pairs, greater than 200 base pairs, or greater than 250 base pairs upstream of the TSS. In some embodiments, the target DNA sequence is 50-300 base pairs (e.g., 50-200 base pairs, 50-100 base pairs, 100-300 base pairs, or 100-200 base pairs) upstream of the TSS. In some embodiments, the target DNA sequence is near (within 50 base pairs) of the transcription start site (TSS) of a reporter gene. In some embodiments, the target DNA sequence is within the gene body of a reporter gene.

In some embodiments, the target DNA is a DNA sequence in a host cell. In some embodiments, the target DNA sequence comprises DNA endogenous to the host cell. In some embodiments, the endogenous DNA is a genomic DNA sequence. The term "genomic," as used herein, refers to a nucleic acid sequence (e.g., a gene or locus) that is located on a chromosome in a cell. In some embodiments, the target DNA sequence comprises DNA exogenous to the host cell. DNA exogenous to the host cell is DNA which does not naturally occur in the cells, such as a transgene and recombinant DNAs. In some embodiments, the exogenous DNA is on a plasmid or stably integrated into the genome of the host cell from an exogenous source. In some embodiments, whether endogenous or exogenous, the target DNA is upstream or in proximity to a target gene encoding for a gene product. For example, in some embodiments, the target DNA is greater than 50 base pairs upstream of the transcription start site of a target gene. In some embodiments, the target DNA is less than 50 base pairs upstream of the transcription start site of a target gene. In some embodiments, the target DNA is within the gene body of the target gene. The target gene product may be any gene product endogenous to the cell or provided exogenously as described above. In some embodiments, the gene product comprises a reporter gene. In some embodiments, the host cell is a bacterial cell.

As used herein, the term "reporter gene" refers to a polynucleotide that encodes a reporter molecule that can be detected, either directly or indirectly, when expressed under control of its promoter. The reporter gene includes all the required sequence elements required for synthesis of the reporter molecule. Reporter genes facilitate the rapid analysis of a large number of cells by allowing selective measurement of the reporter gene product. Any number of reporter genes and the means of measuring or detecting the gene product of the reporter gene are known in the art. In some embodiments, the reporter gene may encode any one or combinations of fluorescent proteins, bioluminescent proteins, enzymes, antigenic epitopes, growth selection markers, and the like.

The target sequence and guide sequence need not exhibit complete complementarity, provided that there is sufficient complementarity to cause hybridization and promote binding and association with the Cas9-transcriptional effector conjugate. A target sequence may comprise any polynucleotide, such as DNA or RNA. Suitable DNA/RNA binding conditions include physiological conditions normally present in a cell. Other suitable DNA/RNA binding conditions (e.g., conditions in a cell-free system) are known in the art; see, e.g., Sambrook, referenced herein and incorporated by reference. The strand of the target DNA that is complementary to and hybridizes with the DNA-targeting RNA is referred to as the "complementary strand" and the strand of the target DNA that is complementary to the "complementary strand" (and is therefore not complementary to the DNA-targeting RNA) is referred to as the "noncomplementary strand" or "non-complementary strand."

The gRNA may be a crRNA, crRNA/tracrRNA (or single guide RNA, sgRNA). The terms "gRNA," "guide RNA" and "CRISPR guide sequence" may be used interchangeably throughout and refer to a nucleic acid comprising a sequence that determines the binding specificity of the CRISPR-Cas system. A gRNA hybridizes to (complementary to, partially or completely) a target nucleic acid sequence (e.g., the genome) in a host cell. The system may further comprise a target nucleic acid.

The gRNA or portion thereof that hybridizes to the target nucleic acid (a target site) may be between 15-40 nucleotides in length. gRNAs or sgRNA(s) can be between about 5 and 100 nucleotides long, or longer. To facilitate gRNA design, many computational tools have been developed (See Prykhozhij et al. (PLoS ONE, 10(3): (2015)); Zhu et al. (PLoS ONE, 9(9) (2014)); Xiao et al. (Bioinformatics. Jan. 21, 2014); Heigwer et al. (Nat Methods, 11(2): 122-123 (2014)). Methods and tools for guide RNA design are discussed by Zhu (Frontiers in Biology, 10 (4) pp 289-296 (2015)), which is incorporated by reference herein. Additionally, there are many publicly available software tools that can be used to facilitate the design of sgRNA(s); including but not limited to, Genscript Interactive CRISPR gRNA Design Tool, WU-CRISPR, and Broad Institute GPP sgRNA Designer. There are also publicly available predesigned gRNA sequences to target many genes and locations within the genomes of many species (human, mouse, rat, zebrafish, *C. elegans*), including but not limited to, IDT DNA Predesigned Alt-R CRISPR-Cas9 guide RNAs, Addgene Validated gRNA Target Sequences, and GenScript Genome-wide gRNA databases.

To construct cells that express the present system, expression vectors for stable or transient expression of the present system may be constructed via conventional methods and introduced into host cells. For example, nucleic acids encoding the components of the present system may be cloned into a suitable expression vector, such as a plasmid in operable linkage to a suitable promoter.

The first nucleic acid, the at least one second nucleic acid, and the at least one third nucleic acid may be provided on a single vector or different vectors. For example, each of the first nucleic acid, the at least one second nucleic acid, and the at least one third nucleic acid may be provided on a first, second and third vector (e.g., plasmid), respectively. Any of the vectors comprising a nucleic acid sequence that encodes the components of the present system is also within the scope of the present disclosure.

Conventional viral and non-viral based gene transfer methods can be used to introduce nucleic acids encoding components of the present system into cells. Non-viral vector delivery systems include DNA plasmids, cosmids, RNA (e.g., a transcript of a vector described herein), and a nucleic acid. Viral vector delivery systems include DNA and RNA viruses, which have either episomal or integrated genomes after delivery to the cell. Viral vectors include, for example, retroviral, lentiviral, adenoviral, adeno-associated and herpes simplex viral vectors. Additionally, delivery vehicles such as nanoparticle- and lipid-based mRNA or protein delivery systems can be used. Examples of delivery vehicles include ribonucleoprotein (RNP) complexes, lipid-based delivery system, gene gun, hydrodynamic, electroporation or nucleofection microinjection, and biolistics. Various gene delivery methods are discussed in detail by Nayerossadat et al. (Adv Biomed Res. 2012; 1: 27) and Ibraheem et al. (Int J Pharm. 2014 Jan. 1; 459(1-2):70-83), incorporated herein by reference.

When introduced into the host cell, the vectors may be maintained as an autonomously replicating sequence or extrachromosomal element or may be integrated into host DNA.

Promoters for the expression of the components that may be used include T7 RNA polymerase promoters, constitutive E. coli promoters, and promoters that could be broadly recognized by transcriptional machinery in a wide range of bacterial organisms. The system may be used with various bacterial hosts.

Drug selection strategies may be adopted for positively selecting for cells that underwent successful introduction into a cell or cells. Plasmids that are non-replicative, or plasmids that can be cured by high temperature may be used.

The present disclosure also provides for DNA segments encoding the proteins disclosed herein, vectors containing these segments and host cells containing the vectors. The vectors may be used to propagate the segment in an appropriate host cell and/or to allow expression from the segment (e.g., an expression vector). The person of ordinary skill in the art would be aware of the various vectors available for propagation and expression of a cloned DNA sequence. In one embodiment, a DNA segment encoding the present protein(s) is contained in a plasmid vector that allows expression of the protein(s) and subsequent isolation and purification of the protein produced by the recombinant vector. Accordingly, the proteins disclosed herein can be purified following expression, obtained by chemical synthesis, or obtained by recombinant methods.

In some embodiments, the system is a cell-free system.

Cas9-Transcription Effector Fusion Proteins

Also disclosed herein are fusion proteins comprising a Cas9 protein linked to a transcriptional effector. The Cas9 protein can be obtained from any suitable microorganism, and a number of bacteria express Cas9 protein orthologs or variants (see, e.g., U.S. Pat. No. 10,266,850 incorporated herein by reference) and may be used in connection with the present disclosure. The amino acid sequences of Cas proteins from a variety of species are also publicly available through the GenBank and UniProt databases.

In some embodiments, the Cas9 protein is a catalytically-dead Cas9. Catalytically-dead Cas9 is essentially a DNA-binding protein due to, typically, two or more mutations within its catalytic nuclease domains which renders the protein with very little or no catalytic nuclease activity. For example, Streptococcus pyogenes Cas9 may be rendered catalytically dead by mutations of D10 and at least one of E762, H840, N854, N863, or D986, typically H840 and/or N863A (see, e.g., U.S. Pat. No. 10,266,850, incorporated herein by reference). Mutations in corresponding orthologs are known. Oftentimes, such mutations cause catalytically-dead Cas9 to possess no more than 3% of the normal nuclease activity.

The transcriptional effector may be linked to the Cas9 protein at the N or C terminus. In some embodiments, the transcriptional effector is linked to the C-terminal end of the Cas9 protein. In some embodiments, a linker (e.g., a peptide linker) is used to link the Cas9 protein and the transcriptional effector. The linkers may comprise any amino acid sequence of any length. The linkers may be flexible such that they do not constrain either of the two components they link together in any particular orientation. The linkers may essentially act as a spacer. In select embodiments, the linker links the C-terminus of the Cas9 protein to the N-terminus of the transcriptional effector. In some embodiments, the linker comprises an amino acid sequence of SAGGGGSGGGGS (SEQ ID NO:1) or CAGGGGSGGGGS (SEQ ID NO:2).

The transcriptional effector may include a transcriptional activator and/or a transcriptional repressor. The transcriptional effector may be selected from the group consisting of B42 transactivation domain (B42), BTAD domain-containing protein 1 (BTAD1), BTAD domain-containing protein 2 (BTAD2), transcription elongation factor GreA (GreA), RNA polymerase-binding transcription factor DksA (DksA), regulatory protein SoxS (SoxS), N4 single stranded binding protein, Motility Protein A (MotA), 10 kDa anti-sigma factor (AsiA), omega subunit of DNA-dependent RNA polymerase (w), or a fragment or variant thereof. The transcriptional effector may be a putative transcriptional effector. The putative transcription effector may be confirmed or identified by the methods described elsewhere herein.

In some embodiments, the transcriptional effector comprises AsiA, or a fragment or variant thereof. In some embodiments, the transcriptional effector comprises an amino acid sequence of wild-type AsiA (SEQ ID NO: 80). In select embodiments, the transcriptional effector comprises a variant of AsiA having mutations in any or all of Q51, V58, and E60 of SEQ ID NO: 80. In some embodiments, the transcriptional effector comprises an amino acid sequence of SEQ ID NO: 80 with a Q51R mutation, V58I mutation, E60K mutation, or any combination thereof. In select embodiments, the transcriptional effector comprises an amino acid sequence of SEQ ID NO:95 or SEQ ID NO: 96.

Also provided for herein are nucleic acids encoding the fusion protein and cells (e.g., bacterial cells) comprising the nucleic acids and/or fusions proteins. The nucleic acids may be contained on a vector (e.g., an expression plasmid or vector with a promoter, as described herein).

Methods for Altering Transcription

Also disclosed herein are methods for altering transcription in a bacteria by introducing into a bacterial cell the system disclosed herein. The descriptions and embodiments provided above for the system components (gRNA, Cas9-transcriptional effector fusion, target DNA, and bacteria) as well as methods of delivery the components provided elsewhere herein are applicable to the methods for altering transcription in a host cell.

In some embodiments, the introduction of the at least one guide RNA (gRNA) and/or at least one second nucleic acid encoding the guide RNA sequence, the fusion protein comprising Cas9 protein linked to a transcriptional effector or variant or fragment thereof and/or a first nucleic acid encoding the fusion protein and the at least one reporter gene and/or at least one third nucleic acid encoding the reporter gene, if applicable is simultaneous or nearly simultaneous. In some embodiments, all the components may be introduced, in any order, with a time period separating each introduction.

Identifying and Screening for Putative Transcriptional Effectors

Also disclosed herein are methods for screening for or identifying a putative transcriptional effector. The methods may comprise introducing into a bacterial host cell a plurality of putative transcriptional effectors linked to a Cas9 protein or a first nucleic acid encoding a putative transcriptional effector linked to a Cas9 protein, at least one guide RNA (gRNA) and/or at least one second nucleic acid encoding the at least one guide RNA sequence, wherein the at least one gRNA is complementary to a target DNA sequence, and a third nucleic acid comprising the target DNA sequence adjacent to at least one reporter gene encoding a gene product; determining the presence or relative quantity of the gene product in the bacterial host cell; isolating bacterial host cells showing a change in quantity of the gene product relative to those host cells lacking the putative transcriptional effector or the gRNA; and identifying the putative transcriptional effector by isolating DNA and/or RNA from the isolated bacterial host cells and sequencing the isolated DNA and/or RNA. The descriptions and embodiments provided above for the second nucleic acid, the gRNA, the third nucleic acid, the target DNA sequence and the bacterial host cell provided elsewhere herein are applicable to the methods for screening for or identifying a putative transcriptional effector.

The introduction of the a plurality of putative transcriptional effectors linked to a Cas9 protein or a first nucleic acid encoding a putative transcriptional effector linked to a Cas9 protein, at least one guide RNA (gRNA) and/or at least one second nucleic acid encoding the at least one guide RNA sequence, wherein the at least one gRNA is complementary to a target DNA sequence, and a third nucleic acid comprising the target DNA sequence adjacent to at least one reporter gene encoding a gene product is simultaneous or nearly simultaneous. In some embodiments, all the components may be introduced, in any order, with a time period separating each introduction.

The Cas9 protein can be obtained from any suitable microorganism, and a number of bacteria express Cas9 protein orthologs or variants (see, e.g., U.S. Pat. No. 10,266,850, incorporated herein by reference in its entirety) and may be used in connection with the present disclosure. The amino acid sequences of Cas proteins from a variety of species are also publicly available through the GenBank and UniProt databases.

In some embodiments, the Cas9 protein is a catalytically-dead Cas9. Catalytically-dead Cas9 is essentially a DNA-binding protein due to, typically, two or more mutations within its catalytic nuclease domains which renders the protein with very little or no catalytic nuclease activity. For example, Streptococcus pyogenes Cas9 may be rendered catalytically dead by mutations of D10 and at least one of E762, H840, N854, N863, or D986, typically H840 and/or N863A (see, e.g., U.S. Pat. No. 10,266,850, incorporated herein by reference in its entirety). Mutations in corresponding orthologs are known. Oftentimes, such mutations cause catalytically-dead Cas9 to possess no more than 3% of the normal nuclease activity.

The transcriptional effector may be linked to the Cas9 protein at the N or C terminus. In some embodiments, the transcriptional effector is linked to the C-terminal end of the Cas9 protein. In some embodiments, a linker (e.g., a peptide linker) is used to link the Cas9 protein and the transcriptional effector. The linkers may comprise any amino acid sequence of any length. The linkers may be flexible such that they do not constrain either of the two components they link together in any particular orientation. The linkers may essentially act as a spacer. In select embodiments, the linker links the C-terminus of the Cas9 protein to the N-terminus of the transcriptional effector. In some embodiments, the linker comprises an amino acid sequence of SAGGGGSGGGGS (SEQ ID NO:1) or CAGGGGSGGGGS (SEQ ID NO:2).

As described above, cells that contain the first nucleic acid, the at least one second nucleic acid, and the at least one third nucleic acid can be constructed using expression vectors for stable or transient expression of the components via conventional methods for vector construction and introduction into the host bacterial cell. For example, nucleic acids encoding the components of the present system may be cloned into a suitable expression vector, such as a plasmid in operable linkage to a suitable promoter. The first nucleic acid, the at least one second nucleic acid, and the at least one third nucleic acid may be provided on a single vector or different vectors. For example, each of the first nucleic acid, the at least one second nucleic acid, and the at least one third nucleic acid may be provided on a first, a second, and a third vector (e.g., plasmid), respectively.

The descriptions and embodiments provided above for the reporter gene are applicable to theses methods as well. In some embodiments, the reporter gene encodes a fluorescent protein, a selection marker, or a combination thereof. In some embodiments, the selection marker comprises a degradation tag. The degradation tag may comprise an amino acid sequence of AANDENYALAA (SEQ ID NO: 66). Thus, the methods for determining the presence or relative quantity of the gene product in the bacterial host cell and/or isolating bacterial host cells showing a change in quantity of the gene product relative to those host cells lacking the putative transcriptional effector or the gRNA may comprise fluorescence detection (fluorescence-activated cell sorting (FACS), fluorescence microscopy, or the like) and or antibiotic or drug selection (colony selection by plate based methods), for example.

The methods may also be used to screen for variants of the identified putative transcriptional effectors. In some embodiments, the methods further comprise mutating the putative transcriptional effector to create a library of mutant transcriptional effectors and repeating the method with the library of mutant transcriptional effectors. Methods for mutating protein sequences are well known in the art, including for example, error prone PCR of the nucleic acid sequence encoding the putative transcription factor as described herein.

Kits

Also within the scope of the present disclosure are kits that include the components of the present system. The kit may include instructions for use in any of the methods described herein. The instructions can comprise a description of the system, components, and/or related methods.

Kits optionally may provide additional components such as buffers, selection antibiotics or drugs, host cells or bacteria clones, plasmids, or vectors without the components, etc. Normally, the kit comprises a container and a label or package insert(s) on or associated with the container. In some embodiment, the disclosure provides articles of manufacture comprising contents of the kits described above.

The kits provided herein are in suitable packaging. Suitable packaging includes, but is not limited to, vials, bottles, jars, flexible packaging, and the like.

EXAMPLES

The following are examples of the present invention and are not to be construed as limiting.

Materials and Methods

Strains and Culturing Conditions

E. coli strains and other bacterial species herein are listed in Table 1 and all E. coli strains were derived from the MG1655 parental background. Cells were grown in rich LB medium at 37° C. with agitation unless stated otherwise. For plasmid transformation, general protocols were followed, and plasmids were maintained under antibiotics selection at all times. For constructing genomic insertions, GFP expression cassette amplified from pWJ89 was cloned between multiple cloning sites of pOSIP-Kan and inserted chromosomally following the clonetegration method (St-Pierre et al., ACS Synth Biol 2: 537-541, incorporated herein by reference in its entirety). For the antibiotic selection and induction of target genes, the following concentrations were used: Carbenicillin (Carb) 50 µg/ml, Chloramphenicol (Cam) 20 µg/ml, Kanamycin (Kan) 50 µg/ml, Spectinomycin (Spec) 50 µg/ml, Bleocin (Bleo) 5 µg/ml, Anhydrotetracycline (aTc) 100 ng/ml. For induction of target genes, aTc was added to the culture at the exponential growth phase for 4 hours before cells were harvested for characterization.

TABLE 1

Bacterial strains and species

| Species | Strain Name | Genotype | Note |
| --- | --- | --- | --- |
| Escherichia coli | BW25113 | F-, DE(araD-araB)567, lacZ4787(del)::rrnB-3, LAM-, rph-1, DE(rhaD-rhaB)568, hsdR514 | Wild-type cell |
| Escherichia coli | WT-GFP | F-, Δ(araD-araB)567, ΔlacZ4787(::rrnB-3), λ-, rph-1, DE(rhaD-rhaB)568, hsdR514, att::[φ21 Wj89-GFP] | Wild-type cell chromosomally inserted with GFP cassette |
| Escherichia coli | JEN202 | F-, ΔrpoZ | Deletion of omega subunit of RNAP |
| Salmonella enterica | Serovar Typhi Ty2 | | Source: ATCC 700931 |
| Klebsiella oxytoca | M5A1 | | Source: DSM 7342 |

Construction of Plasmids

The dCas9 fusion library was constructed based on the pdCas9-bacteria plasmid (Addgene #44249). Linker sequences (SAGGGGSGGGGS (SEQ ID NO: 1)) and fusion candidates were either amplified from DNA synthesized de novo (IDT Gblocks®) or E. coli genomic DNA and subcloned after the dCas9 sequence in the pdCad9-bacteria plasmid (Addgene #44249). All guide RNA plasmids (pgRNA-H1 to pgRNA-H21) were constructed from a pgRNA-bacteria plasmid (Addgene #44251) using inverted PCR and blunt-end ligation to modify the N20 seed sequences. For dual gRNA plasmids (pgRNA-H4H5, pgRNA-H4H11), each gRNA was built separately and jointed subsequently. GFP reporter plasmids (pWJ89, pWJ96, pWJ97) were provided by the Marraffini lab at Rockefeller University. The promoter region upstream of the GFP reporter in pWJ89 was amplified for constructing other antibiotic reporter plasmids (01E134-37). The GFP-mScarlet reporter plasmid (01E139) was constructed by cloning the mScarlet gene from pEB2-mScarlet-I (Addgene #104007) under WJ89 promoter and joined with the constitutive GFP expression cassette from pWJ97. For screening inducible metagenomic promoter library (RS7003), gRNA-H22 and gRNA-H23 expression cassettes were jointed with dCas9-AsiA_m2.1 separately, resulting 01E140, 01E141. Cloning was done by Gibson assembly if not otherwise noted in all cases. Plasmids used and associated details were listed in Table 2.

Figure 6:
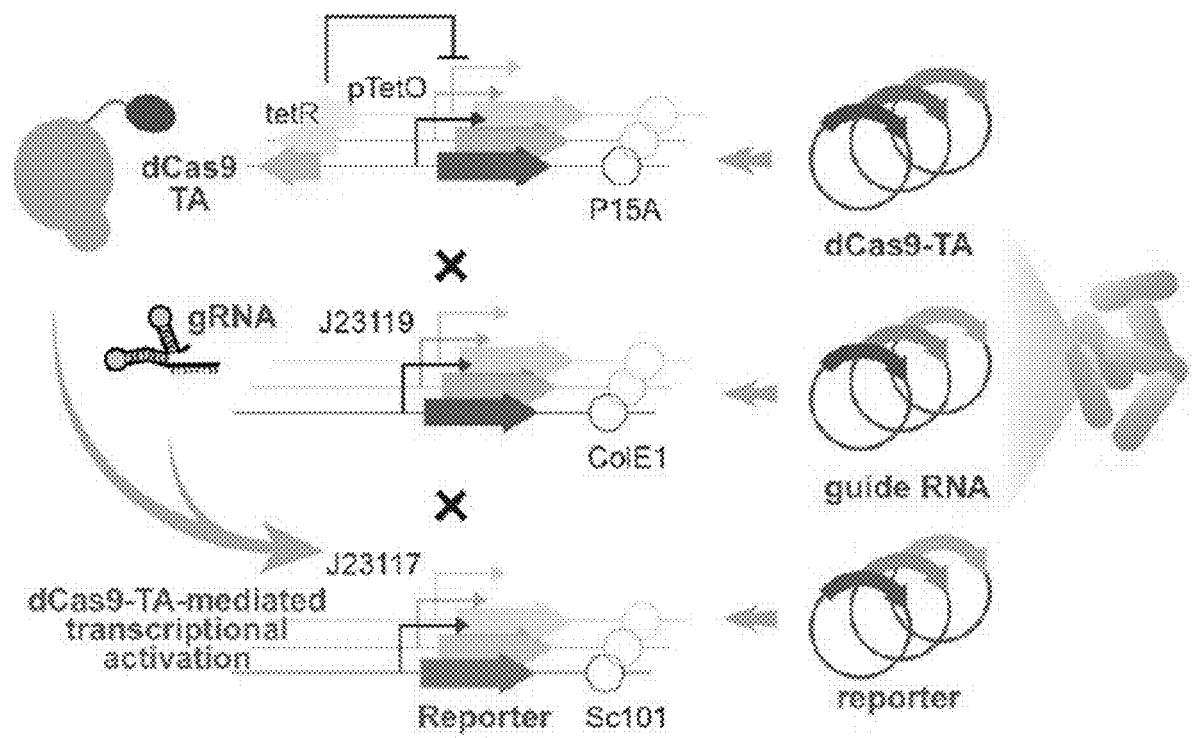
FIG. 6 is a schematic of an exemplary CasTA platform separating 3 key components of CRISPRa, dCas9-TA, gRNA, and reporter, into 3 compatible plasmids that could function in the same cell.
Figure 7A:
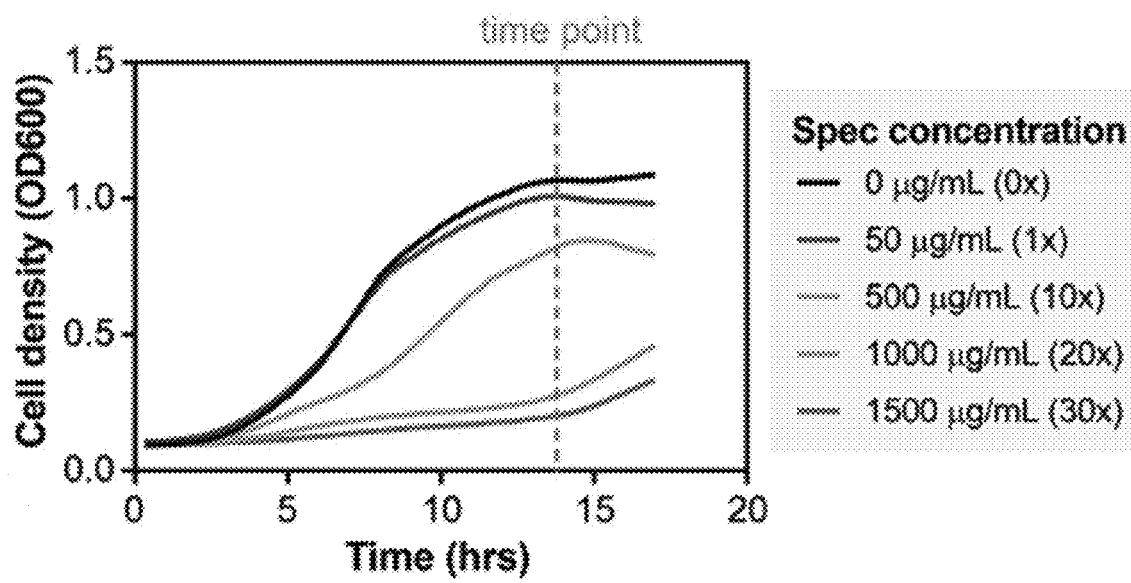
FIGS. 7A-7D shows optimization of selection stringency for CasTA selection platform.
Figure 7B:
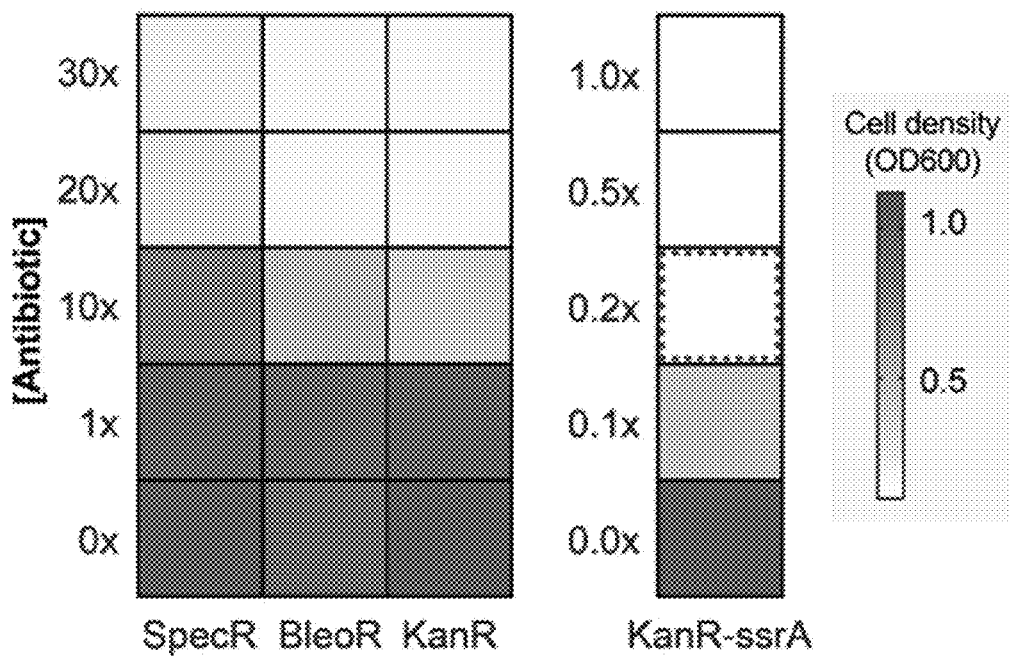
Figure 7C:
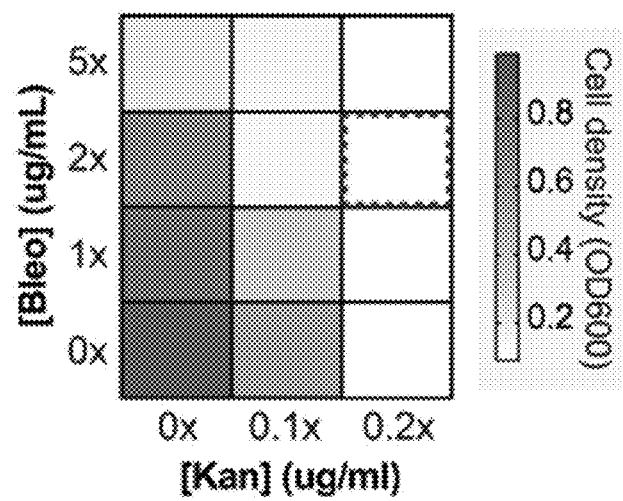
Figure 7D:
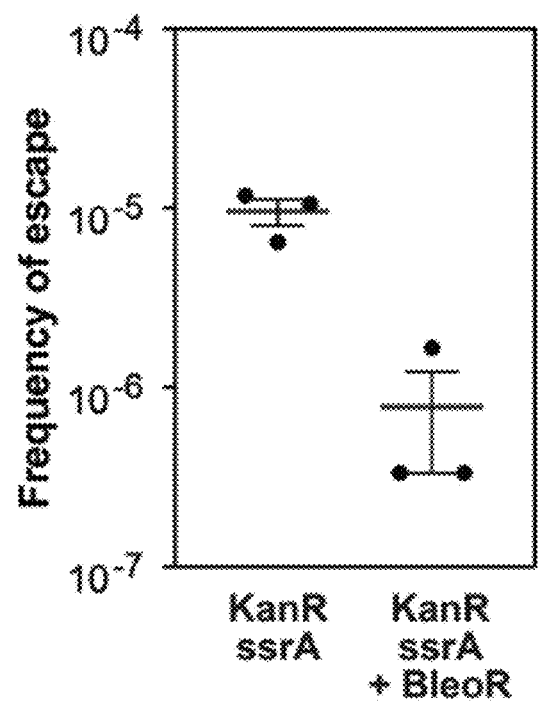

Development of CasTA Screening Platform dCas9 fusion library, gRNAs, and reporter genes were built on 3 different compatible plasmids (dCas9: p15A, Cam resistance; gRNA: ColE1, Carb resistance; reporter: SC101, Kan resistance), for transformation and propagation within the same cell (FIG. 6). To use an antibiotic resistance gene as a reporter, different antibiotic genes were tested and degradation rate (fusion with ssrA tag: AANDENYALAA (SEQ ID NO: 66)) was modulated for selective stringency (FIGS. 7A and 7B). Dual selective reporters (Kan and Bleo) were constructed, which decreased the escape rate by 10 fold (FIGS. 7C and 7D).

Directed Evolution of dCas9-AsiA Using CasTA Screening Platform

Figure 2A:
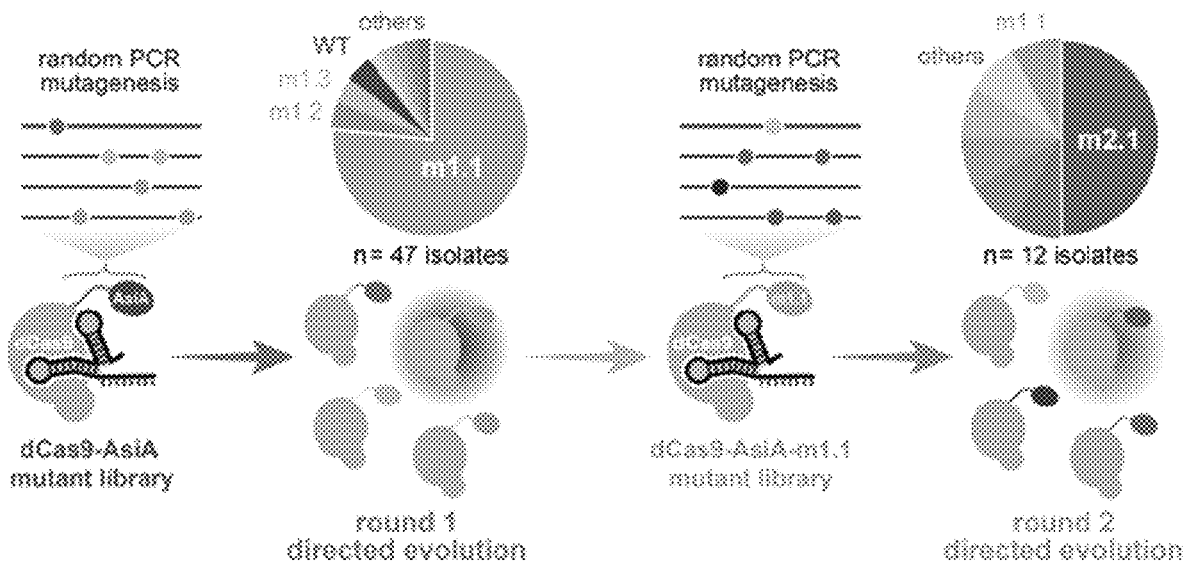
FIGS. 2A-2D show directed evolution of dCas9-AsiA led to higher potency.
Figure 2B:
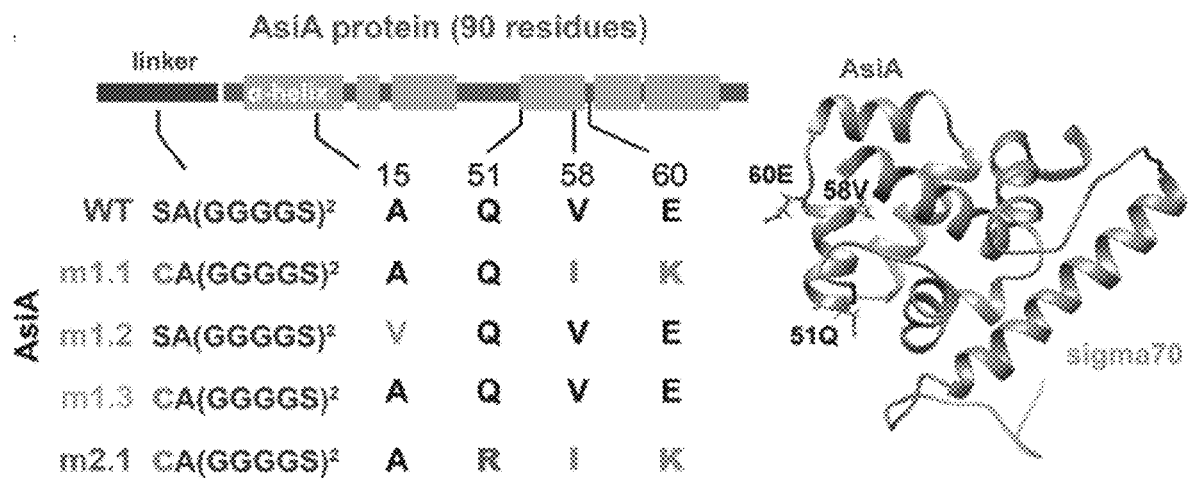
Figure 2C:
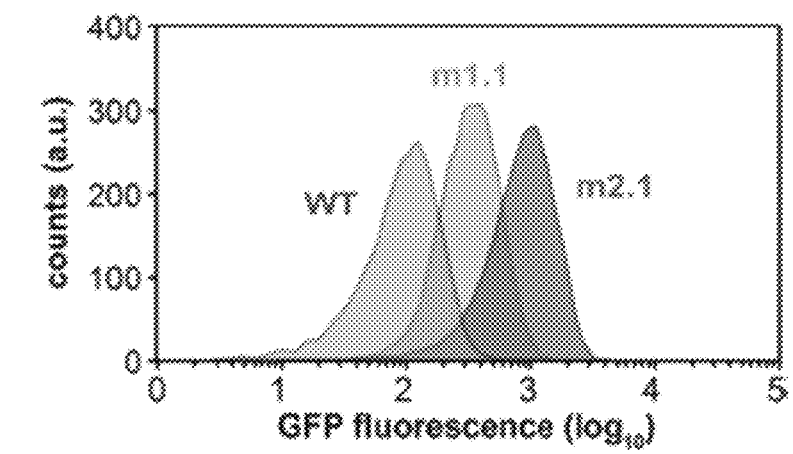
Figure 2C:
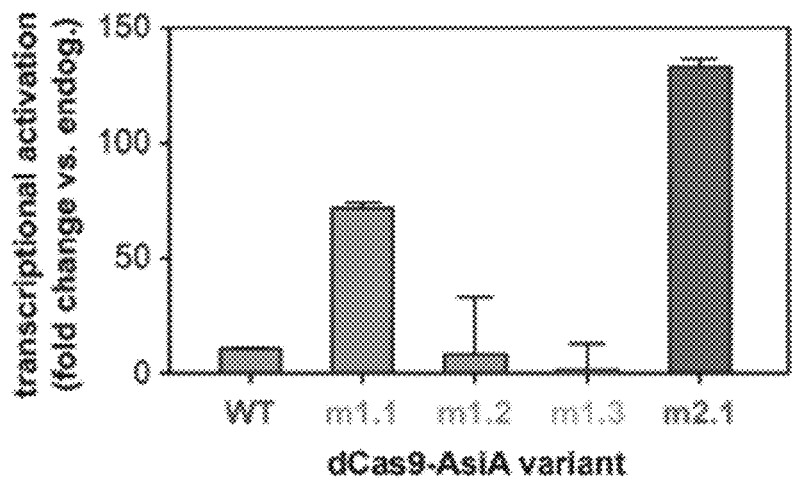
Figures 9A, 9B:
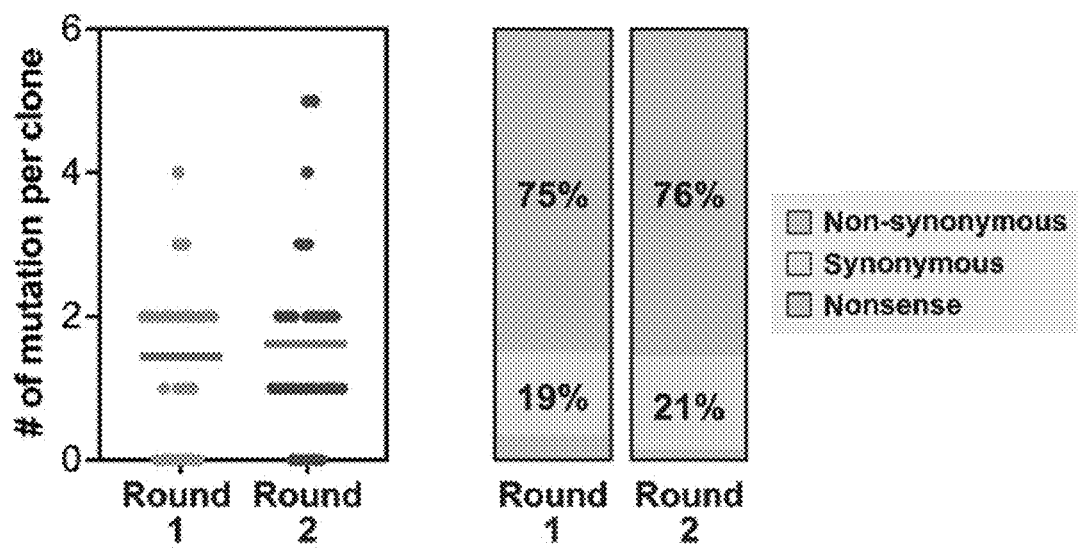
FIGS. 9A-9C show sequence profiling of AsiA variant libraries after PCR mutagenesis. Sanger sequencing of AsiA variants after 2 rounds of mutagenesis indicated the number of mutations per variant (FIG. 9A), the types of mutations in the protein sequences (FIG. 9B), and mutated positions along the protein secondary structure of AsiA (FIG. 9C, indicated by colored ticks). Profiles were generated based on at least 25 randomly selected variants from each round of mutagenesis.
Figure 9C:
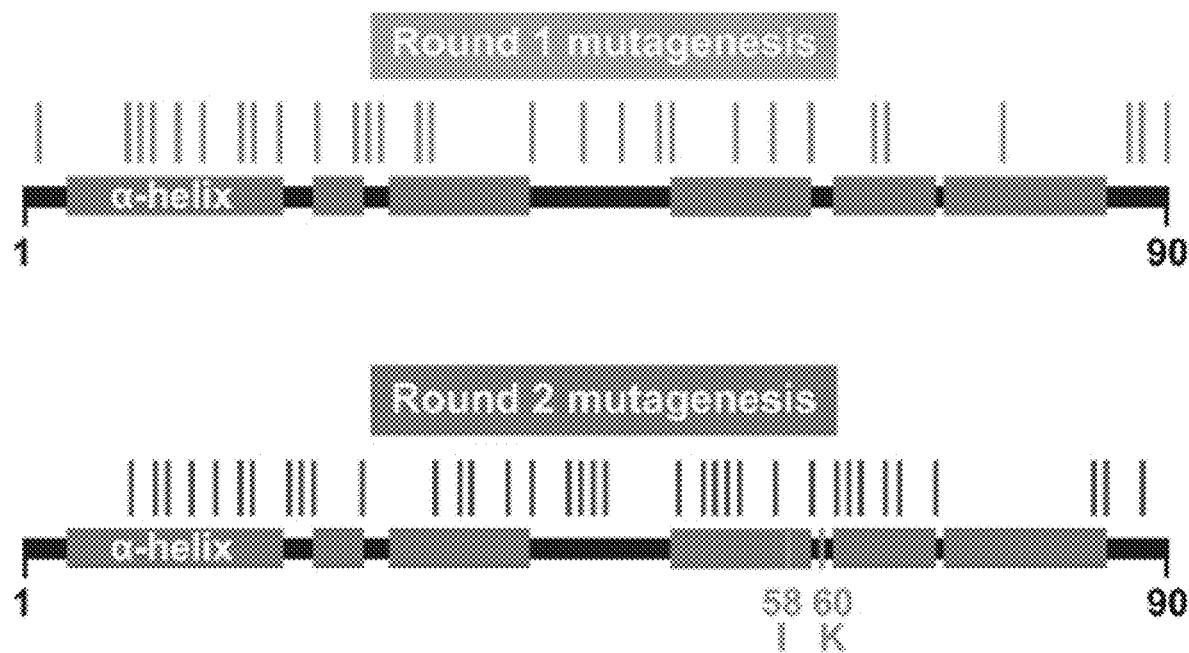

The wild-type AsiA region of dCas9-AsiA was mutated using the GeneMorph II EZClone Domain Mutagenesis Kit (Agilent Technologies), following manufacture's protocol. In brief, 50 ng of parental template DNA was used for amplification with error prone DNA polymerase (Mutazyme II). Under this condition, the AsiA region contains on average ~2 nucleotides changes per variant after PCR mutagenesis (FIG. 9). In the first round of directed evolution, dCas9-AsiA mutant library was transformed to the cells expressing gRNA-H4 and dual selective reporters (01E137 and pHH38). Approximately 5×10$^8$ transformants were grown under 0.2× regular Kan concentration and 2× regular Bleo concentration. Grown colonies were harvested and propagated together with Cam selection to maintain solely the dCas9-AsiA variant plasmids. The dCas9-AsiA plasmids were subsequently extracted and transformed to cells containing pgRNA-H4 and pWJ89. Individual colonies were Sanger sequenced to identify the mutations in AsiA and characterized based on GFP intensity (Table 3). The dCas9-AsiA_m1.1 plasmid from the most abundant mutant variant was extracted and transformed to GFP reporter strain (containing pgRNA-H4 and pWJ89) again to verify fluorescent intensity (FIG. 2C). In the second directed evolution round, the dCas9_AsiA_m1.1 variant was used as a template to generate additional variants following the same conditions. The second generation of dCas9-AsiA mutant library was transformed to GFP reporter cells, containing pgRNA-H4 and pWJ89 as described above. The top 0.1% of highest GFP expression were enriched from the population of 1×10$^7$ transformants using fluorescence activated cell soring (BD FACS Aria II). Post-sorted cell population was plated on selective LB again to obtain clonal colonies, and individual colony was picked for Sanger sequencing and measurement of GFP intensity.

TABLE 2

Plasmids

| Plasmid Name | Description | Promoter for GOI | Antibiotic Resistance | Replication Origin |
|---|---|---|---|---|
| pdCas9-linker | For constructing dCas9 fusion candidate library | pTetO | Cam | p15A |
| pgRNA-bacteria | For constructing different gRNA plasmids | J23119 | Carb | ColE1 |
| pWJ89 | Expressing GFP under weak promoter | J23117 | Kan | Sc101 |
| pWJ96 | Expressing GFP under medium promoter | J23116 | Kan | Sc101 |
| pWJ97 | Expressing GFP under strong promoter | J23110 | Kan | Sc101 |
| pdCas9-AsiA | Expressing dCas9 fusion AsiA | pTetO | Cam | p15A |
| pdCas9-AsiA_m1.1 | Expressing dCas9 fusion AsiA variant 1.1 | pTetO | Cam | p15A |
| pdCas9-AsiA m2.1 | Expressing dCas9 fusion AsiA variant 2.1 | pTetO | Cam | p15A |
| pdCas9-AsiA-wRBS | pdCas9-AsiA with modified RBS sequence from B0034 to B0033 | pTetO | Cam | p15A |
| pdCas9-AsiA_m2.1-wRBS | pdCas9-AsiA_m2.1 with modified RBS sequence from B0034 to B0033 | pTetO | Cam | p15A |
| pHH34 | Expressing Spec resistance gene under weak promoter | J23117 | Kan | Sc101 |
| pHH35 | Expressing Bleo resistance gene under weak promoter | J23117 | Kan | Sc101 |
| pHH36 | Expressing Kan resistance gene under weak promoter | J23117 | Kan | Sc101 |
| pHH37 | Expressing KanR-ssrA under weak promoter | J23117 | Kan | Sc101 |
| pHH38 | Constitutively expressed gRNA-H4 and Bleo resistance gene, serving for dual antibiotic selection | J23119 (gRNA-H4), J23117 (BleoR) | Carb | ColE1 |
| pHH39 | Expressing mScarlet-I under strong promoter and GFP under weak promoter | J23110 (mScarlet-I), J23119 (GFP) | Kan | Sc101 |
| pHH40 | Expressing dCas9-AsiA_m2.1 and gRNA-H22 | pTetI (dCas9-AsiA_m2,1), J23199 (gRNA-H22) | Cam | ColE1 |
| pHH41 | Expressing dCas9-AsiA_m2.1 and gRNA-H23 | pTetI (dCas9-AsiA_m2,1), J23199 (gRNA-H23) | Cam | ColE1 |
| pHH42 | Expressing dCas9-AsiA_m2.1 and gRNA-H24 | pTetI (dCas9-AsiA_m2,1), J23199 (gRNA-H24) | Cam | ColE1 |

TABLE 3

Candidates characterized from dCas9-AsiA directed evolution

| Cycle | Mutations | Frequency | Note |
|---|---|---|---|
| 1st | V58I, E60K, linker S1C | 0.76 | dCas9-AsiA_m1.1 |
| 1st | A15V | 0.04 | dCas9-AsiA_m1.2 |
| 1st | Linker S1C | 0.04 | dCas9-AsiA_m1.3 |
| 1st | E45K | 0.02 | |
| 1st | I70T, linker S1C | 0.02 | |
| 1st | L84S, linker S1C | 0.02 | |
| 1st | E28D | 0.02 | |
| 1st | D6E, I12V, F77S | 0.02 | |
| 1st | WT | 0.04 | |
| 2nd | Q51R, V58I, E60K, linker S1C | 0.5 | dCas9-AsiA_m2.1 |
| 2nd | I40V, V58I, S59R, E60K, E85V, linker S1C | 0.08 | |
| 2nd | R23H, Q51P, V58I, E60K, Y81N, linker S1C | 0.08 | |
| 2nd | N29K, V58I, E60K, T88N, linker S1C | 0.08 | plasmid unstable |
| 2nd | V58I, E60K, L61Q, linker S1C | 0.08 | |
| 2nd | N4I, N32K, V58I, E60K, linker S1C | 0.08 | plasmid unstable |
| 2nd | V58I, E60K, linker S1C | 0.08 | dCas9-AsiA_m1.1 |

Quantification of Gene Expression Induced by CasTA

To examine CRISPRa on genomic targets, pdCas9-AsiA_m2.1 was transformed along with gRNA constructs (gRNA-H12 to gRNA-H21, Table 4) designed for each gene (Table 5). Cells expressing dCas9-AsiA_m2.1 and a non-specific gRNA (gRNA-H4) were used as controls. After CRISPRa induction with 100 ng/ml aTc, cells were harvested for RNA extraction following the RNAsnap protocol (Stead et al, 2012). After column purification (RNA Clean & Concentrator Kits, Zymo Research), total RNA was reverse transcribed into cDNA using random hexamers (SuperScript III Reverse Transcriptase, Invitrogen). Quantitative PCR was performed on each sample with gene specific primers (Table 5) using the KAPA SYBR FAST qPCR Master Mix (Kapa Biosystems). The rrsA gene was selected as the housekeeping gene to normalize expression between samples.

TABLE 4

N20 of gRNAs

| ID | Target | N20 | SEQ ID NO: |
|---|---|---|---|
| H1 | WJ89 | ATGTAACACCGTGCGTGTTG | 4 |
| H2 | WJ89 | GAAGATCCGGCCTGCAGCCA | 5 |
| H3 | WJ89 | GGCTCGAGTCGACAGTTCAT | 6 |
| H4 | WJ89 | CTACGGAACTCTTGTGCGTA | 7 |
| H5 | WJ89 | GCAAAAGCTCATTTCTGAAG | 8 |
| H6 | WJ89 | AACTCTTGTGCGTA | 9 |
| H7 | WJ89-GFP | TTGACAGCTAGCTCAGTCCT | 10 |
| H8 | WJ89-GFP | GCTAGCGAATTCCTTTAAAG | 11 |
| H9 | WJ89-GFP | CCATCTAATTCAACAAGAAT | 12 |
| H10 | WJ89-GFP | GAATTAGATGGTGATGTTAA | 13 |
| H11 | m Scarlet-I | TCTGGGTGCCTTCATACGGA | 14 |
| H13 | cadB | TTTATGTAATAAAAATTATG | 15 |
| H15 | zraP | GCTGTCAGAAAGGGATGAGC | 16 |
| H19 | iraM | TGCCAATTTGCTAAACATTA | 17 |
| H20 | iraD | ATAATACATGGCTGATTATG | 18 |
| H21 | ycgZ | TTTTTATCAATGTAAAGAAA | 19 |
| H22 | RS7003 promoter library | AATAATGGTTTCTTAGACGT | 20 |
| H23 | RS7003 promoter library | AAAAGGGAATAAGGGCGACA | 21 |

TABLE 4-continued

N20 of gRNAs

| ID | Target | N20 | SEQ ID NO: |
|---|---|---|---|
| H24 | Genomic control | AAGCTGAAGAAAAATGAGCA | 22 |
| H25 | dxs | CAATTTAATGATAAACTTCA | 23 |
| H26 | ffh | AGTCTTGCGCTGATTGTTCC | 24 |
| H27 | yehA | ATACCGATCAGCGCAAGCCA | 25 |
| H28 | ydiN | TTTTTACTGGCACTGTTTAT | 26 |
| H29 | idi | CTGATAAAGATTTAAAAGTC | 27 |
| H30 | WJ89 | CGGTGTTACATTAGGCATAC | 28 |
| H31 | WJ89 | AACACGCACGGTGTTACATT | 29 |
| H32 | WJ89 | CGTGCGTGTTGTGGAAGATC | 30 |
| H33 | WJ89 | CGGATCTTCCACAACACGCA | 31 |
| H34 | WJ89 | GCCAAGGTGATAATCCATAG | 32 |
| H35 | WJ89 | TTATCACCTTGGCTGCAGGC | 33 |
| H36 | WJ89 | TGGATTATCACCTTGGCTGC | 34 |
| H37 | WJ89 | GCCTCTATGGATTATCACCT | 35 |
| H38 | WJ89 | ACTGTCGACTCGAGCCTCTA | 36 |
| H39 | WJ89 | CAGTTCATAGGTGATTGCT | 37 |
| H40 | WJ89 | CTCAGGACATTTCTGTTAGA | 38 |
| H41 | WJ89 | CTTGTGCGTAAGGAAAAGTA | 39 |
| H42 | WJ89 | AACACAAACTTGAACAGCTA | 40 |
| H43 | WJ89 | TTTCTGAAGAGGACTTGTTG | 41 |

TABLE 5

Genomic Targets

| Gene ID | Gene name | Forward Primer | Reverse Primer |
|---|---|---|---|
| 945729 | iraM | ATTTCTCCCTCCTGGCAGTA (SEQ ID NO: 42) | TGGAGGACACTCTTGACTGC (SEQ ID NO: 43) |
| 948851 | iraD | AACCCGAGCGACAAACATCT (SEQ ID NO: 44) | GAGTGTGGCAGTACGCTTCT (SEQ ID NO: 45) |
| 945885 | ysgZ | CTCAGCAGGAAACTCTCGGG (SEQ ID NO: 46) | CTGTTCCTCTTCCCCAGTCG (SEQ ID NO: 47) |
| 948654 | cadB | CGGGTATCGCCTGTATTGCT (SEQ ID NO: 48) | CAAACCAATGCCAGCCAACA (SEQ ID NO: 49) |
| 948507 | zraP | GACAGCGTGGCAGAAAATCC (SEQ ID NO: 50) | CTTTGGCGACCGCGTTAATT (SEQ ID NO: 51) |
| 945060 | Dxs | AAGGCCCGCAGTTCCTGCAT (SEQ ID NO: 52) | GGCAAACCGCCGCTACTTTTC (SEQ ID NO: 53) |
| 947102 | Ffh | CTGCAAGGTGCCGGTAAAAC (SEQ ID NO: 54) | TCAAGCTGTTTGATTGCCGC (SEQ ID NO: 55) |

TABLE 5-continued

Genomic Targets

| Gene ID | Gene name | Forward Primer | Reverse Primer |
|---|---|---|---|
| 946642 | yehA | TGGCAAGTCATGGGATGCAT (SEQ ID NO: 56) | AATCGTCCGGTTTGCAGGTT (SEQ ID NO: 57) |
| 946198 | ydiN T | TTCCTGCACGGCATTAGTGT (SEQ ID NO: 58) | ATCAATCGCCCCAAACCGAT (SEQ ID NO: 59) |
| 949020 | Idi | ATCTCGCGTTCTCCAGTTGG (SEQ ID NO: 60) | GATCACTGCGTCTTCGTTGC (SEQ ID NO: 61) |
| 948332 | rrsA | CTCTTGCCATCGGATGTGCCCA SEQ ID NO: 62) | CCAGTGTGGCTGGTCATCCTCT CA (SEQ ID NO: 63) |

For whole-transcriptome analysis of CRISPRa specificity, total RNA from the samples was extracted as described above and rRNAs were depleted using Ribo-Zero rRNA removal-Bacteria kit (Illumina). RNA libraries were prepared using the NEBNext Ultra Directional RNA Library Prep Kit (New England BioLabs) and sequenced on the Illumina NextSeq platform (Mid-Output Kit, 150 cycles). The raw reads were aligned to the reference genome (BW25113) using Bowtie 2, and the read counts of each gene were quantified by HTseq. Expression level of individual gene was normalized by total read counts within each sample.

Total RNA was extracted and purified as previously described. Gene specific primers were used for cDNA generation (Maxima reverse transcriptase, Thermo Scientific), and an RNA sequencing library was prepared by ligation with the common adaptor primer for downstream sequencing. To quantify abundance of each promoter in the library, plasmid DNA from each sample was also extracted using PrepGem bacteria kit (Zygem) and used to generate a DNA amplicon sequencing library. Both RNA and DNA libraries were sequenced on the Illumina NextSeq platform (Mid-output kit, 300 cycles).

TABLE 6

Sequences

| | Sequence |
|---|---|
| Linker | SAGGGGSGGGGS (SEQ ID NO: 1) |
| MS2 Hairpin | GCGCACATGAGGATCACCCATGTGCT (SEQ ID NO: 64) |
| MCP-AsiA | MASNFTQFVLVDNGGTGDVTVAPSNFANGVAEWISSNSRSQAYKVT CSVRQSSAQKRKYTIKVEVPKVATQTVGGVELPVAAWRSYLNMELT IPIFATNSDCELIVKAMQGLLKDGNPIPSAIAANSGIYSAGGGGSGG GGSGGGGSMNKNIDTVREIITVASILIKFSREDIVENRANFIAFLNEIGV THEGRKLNQNSFRKIVSELTQEDKKTLIDEFNEGFEGVYRYLEMYTN K (SEQ ID NO: 65) |
| Degradation Tag | AANDENYALAA (SEQ ID NO: 66) |
| Weak RBS | TCACACAGGAC (SEQ ID NO: 67) |
| Strong RBS | AAAGAGGAGAAA (SEQ ID NO: 68) |
| Constitutive Promoter | GTATACTTTTTTTAAAGAAAAGATTTACAAGCGCACTTTTCTTTAA TATCTTACAATAATGTAAGTTTGAACAGGAGAATGTAAGCCAAAG CGATGGCTACGCATTCTCTTTCTTTGTTATACTAACACCATATTCG AGGTAGAAAATTATTTAGGAGGATAGAT (SEQ ID NO: 69) |

Screening for CRISPRa Mediated Inducible Promoters

Metagenomic promoter library (RS7003) was derived from Johns et al. (Nat Methods 15: 323 (2018), incorporated herein by reference in its entirety). About 8,000 regulatory elements were transformed to cells expressing dCas9-AsiA_m2.1 and either gRNA-H22, gRNA-H23 or genomic targeting gRNA-H24 (Table 4). After CRISPRa induction, four biological replicates were harvested to measure promoter activity. A constitutive promoter without CRISPRa induction (ID:14076, Table 6) was spiked in the cell populations for normalizing expression levels between samples.

Sequencing reads from DNA and RNA libraries were merged by BBmerge and low quality reads were filtered out. Custom pipelines that were previously described (Yim et al., (2019) Mol Syst Biol 15: e8875, incorporated herein by reference in its entirety) were adopted to identify sequencing reads corresponding to each promoter. Expression level of each promoter was quantified by determining the ratio of RNA abundance over DNA abundance. To compare across samples, expression levels were normalized to the same spiked-in control promoter in each sample. Fold change in CRISPRa induced gene expression was calculated by dividing by the reporter expression of control cells containing dCas9-AsiA_m2.1 and a genomic targeting gRNA-H24.

Example 1

A Screening-Selection Platform for Bacterial CRISPRa Development

Figure 1B:
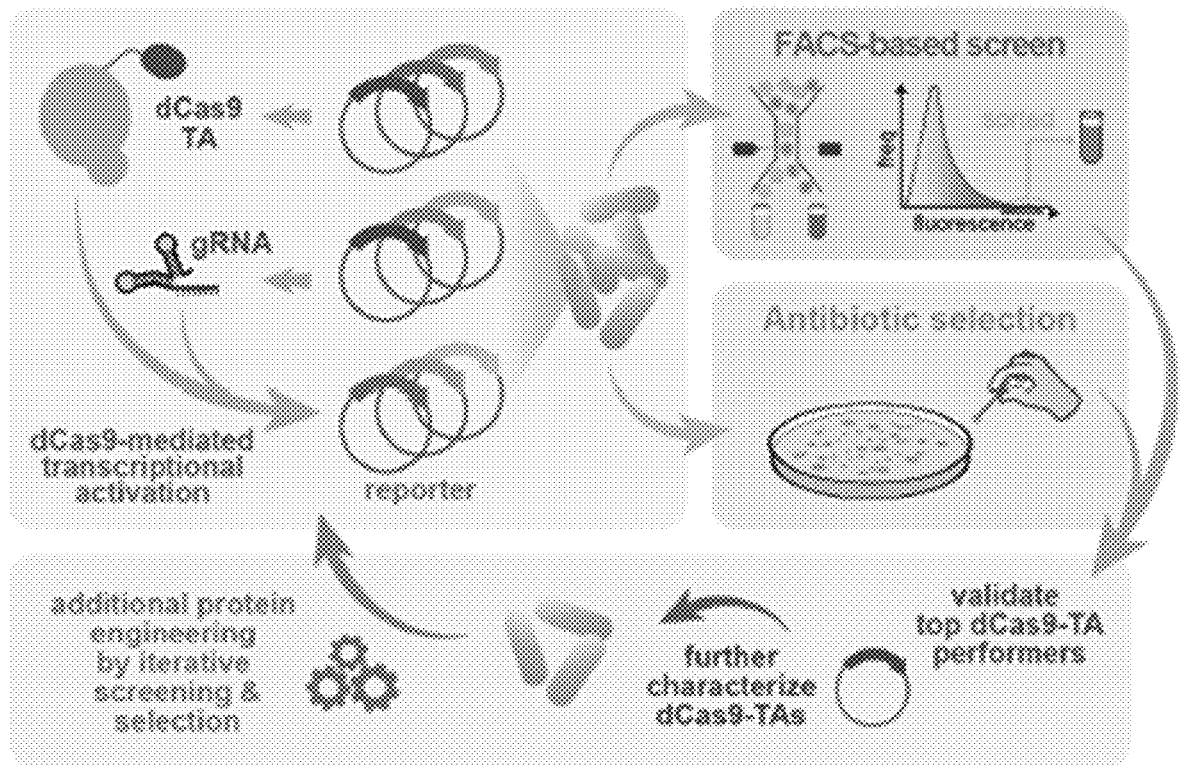

To expedite the discovery of bacterial CRISPRa components, a screening-selection platform in *Escherichia coli* was developed to identify candidate dCas9-mediated transcription activators. In the CRISPRa design, a *S. pyogenes* dCas9 was C-terminally fused with candidate transcription activation domains or proteins via a previously described flexible peptide linker (SAGGGGSGGGGS—SEQ ID NO: 1). This CasTA then used a specific gRNA to target to the regulatory region of a reporter gene for transcriptional activation, gene expression, and production of reporter products (FIG. 1A). The three components of the platform (dCas9-activator fusion, the guide RNA, and the reporter gene) were separated into 3 compatible plasmids (FIG. 1B). The dCas9-activator was regulated by a PtetO induction system with anhydrotetracycline (aTc) on a p15A medium copy plasmid, while the gRNA was constitutively expressed from a strong promoter (BBa_J23119) on a high copy ColE1 plasmid, and the reporter was placed behind a very weak promoter (BBa_J23117) on a low copy SC101 plasmid (FIG. 6). Since different dCas9 activators may have their own respective optimal gRNA binding windows and possible biases toward targetable promoter sequences, the screening-selection platform was designed to be highly modular to facilitate combinatorial assessment of system components. As library-scale screening for transcription activators can often be hampered by auto-activators in the population, a dual screening-selection reporter design using both fluorescent protein and antibiotic resistance genes was employed to eliminate potential false positive clones. The selective reporter was engineered to contain multiple separate antibiotic genes with degradation tags (BBa_M0050) to increase the rate of turnover to reach higher stringency and specificity of the selection (see Methods, FIG. 7).

Figure 1C:
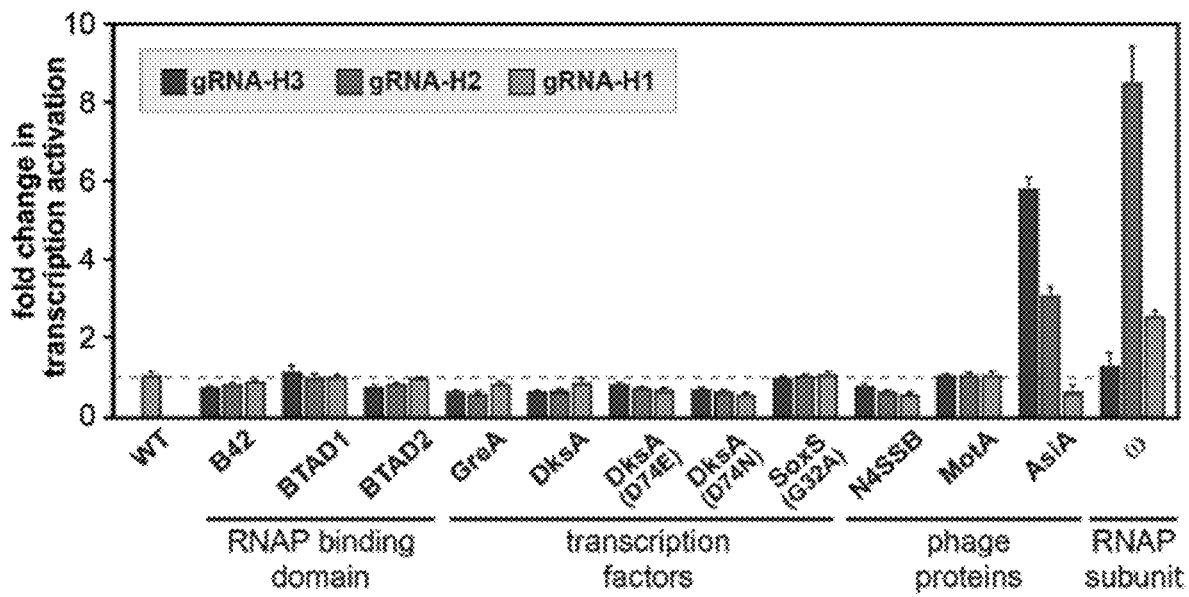
Figure 1D:
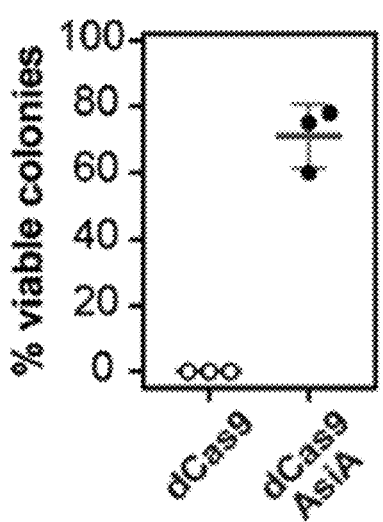

Using this platform, a list of transcriptional activator candidates, including phage proteins, transcription factors, and RNAP interacting proteins (Table 7), paired with different gRNAs (gRNA-H1, gRNA-H2, gRNA-H3) targeted to different spacing distances to transcriptional start site (TSS) of the reporter gene (60 bp, 85 bp, 120 bp, respectively), were screened for potential dCas9-activators. Among the transcription activation modules screened, a phage protein, AsiA, was found that upregulated the reporter gene expression to a level comparable to the previously identified dCas9-ω activator, although at a different optimal spacing distance (FIGS. 1C-1D). AsiA (Audrey Stevens' inhibitor A) is a 90 amino acid anti-σ70 protein from T4 bacteriophage that binds to the host σ70 subunit and suppresses endogenous gene expression. In combination with another T4 phage protein, MotA, the σ70-AsiAMotA complex specifically binds to T4 phage promoters and activates phage transcription during the T4 viral life cycle.

TABLE 7 dCas9 Fusion Candidates

| Candidate | Category | Binding partner of RNAP | Sequence | Notes |
| --- | --- | --- | --- | --- |
| B42 | RNAP binding | Unspecified | GINKDIEECNAIIEQFIDYLRT GQEMPMEMADQAINVVPGM TPKTILHAGPPIQPDWLKSNG FHEIEADVNDTSLLLSGDAS (SEQ ID NO: 70) | |
| BTAD1 | RNAP binding | Unspecified | AEGALDLARAQDLASAAEKA RSAGDLCHARDLLRRALDLW DGEVLAGVPGPYAQTQRVRL GEWRLQLLETRLDMDLDQG CHAEAVSELTALTAAHPLRE RLRELLMLALYRSGRQAEAL AVYADTRRLLADELGVDPRP GLQELQQRILQADPALA (SEQ ID NO: 71) | Bacterial transcriptional activation domain from Streptomyces antibiotic regulatory protein |
| BTAD2 | RNAP binding | Unspecified | PPSTVDVNRFERDADDGQEL LQRGDAAGGTKLGHALALW RGPALADVVASGRLFSYVTR LEELRFRILELRIEADLATGRH RELVSELKSLVLAHPLHEHLH GLLMLALHRSGRPHEALEVY RSVRHKMIEDLALEPAQDFA TLHHTLLSDSPPEA (SEQ ID NO: 72) | Bacterial transcription activation domain from Streptomyces antibiotic regulatory protein |
| GreA | Transcription factor | Beta and beta' subunit | MQAIPMTLRGAEKLREELDF LKSVRRPEIIAAIAEAREHGDL KENAEYHAAREQQGFCEGRI KDIEAKLSNAQVIDVTKMPN NGRVIFGATVTVLNLDSDEEQ TYRIVGDDEADFKQNLISVNS PIARGLIGKEEDDVVVIKTPG GEVEFEVIKVEY (SEQ ID NO: 73) | Type II transcription factor |

TABLE 7-continued dCas9 Fusion Candidates

| Candidate | Category | Binding partner of RNAP | Sequence | Notes |
|---|---|---|---|---|
| DksA | Transcription factor | Unspecified | MQEGQNRKTSSLSILAIAGVE PYQEKPGEEYMNEAQLAHFR RILEAWRNQLRDEVDRTVTH MQDEAANFPDPVDRAAQEEE FSLELRNRDRERKLIKKIEKTL KKVEDEDFGYCESCGVEIGIR RLEARPTADLCIDCKTLAEIR EKQMAG (SEQ ID NO: 74) | Type II transcription factor |
| DksA D74E | Transcription factor | Unspecified | MQEGQNRKTSSLSILAIAGVE PYQEKPGEEYMNEAQLAHFR RILEAWRNQLRDEVDRTVTH MQDEAANFPDPVDRAAQEEE FSLELRNRDRERKLIKKIEKTL KKVEDEDFGYCESCGVEIGIR RLEARPTADLCIDCKTLAEIR EKQMAG (SEQ ID NO: 75) | DksA mutant with higher binding affinity to RNAP |
| DksA D74N | Transcription factor | Unspecified | MQEGQNRKTSSLSILAIAGVE PYQEKPGEEYMNEAQLAHFR RILEAWRNQLRDEVDRTVTH MQDEAANFPDPVDRAAQEEE FSLELRNRDRERKLIKKIEKTL KKVEDEDFGYCESCGVEIGIR RLEARPTADLCIDCKTLAEIR EKQMAG (SEQ ID NO: 76) | DksA mutant with higher binding affinity to RNAP |
| SoxS G32A | Transcription factor | Alpha subunit | MSHQKIIQDLIA WIDEHIDQPL NIDVVAKKSAYSKWYLQRM FRTVTHQTLGDYIRQRRLLLA AVELRTTERPIFDIAMDLGYV SQQTFSRVFRRQFDRTPSDYR HRL (SEQ ID NO: 77) | SoxS variant with defective DNA binding ability |
| N4SSB | Phage protein | Beta and beta' subunit | MSNLFGNLAGQAAKAEKAT DNLGGGFGAKESDIYLATLK VAYAGKAASGANFIQIIADLT DLDGHSAGEYREQLYITSGTE KGCKCTYEKNGKEYFLPGYT VINDILVMTSGETIPEAVFEEK VVNVYDFDEKKEVAKSVMV PVNAIGGKFAVAILKSEEDKQ TKDGSGNYVSTGETRFTNTIE KVFHPDLHLTVVEAEEELTER GKELTVEEAVFWDKWLEKN KGVTRDKTTKGGASGKAGQP PKPGATNTGAGASAAKSLFG KK (SEQ ID NO: 78) | |
| MotA-N | Phage protein | Sigma factor | DLGNAVVNSNIGVLIKKGLV EKSGDGLIITGEAQDIISNAAT LYAQENAPELLKKRATRKAR EITSDMEEDKDLMLKLLDKN GFVLKKVEIYRSNYLAILEKR TNGIRNFEINNNGNMRIFGYK MMEHHIQKFTDIGMSCKIAK NGNVYLDIKRSAENIEAVITV A (SEQ ID NO: 79) | MotA variant with truncation of DNA binding domain at the C-terminus |
| AsiA | Phage protein | Sigma factor | MNKNIDTVREIITVASILIKFS REDIVENRANFIAFLNEIGVTH EGRKLN NSFRKI S LTQED KKTLIDEFNEGFEGVYRYLE MYTNK (SEQ ID NO: 80) | Highlighted residues are those mutated in m1.1 (V58I, E60K) and m2.1 variant (Q51R, V58I, E60K) |
| ω | RNAP subunit | Sigma factor | MARVTVQDAVEKIGNRFDLV LVAARRARQMQVGGKDPLV PEENDKTTVIALREIEEGLINN QILDVRERQEQQEQEAAELQ AVTAIAEGRR (SEQ ID NO: 81) | |

Figure 1E:
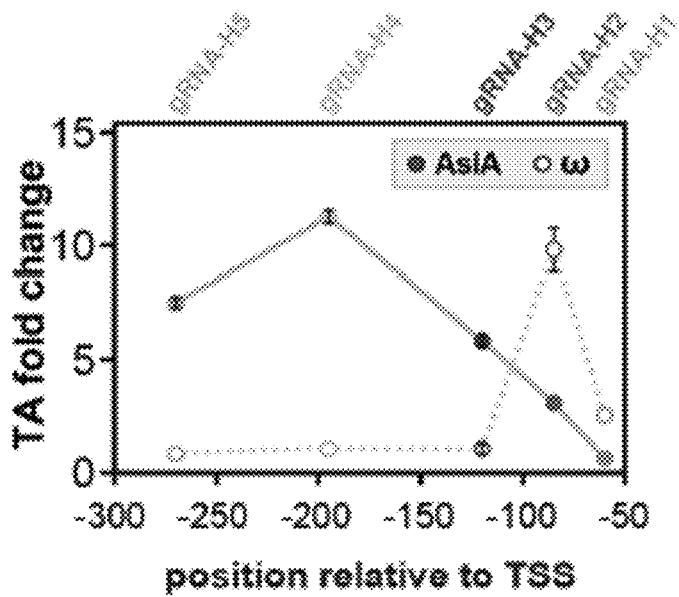
Figure 1F:
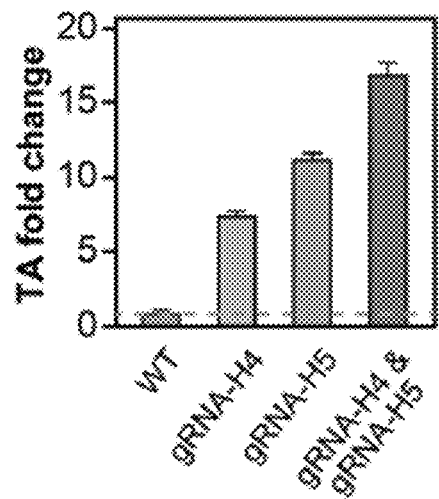

When directly fused to dCas9 with a peptide linker, AsiA upregulated gene expression of a GFP reporter, with the magnitude of activation tunable via design of the gRNA. Transcriptional activation by dCas9-AsiA (dubbed CasTA1.0) was seen across a wide window along the target regulatory region, reaching up to 12-fold at ~200 base pairs (bp) from the TSS (FIG. 1E). In contrast, the optimal gRNA targeting positions for other dCas9 activators (e.g., dCas9-ω and dCas9-MS2/MCP-SoxS) was 100 bp or less from the TSS with a narrower targetable window, possibly suggesting a distinct mechanism of activation by dCas9-AsiA. Unlike other dCas9 activators that mediate activation with re-engineered endogenous transcription factors, AsiA is an anti-σ70 protein that has evolved to outcompete host transcriptional machinery. The strong interaction between AsiA and σ70 may result in a different mode of activation from other systems. Simultaneously targeting with multiple gRNAs furthered increase transcriptional activation (FIG. 1F), although no synergistic enhancement was observed in contrast to eukaryotic CRISPRa systems.

Figure 8A:
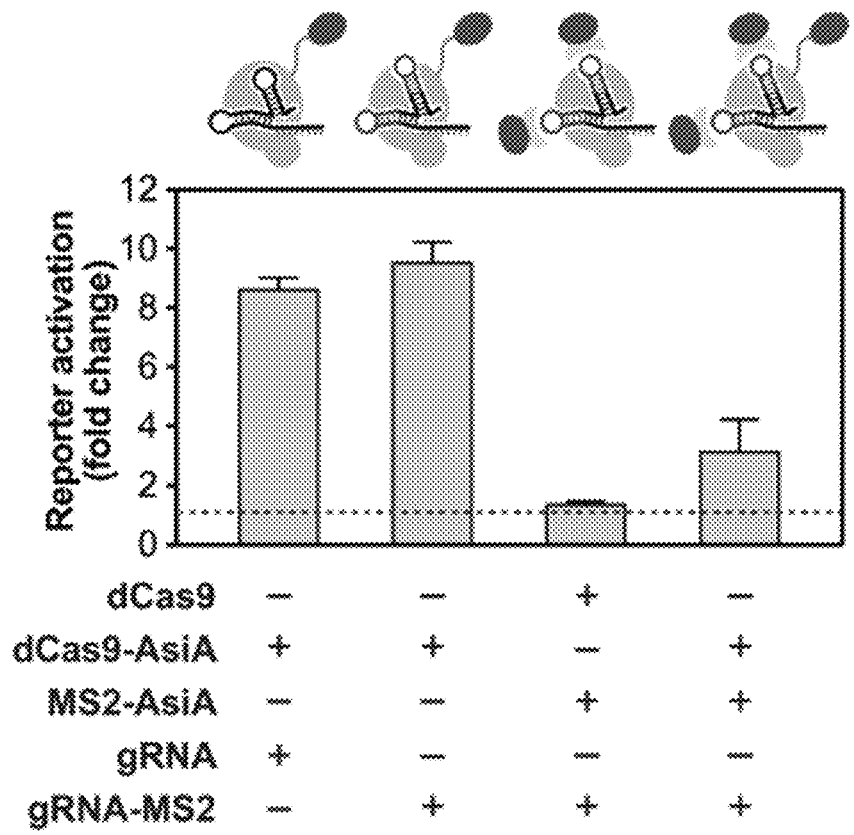
FIGS. 8A and 8B are graphs of the evaluation of different dCas9 transcription activator fusion strategies. dCas9 SAM system with modified gRNA and MS2-AsiA did not enhance CRISPRa activity (FIG. 8A). dCas9 tether AsiA facilitated gene activation (FIG. 8A). Examination of different gRNA designs for improving CRISPRa. n14-gRNA represents design with only 14 nucleotides of the N20 seed sequence; MS2-1: incorporating MS2 hairpin structure in the first loop of the wild-type gRNA structure; MS2-2: incorporating MS2 in the second loop of the wild-type gRNA structure; MS2-tail: MS2 was fused at the 3' end of the gRNA structure (FIG. 8B). Bars are mean of 3-5 biological replicates with error-bars showing as S.E.M.
Figure 8B:
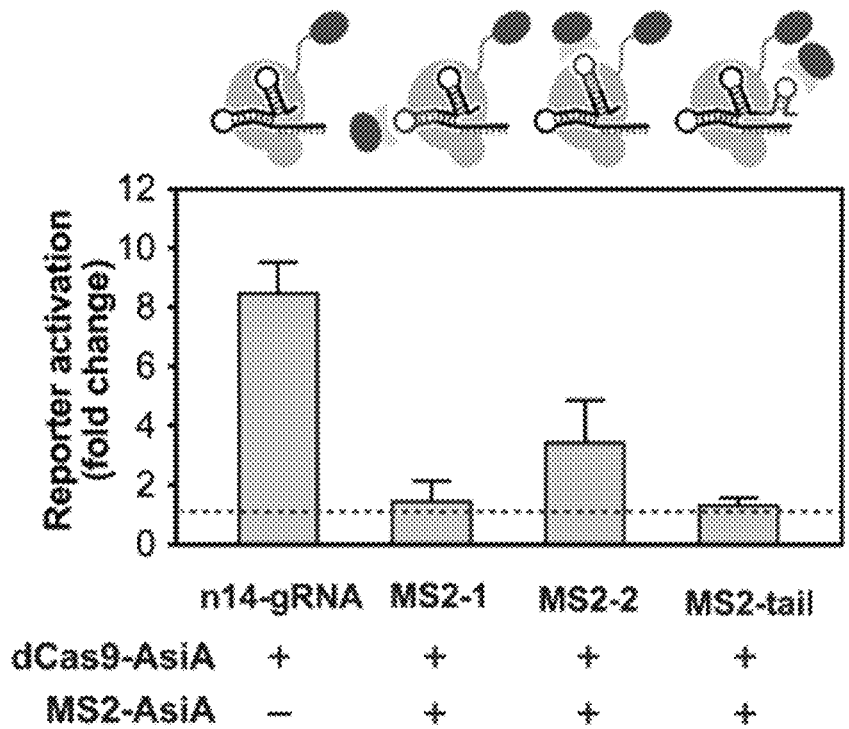

Based on different CRISPRa architectures that have been described in literature, tethering of AsiA to other parts of the dCas9 complex was explored. The MS2 hairpin RNA has been engineered in the gRNA to enable recruitment of transcription activation domains linked to a MCP domain, such as in the bacterial dCas9-MS2/MCP-SoxS system and the eukaryotic Synergistic Activation Mediator (SAM) system. CasTA-AsiA where the gRNA contains a MS2 domain in different stem loops and where AsiA is tethered to MCP (e.g., dCas9-MS2/MCP-AsiA) was tested. While the MS2 hairpins did not affect the gRNA performance, it was not found that the SAM implementation of AsiA could activate gene activation (FIG. 8). These results were in agreement with a previous observation that dCas9-MS2/MCP-AsiA system was not a functional activator. It was also not found that a G32A mutant (DNA binding disruption) of the previously described SoxS activator in the dCas9-MS2/MCP-SoxS system to be functional as a direct dCas9 fusion (e.g., dCas9-SoxSG32A) (FIG. 1C), potentially due to the instability of the G32A mutant. These results highlighted potential mechanistic and performance differences between CRISPRa systems where the activation domain is directly fused to dCas9 versus tethered via the MS2-MCP system.

Example 2

Directed Evolution and Characterization of the dCas9-AsiA Transcriptional Activator To increase the dynamic range and performance of dCas9-AsiA-mediated transcriptional activation, a series of directed evolution studies using our screening-selection platform were performed. A dCas9-AsiA variant library was constructed by error-prone PCR of AsiA, with each AsiA variant having on average two randomly distributed residue mutations (FIG. 9). Approximately $5 \times 10^8$ AsiA mutant variants were screened for improved transcriptional activation on antibiotic selection plates (FIGS. 2A and 7). The resulting colonies were individually isolated and plasmids encoding the dCas9-AsiA variants were extracted and transformed into cells expressing a gRNA and GFP reporter for re-validation (Table 3). Of 47 colonies isolated and characterized, one variant (m1.1) was found most enriched (>75% of the time), while several other variants (m1.2, m1.3) were also identified at lower frequency (FIG. 2A-B). The most abundant variant m1.1 after selection also mediated the highest GFP activation (FIG. 2C). The m1.1 variant contained two key mutations on AsiA (V58I, E60K). An additional mutation (S1C) on the peptide linker was also found, which likely arose during the cloning steps of the directed evolution protocol. Interestingly, the AsiA mutations occurred within the middle of the anti-σ factor protein and are structurally away from the interface that binds to σ70 (FIG. 2B). AsiA binds to sigma factors through the first helix structure (residues 1 to 20), suggesting that the mutations in m1.1 may not affect direct binding to sigma factors. This m1.1 variant significantly increased the transcriptional activation to ~70 fold compared to ~10 fold using the wild-type AsiA (FIG. 2C). Another round of directed evolution was performed on m1.1 and the resulting clones were screened for additional mutants with further improvements (FIG. 2A). From 107 variants, validation and characterization of the resulting colonies revealed an additional mutant (m2.1) to be significantly enriched in the population with >135-fold activation (FIGS. 2B and 2C). The m2.1 variant contained an additional Q51R mutation, which also faced away from σ70 similar to the other m1.1 mutations.

Figure 2D:
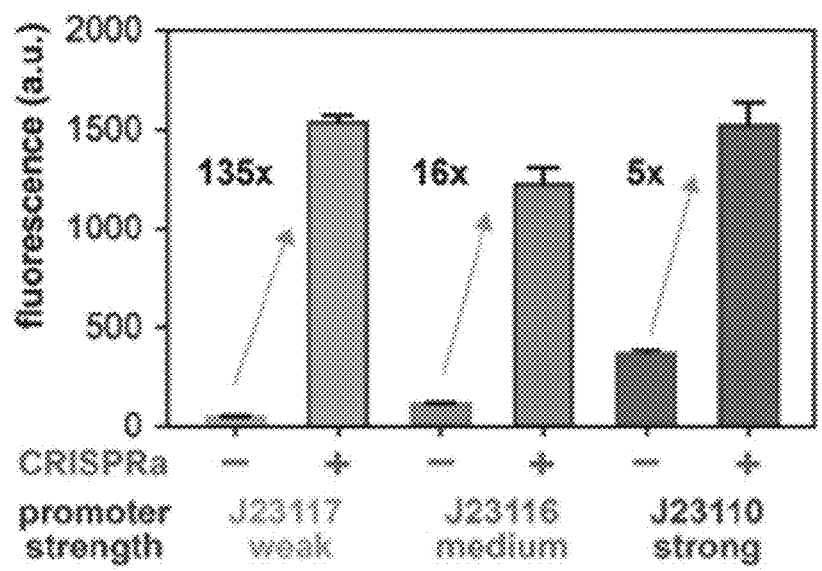
Figure 10A:
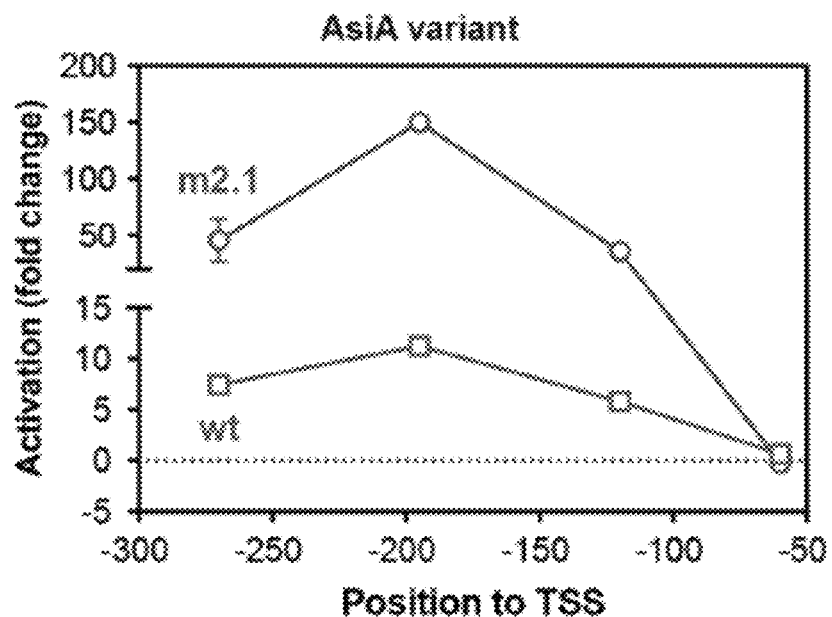
FIGS. 10A-10D are graphs of the characterization of dCas9-AsiA mediated CRISPRa.
Figure 10B:
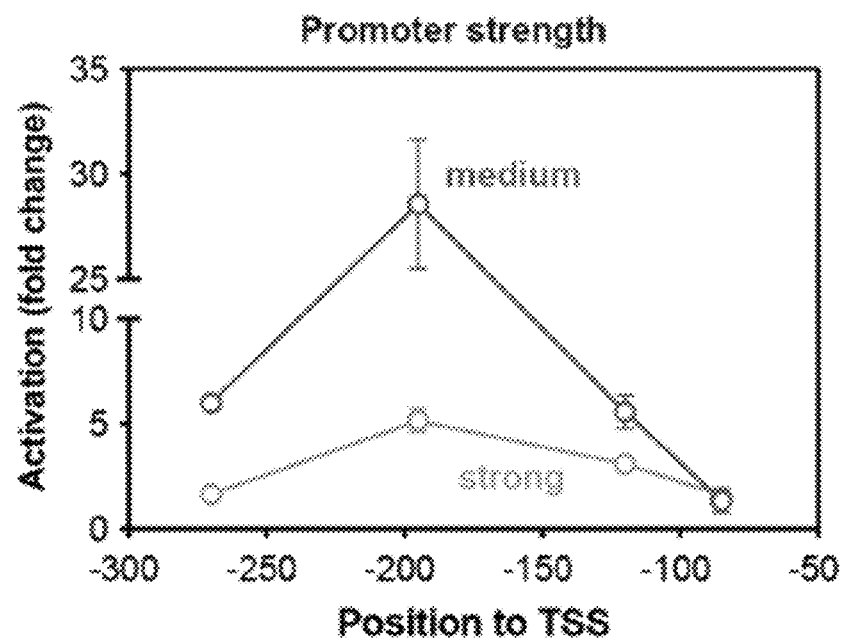
Figure 10C:
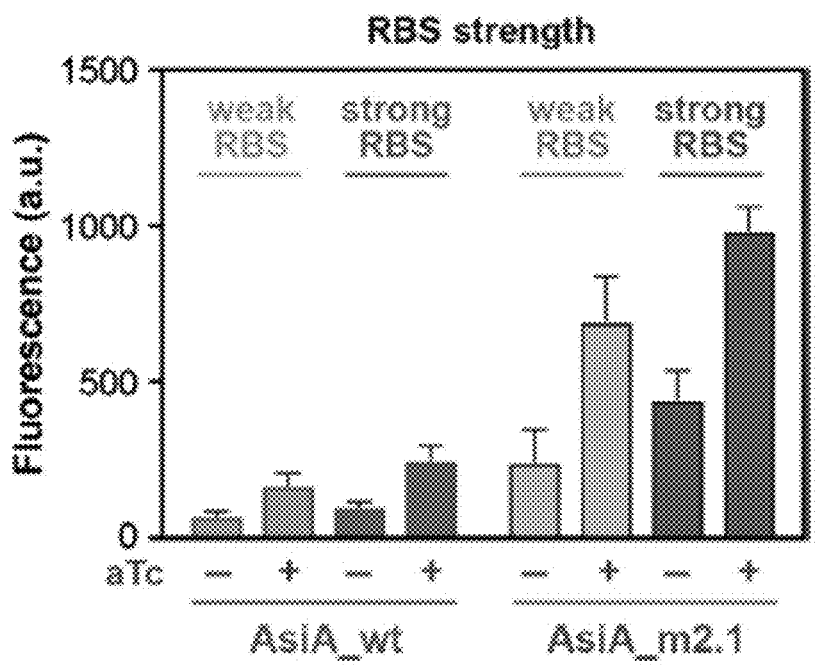
Figure 10D:
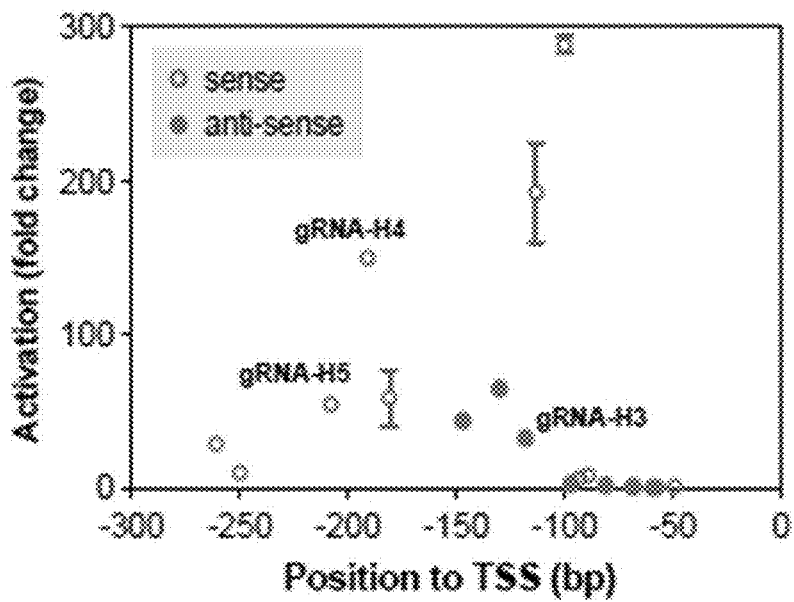

The activation potential of dCas9-AsiA-m2.1 (CasTA2.1) for targeting promoters with different basal expression levels and at different CasTA2.1 expression levels was explored. Transcriptional activation across weak to strong promoters reached similar saturating levels and at the same optimal gRNA targeting distance (FIGS. 2D, 10A, and 10B). The fold induction inversely correlated with the basal promoter strength. To investigate the rules for gRNA designs at finer resolution, gRNA targeting all NGG positions in the weak promoter (BBa_J23117) except for ones overlapping with σ70 binding sites were constructed and paired with CasTA2.1 to mediate gene activation. An additional peak of activation was found at around 100 bps to TSS (FIG. 10D). Similar periodicity of optimal gRNA targeting was recently observed in the dCas9-MS2/MCP-SoxS system. However, CasTA2.1 has a generally broader activation window. gRNAs tested with distances of more than 100 bp from the TSS, all led to gene activation from 10- to 288-fold. These 10 gRNAs targeted promoter regions across more than 150 bps, suggesting a flexible window from effective gRNA designs. Transcriptional or translational enhancement of the expression of CasTA1.0 or 2.1 could also increase activation of the target gene (FIG. 10C), thus providing different options to tuning the overall system.

Figure 11:
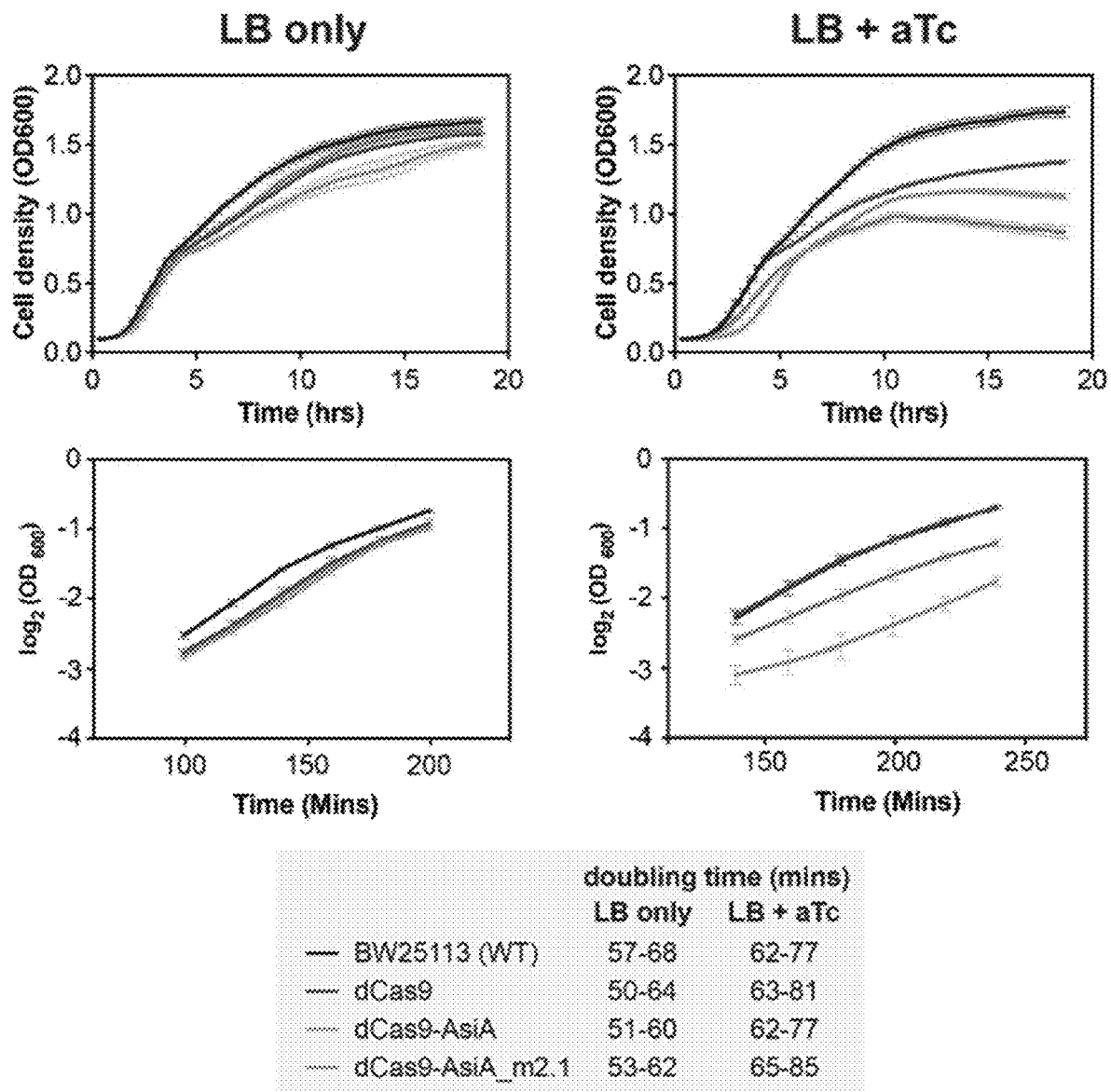
FIG. 11 is graphs of the growth of cells expression dCas9-AsiA. Cells carrying different dCas9-AsiA plasmids were grown in rich media with (LB+aTc) or without (LB only) dCas9 overexpression. Growth curve and doubling times in the exponential growth phase are shown. Data are three biological replicates with errorbars as +/−S.E.M.

Since AsiA binds and sequesters the host σ70, overexpression of AsiA may become toxic to the cell. The toxicity of dCas9-AsiA was quantified in the system. Overexpression of CasTA1.0 or 2.1 under aTc induction did not have significant impact on cellular growth rate beyond the basal fitness burden of dCas9 overexpression alone (FIG. 11). Doubling times during exponential growth were generally unaffected under CasTA overexpression, while stationary cell density was somewhat impacted.

Figure 12A:
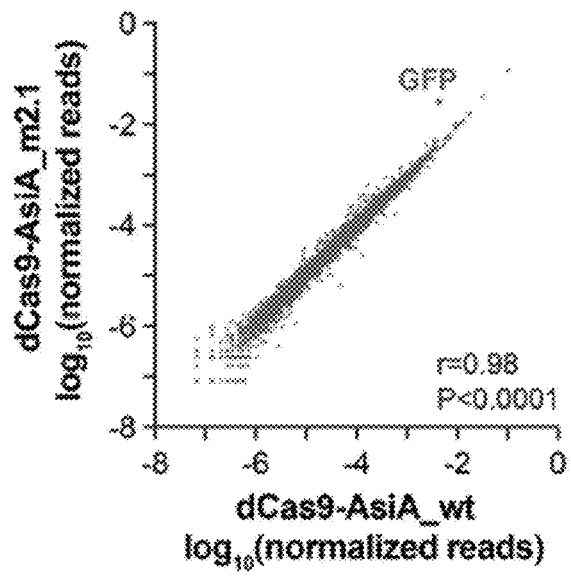
FIGS. 12A-12C show the specificity of gene activation using dCas9-AsiA_m2.1.
Figure 12B:
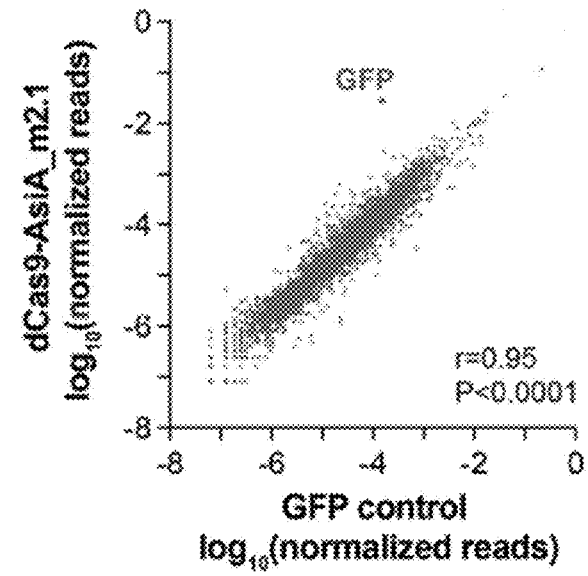
Figure 12C:
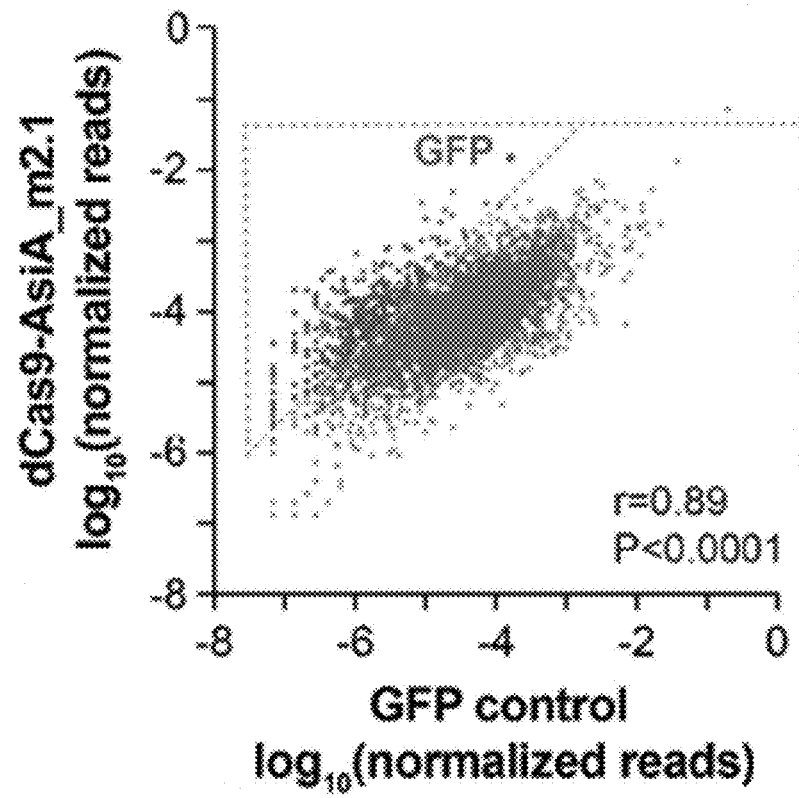

To gain a higher resolution of the effects of CasTA on the endogenous transcriptome, RNAseq was performed on cells with CasTA1.0 and CasTA2.1, relative to ancestral control cells (FIG. 12). CasTA2.1 mediated higher gene activation on the GFP target without loss of specificity genome-wide compared to cells with CasTA1.0 (FIG. 12A) or ancestral cells (FIG. 12B). Upon overexpression of CasTA2.1, upregulation of some low-expression endogenous genes was observed (FIG. 12C). These off-target gene activations may be the result of non-specific dCas9 binding to other genomic loci, which has been reported previously. This was supported by the fact that strong off-targets (fold change >30) were regulated by not just σ70 but also other σ factors (FIG. 12C). Notably, the fold induction of the GFP targets was also higher under significant CasTA2.1 overexpression (FIG. 12C), which highlights a trade-off between higher target activation and increased off-targets in this CRISPRa system.

Example 3

Figure 3A:
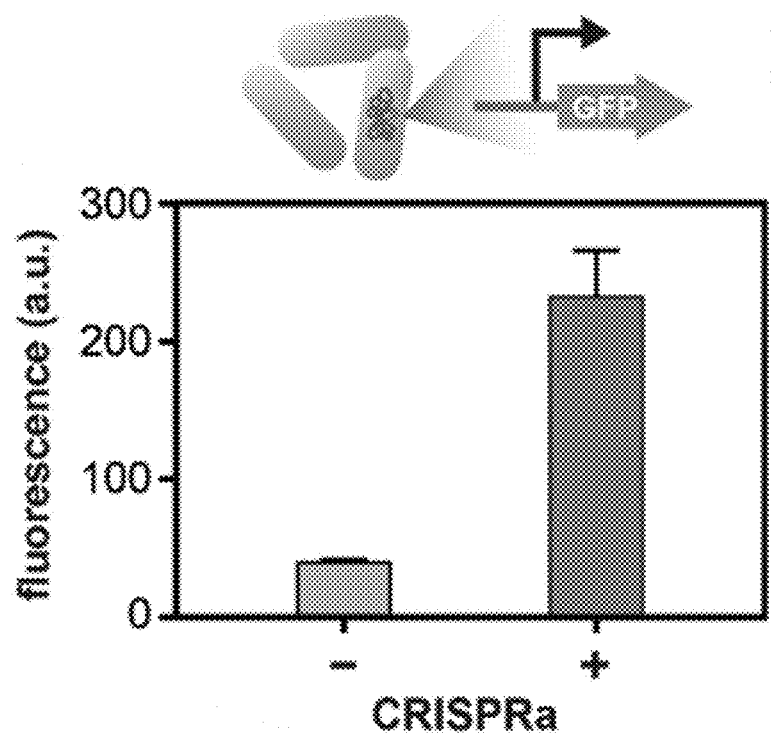
FIGS. 3A-3D show evolved CasTA2.1 activated genomic targets and mediated multiplexed gene activation and repression.
Figure 3B:
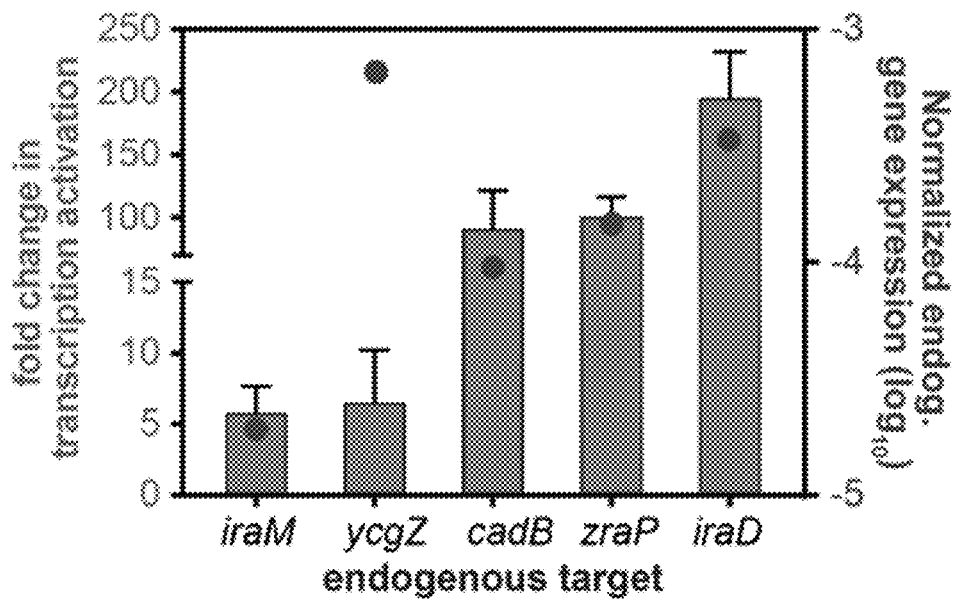
Figure 3C:
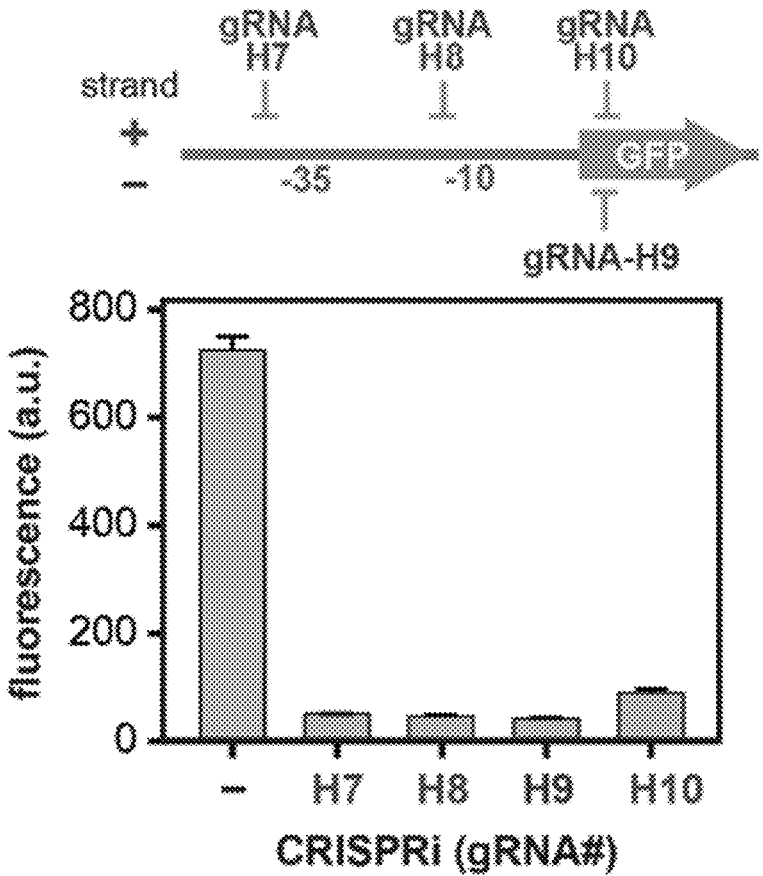
Figure 3D:
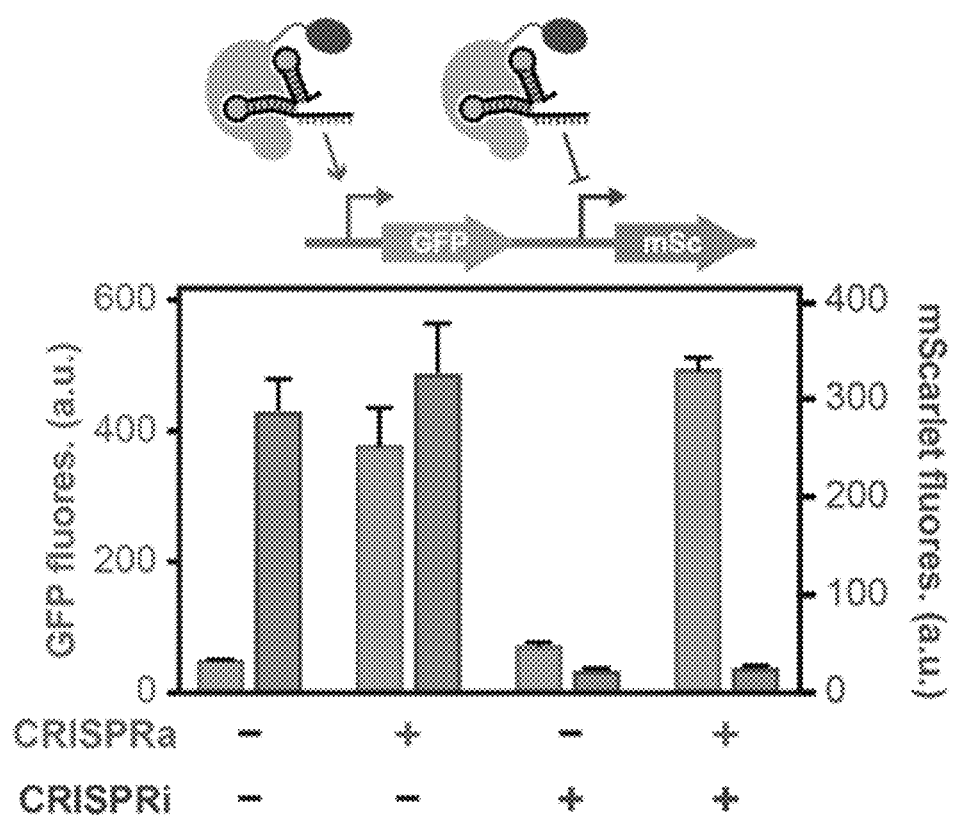
Figure 14:
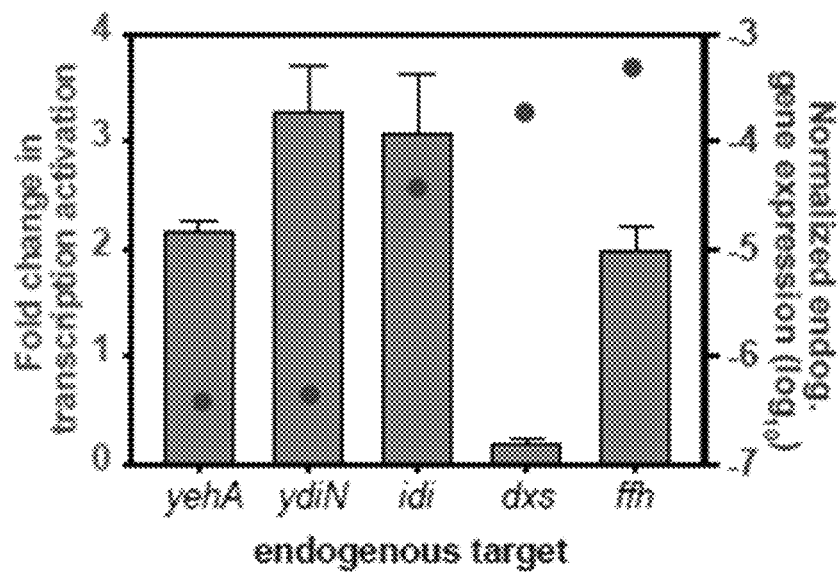
FIG. 14 is a graph of fold change in transcription activation and normalized endogenous gene expression using dCas9-AsiA_m2.1 to activation genomic targets. Chromosomal genes were selected to test with CasTA2.1 on gene activation. Expression was quantified using RT-qPCR, and genes with modest or no activation (<5 fold) were plotted with bars showing the activation fold change and dots showing basal expression of each gene. Data were mean of 3 biological replicas+/−SEM.

Utility of dCas9-AsiA for Multi-Gene and Library Scale Transcriptional Regulation To explore whether CasTA can be used to regulate endogenous genomic targets, a GFP reporter was inserted into the genome and CasTA2.1 upregulated the expression of this chromosomal reporter (FIG. 3A). Five genes in the genome could be upregulated (by up to 200-fold) using CasTA2.1 (FIGS. 3B and 14; Table 5). One gRNA was designed for each gene using a search window of 200±20 bp from the TSS. Optimization of gRNA designs may be used for different genomic targets. gRNAs (gRNA-H7 to gRNA-H10) positioned near the TSS or within the gene body of the target GFP reporter efficiently inhibited gene expression using the CasTA2.1 protein, including both strands of the target DNA (FIG. 3C). When two different gRNAs were designed to target two reporter genes for concurrent activation and repression, simultaneous CRISPRa and CRISPRi was observed using CasTA2.1 at efficiencies similar to applying CRISPRa or CRISPRi separately (FIG. 3D), which highlighted the systems potential utility for multiplexed gene modulation of regulatory networks in a single cell.

Figure 4A:
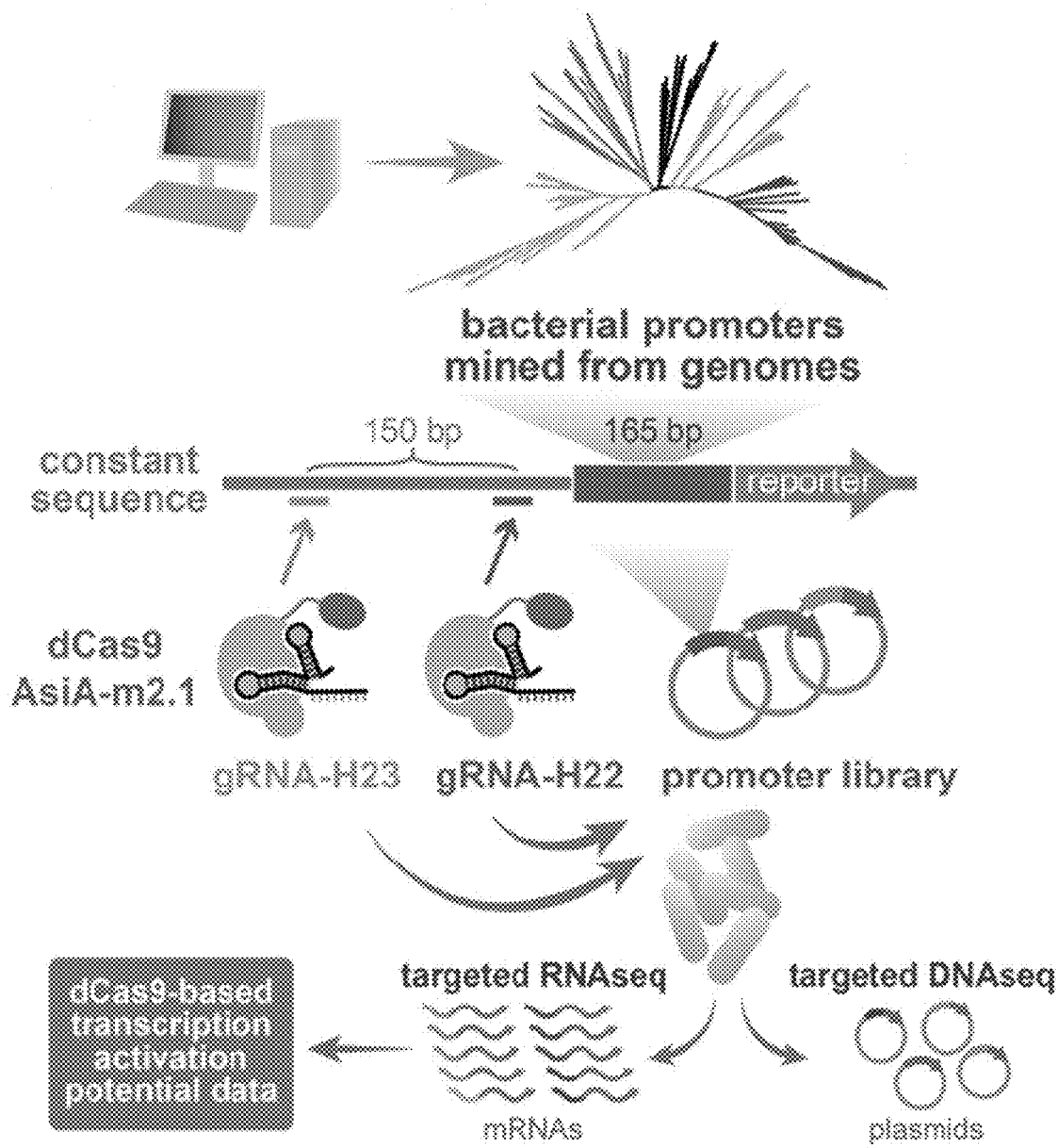
FIGS. 4A-4C show multiplex reporter assay used to identify inducible promoters using CasTA2.1.
Figure 4B:
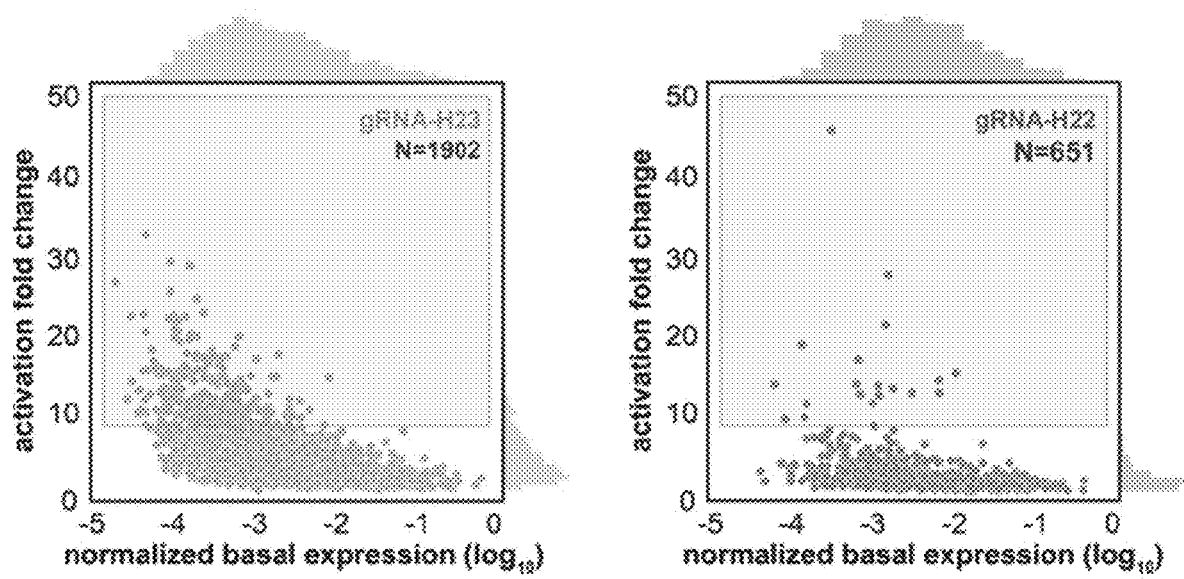
Figure 4C:
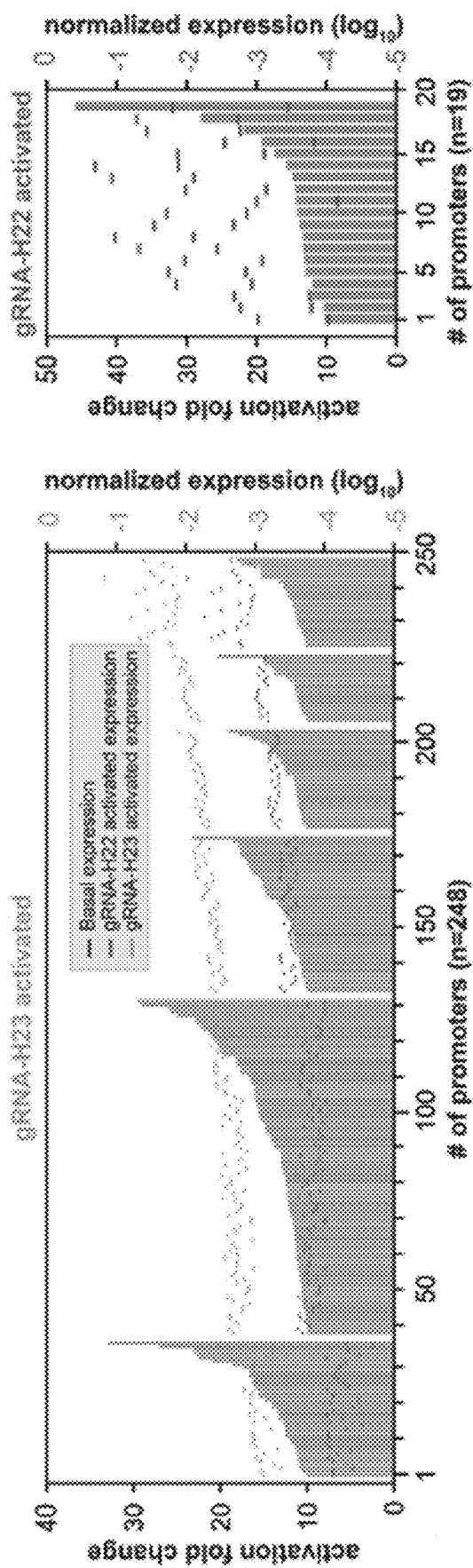
Figure 13A:
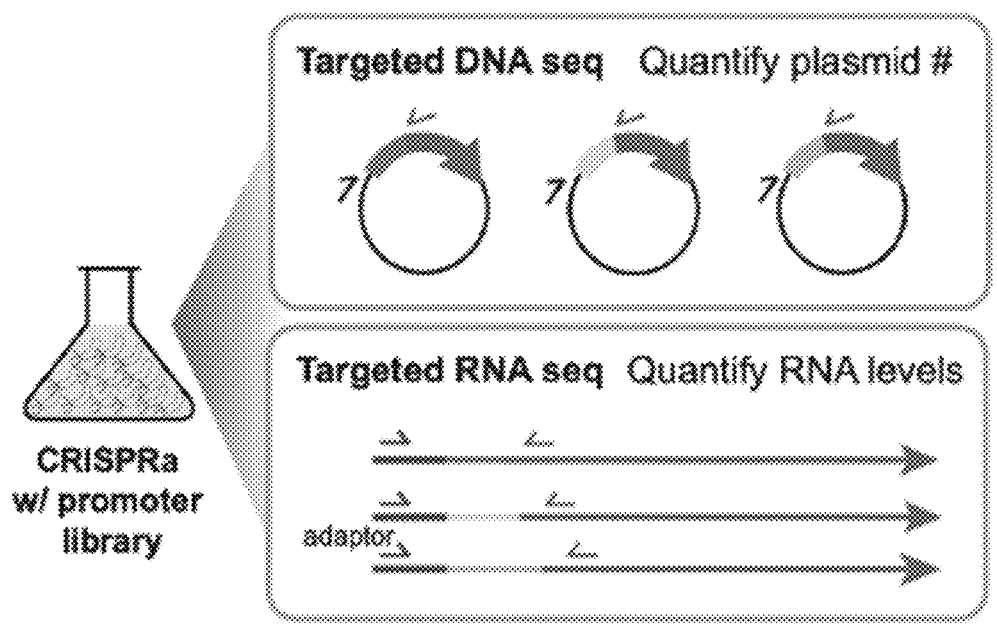
FIGS. 13A-13C show a bacterial CRISPRa screen to identify new orthogonal inducible promoters.
Figure 13B:
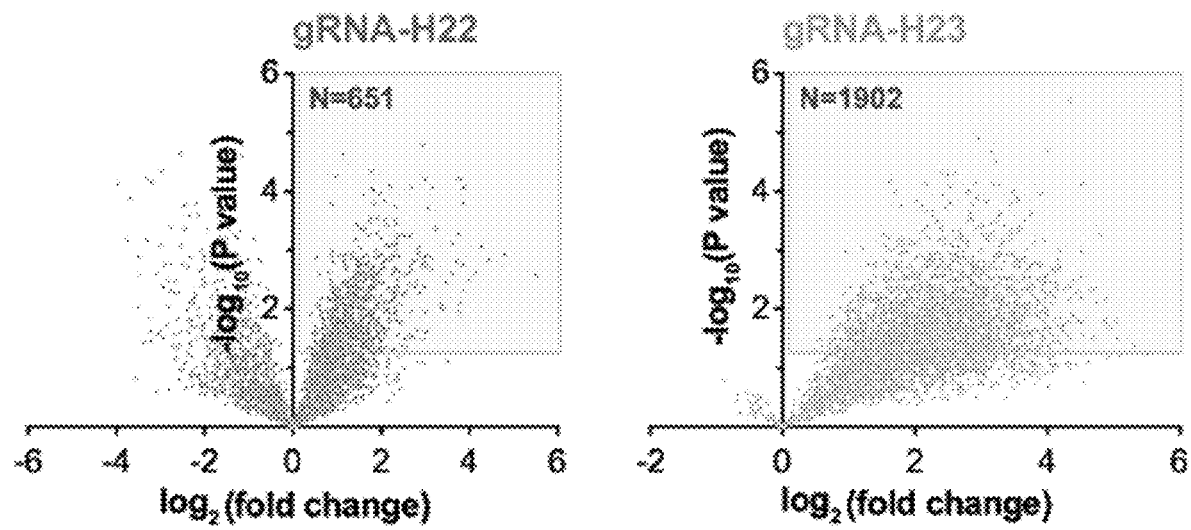
Figure 13C:
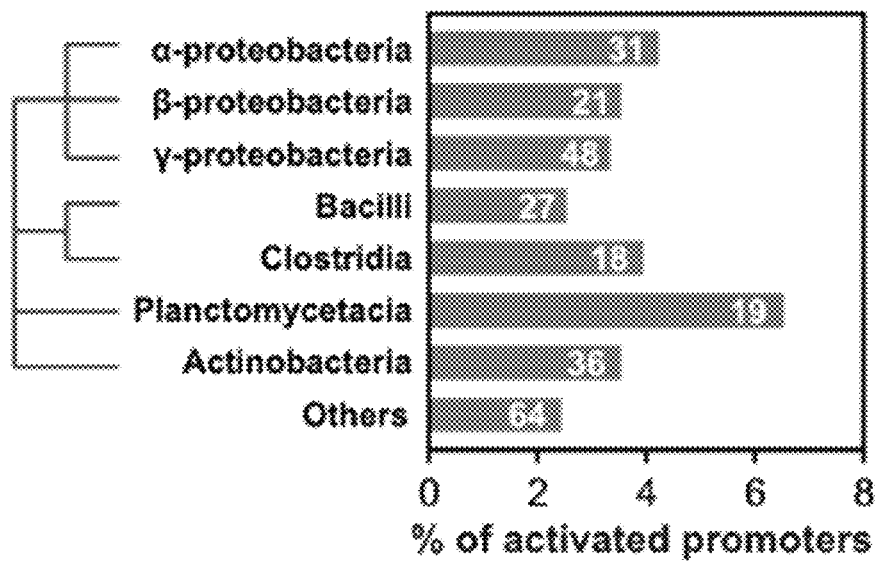

Development of complex synthetic genetic circuits requires diverse regulatory parts with tunable dynamic rage. However, the number of inducible promoters with defined expression ranged is limited for many applications in synthetic biology. A promoter library from metagenomic sequences with varying species-specific constitutive expression levels was previously developed (Johns et al., 2018 Nat Methods 15: 323, incorporated herein by reference in its entirety). Whether such a constitutive promoter library could be turned into an inducible promoter library was explored using the present CRISPRa system (FIG. 4A). Two gRNAs spaced ~150 bp apart targeting the constant regulatory region upstream of the variable regulatory sequences of each promoter were designed and a screen identified subsets of promoters that could be upregulated by CasTA2.1. The expression level from all promoters in the library with and without CasTA2.1 was quantified by targeted RNAseq (to obtain RNA transcript for each promoter) and DNAseq (to normalize for plasmid copy numbers across the library) as previously described (Yim et al., (2019) Mol Syst Biol 15: e8875, incorporated herein by reference in its entirety) (FIG. 13A, Methods). Of approximately 8,000 promoters characterized, thousands of promoters that were activated by CasTA2.1 with at least one of the gRNAs were identified (FIGS. 4B and 13B). Among them, several hundred had a high level of induction (>10-fold) across 2-orders of magnitude in basal expression level (FIG. 4C). In general, more promoters were activated with the distal gRNA (gRNA-H23), although interestingly the proximal gRNA (gRNA-H22) also resulted in CRISPRi activity in some promoters (FIG. 13B). The phylogenetic origin and sequence composition of these inducible promoters were diverse, which may facilitate their use for assembly of large genetic circuits with minimal recurrent sequence motifs (FIG. 13C). This library of CasTA-inducible promoters greatly expands the repertoire of regulatory parts that can be activated with one or two gRNAs by CRISPRa for more complex genetic circuits in various synthetic biology applications.

Example 4

Portability of dCas9-AsiA to Other Bacteria Species

Figure 5C:
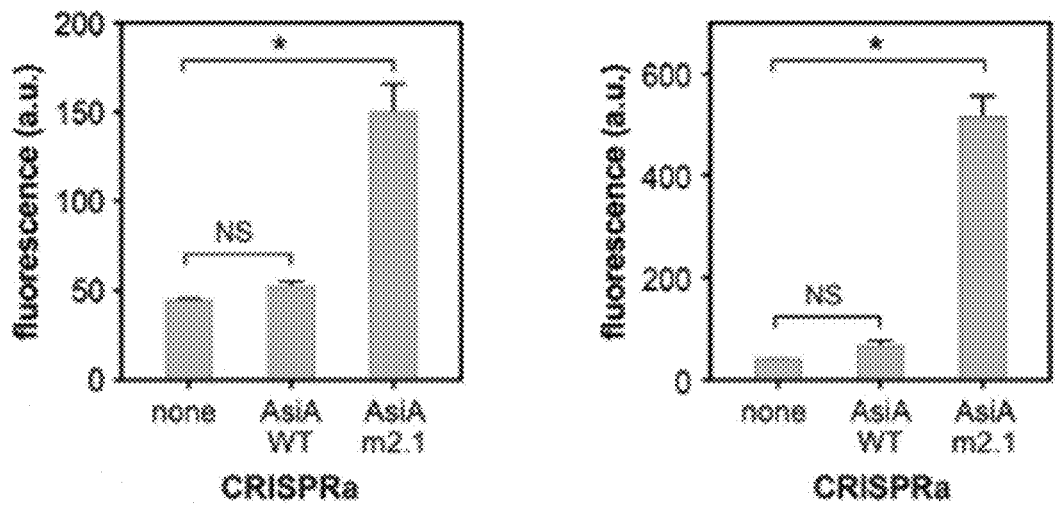

Since homologs of the T4 AsiA protein are widely found in many different phages that infect diverse bacteria (FIG. 5A), it was hypothesized that the dCas9-AsiA system could be ported to other bacteria with greater possibility of success and minimal re-optimization. Two bacterial species *Salmonella enterica* and *Klebsiella oxytoca* of clinic and bioindustrial significance were chosen to test the CasTA system. Each of the three plasmids (CasTA, gRNA, reporter) was transformed into the two species. dCas9 was functional in these two species, as confirmed by using a gRNA targeting for repression of a reporter GFP gene (e.g., CRISPRi) activity (FIG. 5B). CRISPRa was tested using the CasTA1.0 and 2.1 systems with the appropriate gRNA and GFP reporter. CasTA2.1 showed significant GFP activation in both species, but CasTA1.0 did not. It is interesting to note that AsiA from *Salmonella* phage SG1 shares the same residues at positions 50-61 as the *E. coli* T4 phage, while the *Klebsiella* phage F48 had some differences especially at residues 51-53, 57, and 59, which all face away from the binding surface to σ70. Notably, residues 51-53 and 57-61 of AsiA appear to be more variable across phylogenetically diverse phages (FIG. 5A), which are also the key residue regions mutated in m2.1 (Q51R, V58I, E60K) from our directed evolution experiments. In fact, some of the mutant residues in CasTA2.1 are also found in natural AsiA variants, suggesting that the mutations identified might mediate conserved molecular interactions leading to improved gene activation. Together, these results demonstrate that the CasTA system can be ported into other bacteria.

The scope of the present invention is not limited by what has been specifically shown and described hereinabove. Those skilled in the art will recognize that there are suitable alternatives to the depicted examples of materials, configurations, constructions, and dimensions. Variations, modifications, and other implementations of what is described herein will occur to those of ordinary skill in the art without departing from the spirit and scope of the invention.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

What is claimed is:

1. A fusion protein comprising a transcriptional effector, or variant or fragment thereof, linked to the C-terminal end of a Cas9 protein,
   wherein the transcriptional effector comprises an amino acid sequence of SEQ ID NO: 80 with a Q51R, V58I, or E60K mutation, or any combination thereof.

2. The fusion protein of claim 1, further comprising a linker between the Cas9 protein and the transcription effector.

3. The fusion protein of claim 1, wherein the Cas9 protein is a catalytically-dead Cas9 (dCas9).

4. A system comprising:
   the fusion protein of claim 1 and/or a first nucleic acid encoding the fusion protein; and
   at least one guide RNA (gRNA) and/or at least one second nucleic acid encoding the guide RNA sequence, wherein the at least one guide gRNA is complementary to a target DNA sequence.

5. The system of claim 4, wherein the system further comprises at least one reporter gene and/or at least one third nucleic acid encoding the reporter gene.

6. The system of claim 5, wherein the first nucleic acid, the at least one second nucleic acid, and the at least one third nucleic acid are on a single vector or different vectors.

7. The system of claim 5, wherein the target DNA sequence is upstream of the reporter gene transcription start site.

8. The system of claim 4, wherein the target DNA sequence is a DNA sequence in a host cell.

9. The system of claim 8, wherein the host cell is a bacterial cell.

10. A bacterial cell comprising the system of claim 4.

11. A method of altering transcription of a target gene in bacteria, comprising introducing the system of claim 4 into bacteria comprising the target DNA sequence.

* * * * *